United States Patent
Boyer et al.

(10) Patent No.: US 7,452,870 B2
(45) Date of Patent: *Nov. 18, 2008

(54) DRUG-ELUTING STENTS COATED WITH P2Y$_{12}$ RECEPTOR ANTAGONIST COMPOUND

(75) Inventors: José L. Boyer, Chapel Hill, NC (US); James G. Douglass, III, Apex, NC (US); Sammy R. Shaver, Chapel Hill, NC (US)

(73) Assignee: Inspire Pharmaceuticals, Inc., Durham, NC (US)

(*) Notice: Subject to any disclaimer, the term of this patent is extended or adjusted under 35 U.S.C. 154(b) by 309 days.

This patent is subject to a terminal disclaimer.

(21) Appl. No.: 11/267,834

(22) Filed: Nov. 4, 2005

(65) Prior Publication Data

US 2006/0122143 A1 Jun. 8, 2006

Related U.S. Application Data

(63) Continuation-in-part of application No. 10/814,007, filed on Mar. 30, 2004, now Pat. No. 7,132,408, which is a continuation-in-part of application No. 09/934,970, filed on Aug. 21, 2001, now Pat. No. 7,101,860, which is a continuation-in-part of application No. 09/643,138, filed on Aug. 21, 2000, now Pat. No. 7,018,985.

(51) Int. Cl.
*A01N 43/04* (2006.01)
*A61K 31/70* (2006.01)
*C07H 19/00* (2006.01)
*C07H 19/22* (2006.01)

(52) U.S. Cl. ................ 514/45; 514/43; 514/46; 514/47; 514/48

(58) Field of Classification Search ............ None
See application file for complete search history.

(56) References Cited

U.S. PATENT DOCUMENTS

| | | | |
|---|---|---|---|
| 3,321,463 A | 5/1967 | Moffatt et al. | 260/211.5 |
| 4,621,076 A | 11/1986 | Kuzuya et al. | 514/48 |
| 5,049,550 A | 9/1991 | Zamecnik | 514/47 |
| 5,654,285 A | 8/1997 | Ingall et al. | 514/47 |
| 5,681,823 A | 10/1997 | Kim et al. | 514/47 |
| 5,721,219 A | 2/1998 | Ingall et al. | 514/47 |
| 5,747,496 A | 5/1998 | Cox et al. | 514/258 |
| 5,814,609 A | 9/1998 | Markland et al. | 514/12 |
| 5,837,861 A | 11/1998 | Pendergast et al. | 536/25.6 |
| 5,900,407 A | 5/1999 | Yerxa et al. | 514/47 |
| 5,955,447 A | 9/1999 | Ingall et al. | 514/47 |
| 6,037,343 A | 3/2000 | Ali | 514/252 |
| 6,040,317 A | 3/2000 | Duggan et al. | 514/317 |
| 6,166,022 A | 12/2000 | Brown et al. | 514/258 |
| 6,323,187 B1 | 11/2001 | Yerxa et al. | 514/51 |
| 6,348,589 B1 | 2/2002 | Pendergast et al. | 536/25.6 |
| 6,528,640 B1 | 3/2003 | Beigelman et al. | 536/25.1 |
| 6,596,725 B2 | 7/2003 | Peterson et al. | 514/25.6 |
| 6,908,624 B2 | 6/2005 | Hossainy et al. | 424/424 |
| 2002/0052337 A1 | 5/2002 | Boyer et al. | 514/47 |
| 2004/0220133 A1 | 11/2004 | Boyer et al. | 514/47 |
| 2005/0233062 A1 | 10/2005 | Hossainy et al. | |

FOREIGN PATENT DOCUMENTS

| | | |
|---|---|---|
| GB | 1407903 | 10/1975 |
| WO | WO 89/04321 | 5/1989 |
| WO | WO 92/01673 | 7/1991 |
| WO | WO 92/17488 | 10/1992 |
| WO | WO 94/18216 | 8/1994 |
| WO | WO 97/03084 | 1/1997 |
| WO | WO 97/29456 | 8/1997 |
| WO | WO 98/03182 | 1/1998 |
| WO | WO 98/34593 | 8/1998 |
| WO | WO 99/01138 | 1/1999 |
| WO | WO 99/32085 | 1/1999 |
| WO | WO 98/28300 | 7/1999 |
| WO | WO 99/61012 | 12/1999 |
| WO | WO 00/33080 | 6/2000 |
| WO | WO 00/34283 | 6/2000 |

(Continued)

OTHER PUBLICATIONS

Aleil et al., "Flow Cytometric Analysis of Intraplatelet VASP Phosphorylation for the Detection of Clopidogrel Resistance in Patients with Ischemic Cardiovascular Diseases", *J. Thromb. Haemost.* 3:85-92; 2005.

(Continued)

*Primary Examiner*—Patrick T Lewis
(74) *Attorney, Agent, or Firm*—Howrey LLP; Viola T. Kung

(57) ABSTRACT

The present invention provides a P2Y$_{12}$ receptor antagonist compound-eluting stent, wherein the stent is coated with one or more P2Y$_{12}$ receptor antagonist compounds or a pharmaceutically acceptable salt, solvate, or hydrate thereof. When the stent is placed in a narrowed or damaged arterial vessel, a therapeutically effective amount of the P2Y$_{12}$ receptor antagonist compound is eluted continuously from the stent to the local environment of the stent. The P2Y$_{12}$ receptor antagonist compound-eluting stents are useful in preventing thrombosis and restenosis, and are effective in inhibiting the contraction of vascular smooth muscle cells, inhibiting cell proliferation, and reducing inflammation.

21 Claims, 15 Drawing Sheets

FOREIGN PATENT DOCUMENTS

| | | |
|---|---|---|
| WO | WO 00/39145 | 6/2000 |
| WO | WO 00/50024 | 8/2000 |
| WO | WO 01/19826 | 3/2001 |
| WO | WO 01/36421 | 5/2001 |
| WO | WO 01/39781 | 7/2001 |
| WO | WO 02/16381 A2 | 2/2002 |
| WO | PCT/US01/41818 | 3/2002 |
| WO | WO 94/08593 | 4/2004 |
| WO | WO 2005/040174 | 5/2005 |
| WO | WO 2005/097814 | 10/2005 |

OTHER PUBLICATIONS

Alessi, D. et al., "Synthesis and Properties of a Conformationally Restricted Spin-Labeled Analog of ATP and Its Interaction with Myosin and Skeletal Muscle" *Biochemistry* (1992), 31(34), 8043-54.

Antiplatelet Trialists' Collaboration., "Collaborative overview of randomised trials of antiplatelet therapy-I : Prevention of Death. myocardial infarction. and stroke by prolonged antiplatelet therapy in various categories of patients," *Br. Med. J.* 308: 81-106 (1994).

Antiplatelet Trialists' Collaboration., "Collaborative overview of randomised trials of antiplatelet therapy-II : Maintenance of Vascular graft or arterial patency by antiplatelet therapy," *Br. Med. J.* 308: 159-168 (1994).

Antman, E. for the TIMI 9a Investigators, "Hirudin in Acute Myocardial Infarction," *Circulation*, 90(4):1624-1630 (1994).

Bennett, et al., "Thrombotic Thrombocytopenic Purpura Associated with Clopidogrel", *N. Engl. J. Med.*, 342;1771-1777; 2000.

Bernat, A., et al., "Effect of Various Antiplatelet Agents on Acute Arterial Thrombosis in the Rat," *Thromb. Haemostas.* (1993) 70(5):812-816.

Bujalowski, W. et al., "Structural Characteristics of the Nucleotide-Binding Site of *Escherichia coli* Primary Replicative Helicase DnaB Protein. Studies with Ribose and Base-Modified Fluorescent Nucleotide Analogs" *Biochemistry* (1994), 33(15), 4682-94.

Bush, L., et al., "Effects of the selective thromboxane synthetase inhibitor dazoxiben on variations in cyclic blood flow in stenosed canie coronary arteries," Circulation 69(6): 1161-1170, (1984).

Cardullo, R. A. et al., "Synthesis, Purification, and Characterization of 2,4,6-Trinitrophenyl-UDP-galactose: A Fluorescent Substrate for Galactosyltransferase" *Analytical Biochemistry* (1990), 188(2), 305-9.

Carvalho-Alves, P. et al., "Stoichiometric Photolabeling of Two Distinct Low and High Affinity Nucleotide Sites in Sarcoplasmic Reticulum ATPase" *Journal of Biological Chemistry* (1985), 260(7), 4282-7.

Chapal, J. et al., "Comparative effects of adenosine-5'-triphosphate and related analogs on insulin secretion from the rat pancreas" *Fundamental & Clinical Pharmacology* (1997), 11(6), 537-545.

Doorty et al., "Poly(N-isopropylacrylamide) co-polymer films as potential vehicles for delivery of an antimitotic agent to vascular smooth muscle cells", *Cardiovascular Pathology* 12:105-110; 2003.

Douglass et al., INS50589, "A Potent, selective and reversible inhibitor of P2Y12 mediated platelet aggregation", abstract P848086, 229th ACS National Meeting, Mar. 13, 2005.

Folts, J. et al., "Platelet Aggregation In Partially Obstructed Vessels and its Elimination with Asprian," Circulation 54(3):365-370 (1976).

Frederick, L.G., et al., "The Protective Dose of the Potent GPIIb/IIIa Antagonist SC-54701A is Reduced When Used in Combination with Asprian and Heparin in a Canie Model of Coronary Artery Thrombosis," Circulation 93(1):129-134 (1996).

Geiger, J., et al., "Specific Impairment of Human Platelet P2Y ac ADP Receptor-Mediated Signaling by the Antiplatelet Drug Clopidogrel," *Arterioscler. Thromb. Vasc. Biol.* 19:2007-2011 (1999).

Gurbel et al., "Effect of Loading with Clopidogrel at the Time of Coronary Stenting on Platelet Aggregation and Glycoprotein IIb/IIIa Expression and Platelet-Leukocyte Aggregate Formation", *Am. J. Cardiol.* 90:312-315; 2002.

Gurbel et al., "Clopidogrel for Coronary Stenting", *Circulation* 107:2908-2913; 2003.

Hamilton, A. et al., "Design of Substrate-Site-Directed Inhibitors of Adenylate Kinase and Hexokinase. Effect of Substrate Substitutents on Affinity for the Adenine Nucleotide Sites", *J. Med. Chem.*, 19:1371-1377 (1976).

Hass, W., et al., "A Randomized Trial Comparing Ticlopidine Hydrochloride with Asprian for the Prevention of Stroke for High-Risk Patients," *N. Engl. J. Med.*, 321(8):501-507 (1989).

Hechler et al., "A Role of the Fast ATP-gated P2X1 Cation Channel in Thrombosis of Small Arteries in Vivo", *J. Exp. Med.* 198:661-667:2003.

Herbert, J.M. et al., Inhibitory Effect of Clopidogrel on Platelet Adhesion and Intimal Proliferation After Arterial Injury in Rabbits, *Arterioscl. Thromb.* (1993) 13(8):1171-1179.

Hiratsuka, Toshiaki, "Biological Activities and Spectroscopic Properties of Chromophoric and Fluorescent Analogs of Adenine Nucleoside and Nucleotides, 2',3'-O-(2,4,6-Trinitrocyclohexadienylidene) Adenosine Derivatives" *Biochimica et Biophysica Acta* (1982), 719(3), 509-17.

Hiratsuka T., "Affinity Labeling of the Myosin ATPase with Ribose-Modified Fluorescent Nucleotides and Vanadate", *J. Biochem.*, 96: 147-154 (1984).

Hiratsuka, Toshiaki, "Monitoring the Myosin ATPase Reaction Using a Sensitive Fluorescent Probe: Pyrene-Labeled ATP" *Biophysical Journal* (1997), 72(2, Pt. 1), 843-849.

Hourani et al., The Platelet ADP Receptors Meeting, La Thuile, Italy, Mar. 29-31, 2000.

Hourani et al., "Effects of the $P_2$-purinoceptor antagonist, suramin, on human platelet aggregation induced by adenosine 5'-diphosphate", *Br. J. Pharmacol.* 105:453-457; 1992.

Humphries, R.G., et al., "Pharmacological profile of the novel P2T-Purinoceptor antagonist, FPL 67085 in vitro and in the anaestheized rat in vitro," Br. J. Pharmacol. 115:1110-1116 (1995).

Ikehara, M. et al., "III. Interaction Between Synthetic Adenosine Triphosphate Analogs and Actomyosin Systems" *Biochimica et Biophysica Acta* (1965). 100(2), 471-8.

Ikehara, M. et al., "Unusual Rapid Cleavage of Terminal Phosphate Group of N6-Disubstituted Adenosine 5'-Triphosphate (ATP)by Divalent Cation" *Biochimica et Biophysica Acta* (1964), 85(3), 512-515.

Ingall, A., et al. , "Antagonists of the Platelet P2t Receptor: A Novel Approach to Antithrombotic Therapy," *J. Med. Chem.* 42: 213-220 (1999).

Kapetanakis et al., "Clopidogrel administration prior to coronary artery bypass grafting surgery: the cardiologist's panacea or the surgeon's headache?", *Eur. Heart J.* 26:576-583; 2005.

Kavanagh et al., "Local drug delivery in restenosis injury: thermoresponsive co-polymers as potential drug delivery systems", *Pharmacology & Therapeutics* 102:1-15; 2004.

Kim et al., "Characterization of the Purinergic $P_2$ Receptors in PC12 Cells", *J. Biol. Chem.* 269(9):6471-7; 1994.

Kwiatkowski, A. et al., "Mapping of the Adenosine 5'-triphosphate Binding Site of Type II Calmodulin-Dependent Protein Kinase" *Biochemistry* (1987), 26(24), 7636-40.

Lazarowski, E., et al., "Pharmacological selectivity of the cloned human P2u-purinoceptor: potent activation by diadenosine tetraphosphate," *Brit. J. Pharm.* 116:1619-1627 (1995).

Lekstrom, J and William R. Bell, "Aspirin in the Prevention of Thrombosis," *Medicine* 70(3):161-177 (1991).

Léon et al., "Key Role of the P2Y1 Receptor in Tissue Factor-Induced Thrombin-Dependent Acute Thromboembolism: Studies in P2Y1-Knockout Mice and Mice Treated with a P2Y1 Antagonist", *Circulation* 103:718-723; 2001.

Lowe, G. et al., "Evidence of a Dissociative $S_N1(P)$ Mechanism of Phosphoryl Transfer by Rabbit Muscle Pyruvate Kinase" *Journal of the Chemical Society, Perkin Transactions 1: Organic and Bio-Organic Chemistry* (1972-1999) (1978), (12), 1622-30.

Maffrand, et al., "ADP Plays a Key Role in Thrombogenesis in Rats", *Thromb. Haemostas.* 59:225-230; 1988.

Marian, M., "Acetyl Derivatives of Nucleoside 5'-Triphosphates. I." *Microchemical Journal* (1984), 29(2), 219-27.

Martin, P. et al., "Structure-Activity Studies of Analogs of β-γ-Methoylene-ATP at P2x Purinoceptors in the Rabbit Ear Central Artery", *Drug Development Research*, 36:153-165 (1995).

Mayer, I. et al., "Interaction of Fluorescent Adenine Nucleotide Derivatives with the ADP/ATP Carrier in Mitochondria. 1. Comparison of Various 3'-O-Ester Adenine Nucleotide Derivatives" *Biochemistry* (1984), 23(11), 2436-42.

Metzker, M. et al., "Termination of DNA Synthesis by novel 3'-modified-deoxyribonucleoside 5'-triphosphate", *Nucleic Acids Research*, 22: 4259-4267 (1994).

Mickelson, J.K., et al., "Antiplatelet Antibody [7E3 F(ab')2] Prevents Rethrombosis After Recombinant Tissue-Type Plasminogen Activator-Induced Coronary Artery Thrombolysis in a Canie Model," Circulation 81(2):617-627 (1990).

Moffatt, et al., "Nucleoside polyphosphates. VIII. New and Improved Syntheses of Uridine Diphosphate Glucose and Flavin Adenine Dinucleotide Using Nucleoside-5' Phosphoramidates", *Journal of the American Chemical Society*, 80, 3756-61 (1958).

Muni et al., "Coronary drug-eluting stent development: Issues in trial design", *American Heart Journal* 149:415-433; 2005.

Murataliev, M. et al., "Interaction of mitochondrial $F_1$-ATPase with trinitrophenyl derivatives of ATP. Photoaffinity labeling of binding sites with 2-azido-2',3'-O-(2,4,6-trinitrophenyl)adenosine 5'-triphosphate" *European Journal of biochemistry* (1995), 232(2), 578-85.

Neuhaus., K. L. et al., "Safety Observations from the Piolet Phase of the Randomized r-Hirudin for Improvement of Thrombolysis (HIT-III) Study," *Circulation*, 90(4): 1638-1642 (1994).

Oliveira, C. R. G. et al., "Interaction of Spin-Labeled Nucleotides with Sarcoplasmic Reticulum Adenosinetriphosphatase" *Biochemistry* (1988), 27(16), 5923-7.

Olivier, K., et al., "Acute Safety and Effects on Mucocillary Clearance of Aerosolized Uridine 5'—Triphosphate + Amiloride in Normal Human Adults,"—*Am. J. Respir. Crit. Care Med*. 154:217-223.

Pelicano, H. et al., "Study of the Substrate-binding Properties of Bovine Liver Adenosine Kinase and Inhibition by Fluorescent Nucleoside Analogues", *Eur. J. Biochem*., 248: 930-937 (1997).

Quinn, et al., "Ticlopidine and Clopidogrel," *Circulation* 100(15):1667-1672 (1992).

Ray, S. et al., "Microenvironment at the Substrate Binding Subsite of the Active Site of UDPglucose 4-Epimerase from Kluyveromyces Fragilis Using a Fluorescent Analog of UMP"0 *Indian Journal of Biochemistry & Biophysics* (1992), 29(2), 209-13.

Richard, J. et al., "Stereochemical Course of Thiophosphoryl Group Transfer Catalyzed by Adenylate Kinase", *J. Am. Chem. Soc*., 100 :7757-7758 (1978).

Rolf et al., "Platelet Shape Change Evoked by Selective Activation of P2X1 Purinoceptors with α,β-methylene ATP", *Thromb. Haemostas*. 85:303-308; 2001.

Romson, J., et al., "Electrical Induction of Coronary Artery Thrombosis in the Ambulatory Canine: A model for In Vivo Evaluation of Anti-Thrombotic Agents," Thromb. Res. 17:841-853 (1980).

Seebregts, C. et al., "2,3'-O-(2,4,6-Trinitrophenyl)-8-Azidoadenosine Mono-, Di-, and Triphosphates as Photoaffinity Probes of the $Ca^{2+}$-ATPase of Sarcoplasmic Reticulum. Regulatory/Superfluorescent Nucleotides Label the Catalytic Site with High Efficiency" *Journal of Biological Chemistry* (1989), 264(4), 2043-52.

Sekine, M. et al., "New Type of Chemical Oxidative Phosphorylation: Activation of Phosphonate Function by Use of Triisopropylbenzenesulfonyl Chloride", *Tetrahedron Letters*, 1145-1148 (1997).

Shebuski, R., et al., "Acceleration of Recombinant Tissue-Type Plasminogen Activator-Induced Thrombolysis and Prevention of Reocclusin by the Combination of Heparin and the Arg-Gly-Asp-Containing Peptide Bitistatin in a Canie Model of Coronary Thrombosis," Circulation 82(1):169-177 (1990).

Soslau, G. et al., "Aggregation of Human and Canine Platelets: Modulation by Purine Nucleotides" *Thrombosis Research* (1993), 72(2), 127-37.

The EPIC Investigators, "Use of Monoclonal Antibody Directed Against the Platelet Glycoprotein Iib/IIIa Receptor in High-Risk Coronary Angioplasty", *New Engl. J. Med*. 330:956-961; 1994.

The GUSTO Iia Investigators, The Global Use of Strategies to Open Occluded Coronary Arteries, "Randomized Trial of Intravenous Heparin Versus Recombinant Hirudin for Acute Coronary Syndromes", *Circulation*, 90:1631-1637; 1994.

Thoenges D. et al., "Tight Binding of Bulky Fluorescent Derivatives of Adenosine to the Low Affinity $E_2$ATP Site Leads to Inhibition of Na+/K+-ATPase. Analysis of Structural Requirements of Fluorescent ATP Derivatives with Koshland-Nemethy-Filmer Model of Two Interacting ATP Sites" *Journal of Biological Chemistry* (Jan. 22, 1999), 274(4), 1971-8.

Tschopp, J.F., et al., "Inhibition of coronary artery reocclusion after thrombolysis with an RGD-containing peptide with no significant effect on bleeding time," Coron. Artery Dis. 4:809-817(1993).

Vigne, P. et al., "Benzoyl ATP Is an Antagonist of Rat and Human $P2Y_1$ Receptors and of Platelet Aggregation" *Biochemical and Biophysical Research Communications* (1999), 256(1), 94-97.

Ward, D. et al., "Photoinactivation of Fluorescein Isothiocyanate-modified Na,K-ATPase by 2'(3')-O-(2,4,6-Trinitrophenyl)8-azidoadenosine 5'-Diphosphate. Abolition of E1 and E2 Partial Reactions by Sequential Block of High and Low Affinity Nucleotide Sites" *Journal of Biological Chemistry* (1998), 273(23), 14277-14284.

Weber, M., et al., "Low-Dose Asprian Verses Anticoagulants for Prevention of Coronary Graft Occlusion," *Am. J. Cardiol*. 66:1461-1468 (1990).

Wihlborg et al., "ADP Receptor P2Y12 is Expressed in Vascular Smooth Muscle Cells and Stimulates Contraction in Human Blood Vessels", *Arteriosl. Thromb. Vasc. Biol*. 24:1810-18151 2004.

Zatorski, A. et al., "Chemical Synthesis of Benzamide Adenine Dinucleotide: Inhibition of Inosine Monophosphate Dehydrogenase (Types I and II)", *Journal of Medicinal Chemistry, American Chemical Society*, 39: 2422-2426 (1996).

International Search Report: PCT/US2006/43085, mailed Jan. 22, 2008.

Conley et al., "Scientific and Therapeutic Insights into the Role of the Platelet P2Y12 Receptor in Thrombosis", Current Opinion in Hematology; vol. 10: 333338. Sep. 2003, p. 333 col. 1.

Jacobson et al., "Molecular Recognition at Adenine Nucleotide (P2) Receptors in Platelets", Seminars in Thrombosis and Hemostasis, vol. 31 (2), Apr. 2005, p. 212 col. 1, p. 211.

Boyer et al., "Development of Reversible P2Y12 Receptor Antagonists", 3rd International Meeting, ADP 2004, Sep. 16-18, 2004, entire document.

Douglass et al., "Effects of Ribose Modified Adenosine Phosphates in Models of Acute and Inflammatory Pain", Poster presented at the 4th International Symposium of Nucleosides and Nucleotides Purines; Jun. 6-9, 2004, p. 1 col. 1.

Kauffenstein et al., "Adenine Triphosphate Nucleotides are Antagonists at the P2Y12 Receptor", J Thromb Haemost; vol. 2:19801988, Nov. 2004, p. 1980 col. 1.

Pintor et al., "Diadenosine Polyphosphates in the Central Nervous System", Neuroscience Research Communications; vol. 20 (2), Dec. 20, 1996, p. 69.

Abbracchio et al., "International Union of Pharmacology LVIII: Update on the P2Y G Protein-Coupled Nucleotide Receptors: From Molecular Mechanisms and Pathophysiology to Therapy" Pharmacol Rev; vol. 58(3): 281-341, Sep. 2006, p. 294 col. 2.

US 7,452,870 B2

DRUG-ELUTING STENTS COATED WITH P2Y$_{12}$ RECEPTOR ANTAGONIST COMPOUND

This application is a continuation-in-part of U.S. application Ser. No. 10/814,007, filed Mar. 30, 2004, now U.S. Pat. No. 7,132,408 which is a continuation-in-part of U.S. application Ser. No. 09/934,970, filed Aug. 21, 2001, now U.S. Pat. No. 7,101,860 which is a continuation-in-part of U.S. application Ser. No. 09/643,138, filed Aug. 21, 2000 now U.S. Pat. No. 7,018,985. This application also claims the priority of PCT/US2005/011324, filed Mar. 30, 2005. The contents of the above applications are incorporated herein by reference in their entirety.

TECHNICAL FIELD

This invention relates to mono- and dinucleoside polyphosphate compounds and the method of using such compounds in the prevention or treatment of diseases or conditions associated with platelet aggregation, including thrombosis in humans and other mammals. This invention also relates to drug-eluting stents, wherein a therapeutically effective amount of a P2Y$_{12}$ receptor antagonist compound is eluted continuously from the stent to the local environment of the stent, when the stent is placed in a narrowed or damaged arterial vessel.

BACKGROUND OF THE INVENTION

Hemostasis is the spontaneous process of stopping bleeding from damaged blood vessels. Precapillary vessels contract immediately when cut; within seconds, thrombocytes, or blood platelets, are bound to the exposed matrix of the injured vessel by a process called platelet adhesion. Platelets also stick to each other in a phenomenon known as platelet aggregation to form a platelet plug to stop bleeding quickly.

An intravascular thrombus results from a pathological disturbance of hemostasis. Platelet adhesion and aggregation are critical events in intravascular thrombosis. Activated under conditions of turbulent blood flow in diseased vessels or by the release of mediators from other circulating cells and damaged endothelial cells lining the vessel, platelets accumulate at a site of vessel injury and recruit further platelets into the developing thrombus. The thrombus can grow to sufficient size to block off arterial blood vessels. Thrombi can also form in areas of stasis or slow blood flow in veins. Venous thrombi can easily detach portions of themselves called emboli that travel through the circulatory system and can result in blockade of other vessels, such as pulmonary arteries. Thus, arterial thrombi cause serious disease by local blockade, whereas venous thrombi do so primarily by distant blockade, or embolization. These conditions include venous thrombosis, thrombophlebitis, arterial embolism, coronary and cerebral arterial thrombosis, unstable angina, myocardial infarction, stroke, cerebral embolism, kidney embolisms and pulmonary embolisms.

A number of converging pathways lead to platelet aggregation. Whatever the initial stimulus, the final common event is crosslinking of platelets by binding fibrinogen to a membrane binding site, glycoprotein IIb/IIIa (GPIIb/IIIa). Compounds that are antagonists for GPIIb/IIIa receptor complex have been shown to inhibit platelet aggregation (U.S. Pat. Nos. 6,037,343 and 6,040,317). Antibodies against GPIIb/IIIa have also been shown to have high antiplatelet efficacy (The EPIC investigators, *New Engl. J. Med.* (1994) 330:956-961). However, this class of antiplatelet agents sometimes causes bleeding problems.

Thrombin can produce platelet aggregation largely independently of other pathways but substantial quantities of thrombin are unlikely to be present without prior activation of platelets by other mechanisms. Thrombin inhibitors such as hirudin are highly effective antithrombotic agents. However, functioning as both antiplatelet and anti-coagulant agents, thrombin inhibitors again can produce excessive bleeding. (The TIMI 9a investigators, The GUSTO IIa investigators, *Circulation*, 90: 1624-1630 (1994); *Circulation*, 90: 1631-1637 (1994); Neuhaus K. L. et al., *Circulation*, 90: 1638-1642 (1994).)

Various antiplatelet agents have been studied for many years as potential targets for inhibiting thrombus formation. Some agents such as aspirin and dipyridamole have come into use as prophylactic antithrombotic agents, and others have been the subjects of clinical investigations. To date, the powerful agents such as disintegrins, and the thienopyridines ticlopidine and clopidogrel have been shown to have substantial side effects, while agents such as aspirin have useful but limited effectiveness (Hass, et al., *N. Engl. J. Med.,* 321:501-507 (1989); Weber, et al., *Am. J. Cardiol.* 66:1461-1468 (1990); Lekstrom and Bell, *Medicine* 70:161-177 (1991)). In particular, use of the thienopyridines in antiplatelet therapy has been shown to increase the incidence of potentially life threatening thrombotic thrombocytopenic purpura (Bennett, C. L. et al. *N. Engl. J. Med*, (2000) 342: 1771-1777). Aspirin, which has a beneficial effect on platelet aggregation (*Br. Med. J.* (1994) 308: 81-106; 159-168), acts by inducing blockade of prostaglandin synthesis. Aspirin has no effect on ADP-induced platelet aggregation, and thus has limited effectiveness on platelet aggregation. Furthermore, its well-documented high incidence of gastric side effects limits its usefulness in many patients. Clinical efficacy of some newer drugs, such as ReoPro (7E3), is impressive, but recent trials have found that these approaches are associated with an increased risk of major bleeding, sometimes necessitating blood transfusion (*New Engl. J. Med.* (1994) 330:956-961). Thus it appears that the ideal "benefit/risk" ratio has not been achieved.

Recent studies have suggested that adenosine 5'-diphosphate (ADP), a common agonist, plays a key role in the initiation and progression of arterial thrombus formation (Bernat, et al., *Thromb. Haemostas.* (1993) 70:812-826); Maffrand, et al., *Thromb. Haemostas.* (1988) 59:225-230; Herbert, et al., *Arterioscl. Thromb.* (1993) 13:1171-1179). ADP induces platelet aggregation, shape change, secretion, influx and intracellular mobilization of Ca$^{+2}$, and inhibition of adenylyl cyclase. Binding of ADP to platelet receptors is required for elicitation of the ADP-induced platelet responses. There are at least three P2 receptors expressed in human platelets: a cation channel receptor P2X$_1$, a G protein-coupled receptor P2Y$_1$, and a G protein-coupled receptor P2Y$_{12}$ (also referred to as P2Y$_{ac}$ and P2$_T$) The P2X$_1$ receptor is responsible for rapid calcium influx and is activated by ATP. The role of P2X$_1$ receptors in the process of platelet aggregation is not fully understood. However, it has been suggested that the P2X$_1$ receptor participates in platelet shape change (Rolf, et al., *Thromb Haemost.* 85:303-308, 2001), and in platelet thombi formation under high shear forces. (Hechler, et al., *J Exp Med.* 198: 661-667, 2003). The P2Y$_1$ receptor is responsible for calcium mobilization, shape change and the initiation of aggregation. P2Y$_{12}$ receptor is responsible for inhibition of adenylyl cyclase and is required for full aggregation. (Hourani, et al., The Platelet ADP Receptors Meeting, La Thuile, Italy, Mar. 29-31, 2000.)

Ingall et al. (*J. Med. Chem.* 42: 213-220, (1999)) describe a dose-related inhibition of ADP-induced platelet aggregation by analogues of adenosine triphosphate (ATP), which is a weak, nonselective but competitive $P2Y_{12}$ receptor antagonist. Zamecnik (U.S. Pat. No. 5,049,550) discloses a method for inhibiting platelet aggregation in a mammal by administering to said mammal a diadenosine tetraphosphate compound of $App(CH_2)ppA$ or its analogs. Kim et al. (U.S. Pat. No. 5,681,823) disclose $P^1$, $P^4$-dithio-$P^2$, $P^3$-monochloromethylene 5', 5'" diadenosine $P^1$, $P^4$-tetraphosphate as an antithrombotic agent. The thienopyridines ticlopidine and clopidogrel, which are metabolized to antagonists of the platelet $P2Y_{12}$ receptor, are shown to inhibit platelet function in vivo (Quinn and Fitzgerald, *Circulation* 100:1667-1672 (1999); Geiger, et al., *Arterioscler. Thromb. Vasc. Biol.* 19:2007-2011 (1999)). However, these thienopyridines have a number of therapeutic disadvantages:

Slow onset of action (Gurbel, et al., *Am J. Cardiol.* 90: 312-315, 2002)

Due to the irreversible nature of these inhibitors on the $P2Y_{12}$ receptor, subjects treated with thienopyridines are at a high risk of bleeding if a surgical procedure is necessary. For elective surgeries, discontinuation of the drug is necessary for at least five to ten days since production of new platelets is necessary to restore hemostasis, exposing the subject to a high risk of thrombotic events during this period (Kapetanakis, et al., *Eur Heart J.* 26: 576-583, 2005).

Subjects treated with the standard dose regimen of these compounds present a large inter-individual variability in the pharmacological effect of the drug, with a significant proportion of patients underprotected from the occurrence of ischemic events. (Gurbel, et al., *Circulation* 107: 2908-2913, 2003; Aleil, et al., *J Thromb Haemost.* 3: 85-92, 2005).

Stents are typically slotted metal tubes, which can be expanded by a balloon in an angioplastied artery, providing a rigid structural support for the arterial wall. The use of coronary stents for the treatment of patients with acute coronary syndrome has increased significantly during the past years. With coronary stents implanted in more than 2 million people worldwide, some doctors and researchers are now concerned about a long-term problem of blood clots inside the stents that is observed in some patients who have received stents.

In-stent restenosis is caused primarily due to hyperplasia of smooth muscle cells in the intimal layer of the vessel wall (so-called neointimal hyperplasia) and, to a much lesser extent, mural thrombus. On the molecular and cellular levels, the initial vascular injury caused by both inflation of intracoronary balloons and the metal of the stent itself results in denudation of the intima and stretching of the media and adventitia, in addition, both macrophages and polymorphonuclear neutrophils migrate to the site of damage, where they release chemokines. These chemokines serve to increase the amount of matrix metalloproteinase, which leads to remodeling of the extracellular matrix and stimulate smooth muscle cell migration. The wound healing reaction stimulates platelets, growth factor and smooth muscle cell activation, followed by smooth muscle cell and fibroblast migration and proliferation into the injured area. Smooth muscle cells are also stimulated to increase the expression of genes involved in cell division. It is both the interaction and the extent of these processes that lead to neointimal hyperplasia and in-stent restenosis, which are characterized by a marked proliferative response produced by the stent as has been demonstrated by histological examinations. Stenting also raises the systemic levels of inflammatory markers such as C-reactive protein and interleukin-6.

Recently, stents are coated with agents that reduce or prevent exaggerated neointimal proliferation, and thereby, restenosis. For example, paclitaxel-eluting stents inhibit the proliferation of smooth muscle cells, and sirolimus-eluting stents inhibits the inflammation response of the arterial wall. One problem with these stents is that the drugs also inhibit the regeneration of the endothelium destroyed during the expansion of the narrowed artery, creating a potential risk of thrombosis. Thus, the placement of these stents often requires the treatment by systemic administration of antithrombotic drugs.

There is a need in the area of cardiovascular and cerebrovascular therapeutics for improved stents.

SUMMARY OF THE INVENTION

This invention is directed to a method of preventing or treating diseases or conditions associated with platelet aggregation and/or platelet activation; such diseases include venous thrombosis, thrombophlebitis, arterial embolism, coronary and cerebral arterial thrombosis, unstable angina, myocardial infarction, stroke, cerebral embolism, kidney embolisms and pulmonary embolisms. The method is also directed to a method of preventing, treating or reducing the incidence of thrombosis, thrombotic events, embolic events or pathological conditions associated with such events, where the thrombosis, thrombotic event or embolic event occurs during or after surgery.

The method comprises administering to a subject a pharmaceutical composition comprising a therapeutic effective amount of $P2Y_{12}$ receptor antagonist compound, wherein said amount is effective to bind the $P2Y_{12}$ receptors on platelets and inhibit ADP-induced platelet aggregation.

The $P2Y_{12}$ receptor antagonist compounds useful for this invention include compounds of general Formula I, or salts thereof:

Formula I

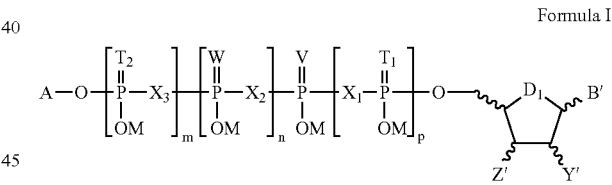

wherein:
$X_1$, $X_2$, and $X_3$ are independently oxygen, methylene, monochloromethylene, dichloromethylene, monofluoromethylene, difluoromethylene, or imido;

$T_1$, $T_2$, W, and V are independently oxygen or sulfur;

m=0, 1 or 2;

n=0 or 1;

p=0, 1, or 2;

where the sum of m+n+p is from 0 to 5; (monophosphate to hexaphosphate) M=H or a pharmaceutically-acceptable inorganic or organic counterion;

$D_1$=O or $CH_2$;

B' is a purine or a pyrimidine residue according to general Formulae IV and V which is linked to the 1' position of the furanose or carbocycle via the 9- or 1-position of the base, respectively;

Y'=H, OH, or $OR_1$;

Z'=H, OH, or $OR_2$;

with the proviso that when A=M, at least one of Y' and Z' is equal to $OR_1$ or $OR_2$ respectively;

A=M, or

A is a nucleoside residue which is defined as:

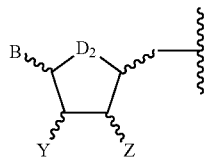

and is linked to the phosphate chain via the 5' position of the furanose or carbocycle; wherein:

$D_2$=O or $CH_2$;

Z=H, OH, or $OR_3$;

Y=H, OH, or $OR_4$;

with the proviso that at least one of Y', Z', Y and Z is equal to $OR_1$, $OR_2$ $OR_3$ or $OR_4$ respectively;

B is a purine or a pyrimidine residue according to general Formulae IV and V which is linked to the 1'-position of the furanose or carbocycle via the 9- or 1-position of the base, respectively;

$R_1$, $R_2$, $R_3$, and/or $R_4$ are residues which are linked directly to the 2'- and/or 3'-hydroxyls of the respective furanose or carbocycle via a carbon atom according to Formula II, or linked directly to two (2'- and 3'-) hydroxyls of the respective furanose or carbocycle via a common carbon atom according to Formula III, such that from one to four independent residues of $R_1$, $R_2$, $R_3$ and $R_4$ falling within the definition of Formula II are present or from one to two independent residues made up of $R_1+R_2$ and/or $R_3+R_4$ are present.

The present invention also provides a drug-eluting stent, wherein the stent is coated with one or more $P2Y_{12}$ receptor antagonist compounds of general Formula I, or a pharmaceutically acceptable salt, solvate, or hydrate thereof. When the stent is placed in a vessel, a therapeutically effective amount of the $P2Y_{12}$ receptor antagonist compound is eluted to the local environment of the stent. The $P2Y_{12}$ receptor antagonist compound-eluting stents are useful in preventing thrombosis and restenosis, and are effective in inhibiting the contraction of vascular smooth muscle cells, inhibiting cell proliferation, and reducing inflammation.

DETAILED DESCRIPTION OF THE INVENTION

Definitions

Figure 1:
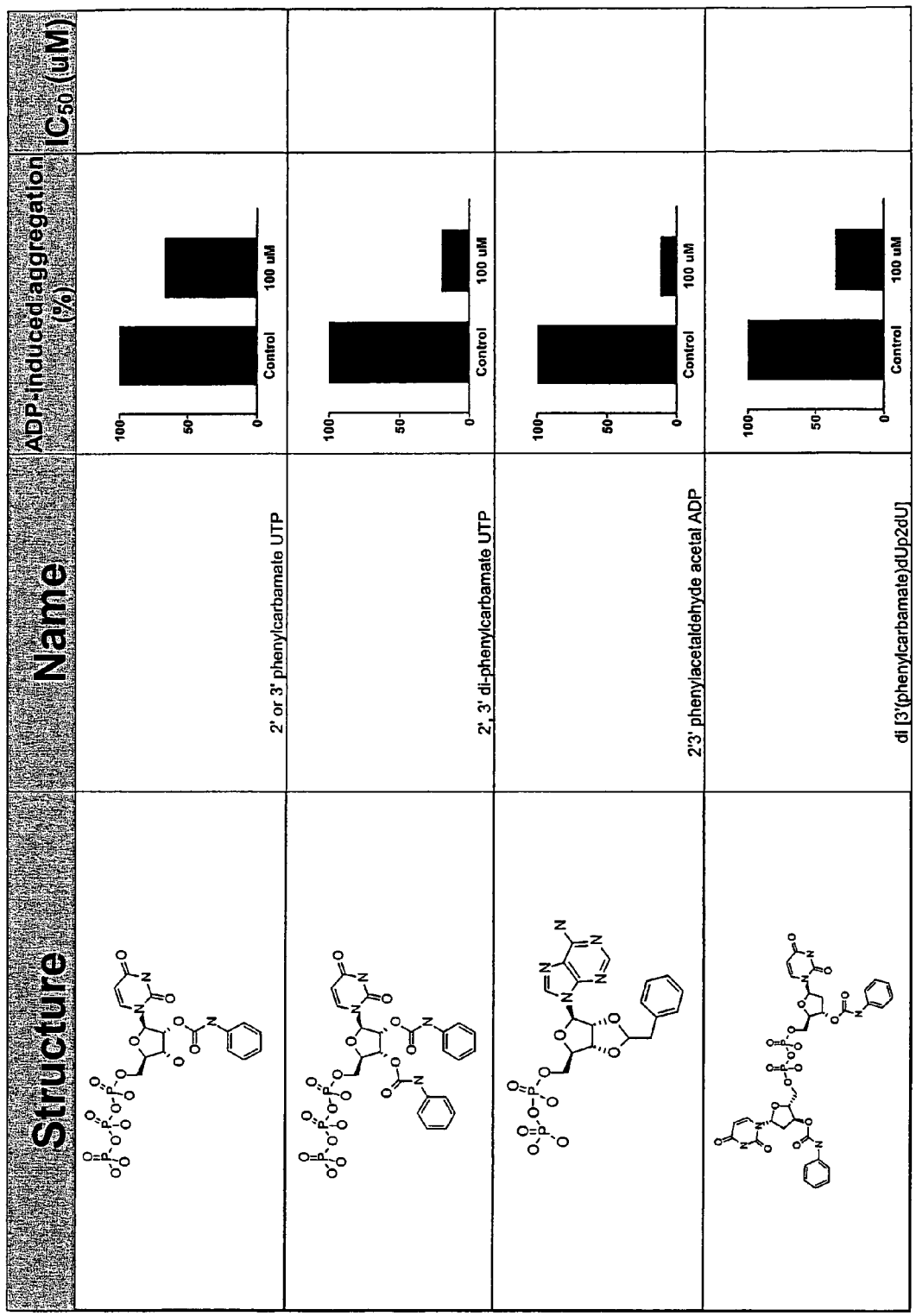
FIG. 1 shows the effect of inhibition of ADP-induced aggregation by different compounds.

When present, unless otherwise specified, the following terms are generally defined as, but are not limited to, the following:

Alkyl groups are from 1 to 12 carbons inclusively, either straight chained or branched, with or without unsaturation and with or without heteroatoms, are more preferably from 2 to 8 carbons inclusively, and most preferably 2 to 6 carbons inclusively.

Cycloalkyl groups from 3 to 12 carbons inclusively, more preferably from 3 to 10 carbons inclusively, and most preferably 3 to 6 carbons inclusively, with or without unsaturation, and with or without heteroatoms.

Aralkyl groups are from 1 to 8 carbons inclusively in the alkyl portion, are more preferably from 1 to 6 carbons inclusively in the alkyl portion, and most preferably are 1 to 4 carbons inclusively in the alkyl portion; as included in the alkyl definition above, the alkyl portion of an aralkyl group can include one or more positions of unsaturation such as a double bonds or a triple bond in the chain when the chain includes two or more carbon atoms; the alkyl portion of an aralkyl group can also include one or more heteroatoms and/or substituents; the aryl portion of an aralkyl group can be a monocyclic or polycyclic moiety from 3 to 8 carbons inclusively per ring in the aryl portion, more preferably from 4 to 6 carbons inclusively per ring, and most preferably 5 to 6 carbons inclusively per ring; the aryl portion of an aralkyl group can also bear one or more substituents and/or heteroatoms.

Aryl groups are either monocyclic or polycyclic, are from 3 to 8 carbons inclusively per ring, are more preferably from 4 to 6 carbons inclusively per ring, and are most preferably 5 to 6 carbons inclusively per ring; aryl groups can also bear substituents and/or heteroatoms.

Heteroaralkyl groups are from 1 to 8 carbons inclusively in the alkyl portion, are more preferably from 1 to 6 carbons inclusively in the alkyl portion, and most preferably are 1 to 4 carbons inclusively in the alkyl portion; as included in the alkyl definition above, the alkyl portion of a heteroaralkyl group can include one or more positions of unsaturation such as a double bonds or a triple bond in the chain when the chain includes two or more carbon atoms; the alkyl portion of a heteroaralkyl group can also include one or more heteroatoms and/or substituents; the heteroaryl portion of a heteroaralkyl group can be a monocyclic or polycyclic moiety from 3 to 8 carbons inclusively per ring in the heteroaryl portion and containing from 1 to 4 heteroatoms inclusively per ring, more preferably from 4 to 6 carbons inclusively per ring, and most preferably 5 to 6 carbons inclusively per ring; the heteroaryl portion of an heteroaralkyl group can also bear one or more substituents and/or heteroatoms.

Heteroaryl groups are either monocyclic or polycyclic, contain from 1 to 4 heteroatoms inclusively per ring, are from 3 to 8 atoms inclusively per ring, are more preferably from 4 to 6 atoms inclusively per ring, and are most preferably 5 to 6 atoms inclusively per ring; heteroaryl groups can also bear substituents and/or heteroatoms.

Substituents on the foregoing groups can be, but are not limited to, hydroxy, nitro, methoxy, fluoro, chloro, bromo, iodo, methyl, ethyl, propyl, butyl, thioalkyl, alkoxy, carboxyl, carboxamido, alkylsulfonyl, alkylsulfonylamino, sulfonamido, cyano, amino, substituted amino, trifluoromethyl, trifluoromethoxy, phenyl, pyridyl, imidazolyl, cyclopropyl, cyclopentyl, and cyclohexyl; and preferred heteroatoms are oxygen, nitrogen, and sulfur.

Diastereomers are stereoisomers (isomers of identical constitution but differing three-dimensional architecture), which do not bear a mirror-image relation to each other.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$). In the case of mono- or di-phosphates of nucleosides of the present invention, the salt forms are typically to be alkali-earth metals such as sodium, potassium, lithium or basic salts such as ammonium.

Solvates are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tertbutanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definition of the compound of the present invention encompasses all possible hydrates and solvates, in any proportion, which possess the stated activity.

$P2Y_{12}$ Receptor Antagonist Compounds

The $P2Y_{12}$ receptor antagonist compounds useful for preventing or treating diseases or conditions associated with platelet aggregation and/or platelet activation include compound of general Formula I, or a pharmaceutically acceptable salt, solvate, or hydrate thereof:

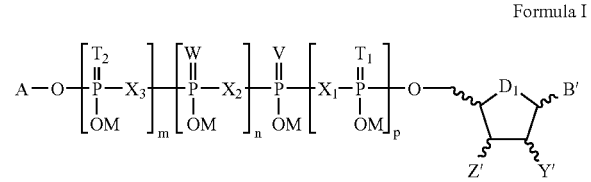

Formula I wherein:

$X_1$, $X_2$, and $X_3$ are independently oxygen, methylene, monochloromethylene, dichloromethylene, monofluoromethylene, difluoromethylene, or imido;

$T_1$, $T_2$, W, and V are independently oxygen or sulfur;

m=0, 1 or 2;

n=0 or 1;

p=0, 1, or 2;

where the sum of m+n+p is from 0 to 5; (from monophosphate to hexaphosphate)

M=H, or a pharmaceutically-acceptable inorganic or organic counterion;

$D_1$=O or $CH_2$

B' is a purine or a pyrimidine residue according to general Formulae IV and V which is linked to the 1'-position of the furanose or carbocycle via the 9- or 1-position of the base, respectively;

Y'=H, OH, or $OR_1$;

Z'=H, OH, or $OR_2$; with the proviso that when A=M, at least one of Y' and Z' is $OR_1$ or $OR_2$;

A=M, or

A is a nucleoside residue which is defined as:

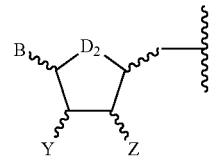

and which is linked to the phosphate chain via the 5'-position of the furanose or carbocycle; wherein:

$D_2$=O or $CH_2$;

Z=H, OH, or $OR_3$;

Y=H, OH, or $OR_4$;

with the proviso that at least one of Y', Z', Y and Z is equal to $OR_1$, $OR_2$ $OR_4$ or $OR_3$ respectively.

B is a purine or a pyrimidine residue according to general Formulae IV and V which is linked to the 1' position of the furanose or carbocycle via the 9- or 1-position of the base, respectively;

$R_1$, $R_2$, $R_3$, and/or $R_4$ are residues which are linked directly to the 2'- and/or 3'-hydroxyls of the respective furanose or carbocycle via a carbon atom according to Formula II, or linked directly to two (2'- and 3'-) hydroxyls of the respective furanose or carbocycle via a common carbon atom according to Formula III, such that from one to four independent residues of $R_1$, $R_2$, $R_3$ and $R_4$ falling within the definition of Formula II are present or from one to two independent residues made up of $R_1+R_2$ and/or $R_3+R_4$ are present;

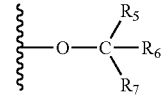

Formula II wherein:

O is the corresponding 2'- and/or 3'-oxygen of the respective furanose or carbocycle;

C is a carbon atom;

$R_5$, $R_6$, and $R_7$ are H, alkyl, cycloalkyl, aralkyl, aryl, substituted aralkyl, or substituted aryl, such that the moiety defined according to Formula II is an ether; or $R_5$ and $R_6$ are H, an alkyl, cycloalkyl, aralkyl, aryl, substituted aralkyl, or substituted aryl, and $R_7$ is alkoxy, cycloalkoxy, aralkyloxy, aryloxy, substituted aralkyloxy, or substituted aryloxy such that the moiety defined according to Formula II is an acyclic acetal or ketal; or $R_5$ and $R_6$ are taken together as oxygen or sulfur doubly bonded to C, and $R_7$ is alkyl, cycloalkyl, aralkyl, aryl, substituted aralkyl, or substituted aryl, such that the moiety defined according to Formula II is an ester or thioester; or $R_5$ and $R_6$ are taken together as oxygen or sulfur doubly bonded to C, and $R_7$ is amino or mono- or disubstituted amino, where the substituents are alkyl, cycloalkyl, aralkyl, aryl, substituted aralkyl, or substituted aryl, such that the moiety according to Formula II is a carbamate or thiocarbamate; or $R_5$ and $R_6$ are taken together as oxygen or sulfur doubly bonded to C, and $R_7$ is alkoxy, cycloalkoxy, aralkyloxy, aryloxy, substituted aralkyloxy, or substituted aryloxy, such that the moiety according to Formula II is a carbonate or thiocarbonate; or $R_7$ is not present and $R_5$ and $R_6$ are taken together as oxygen or sulfur doubly bonded to C and both the 2'- and 3'-oxygens of the respective furanose or carbocycle are directly bound to C to form a cyclical carbonate or thiocarbonate;

Formula III

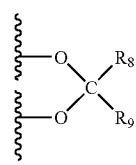

wherein the O atoms are the 2'- and 3'-oxygens of a furanose or carbocycle; and the 2'- and 3'-oxygens of the furanose or carbocycle are linked by a common carbon atom (C) to form a cyclical acetal, cyclical ketal, or cyclical orthoester;

for cyclical acetals and ketals, $R_8$ and $R_9$ are independently hydrogen, alkyl, cycloalkyl, aralkyl, aryl, substituted aralkyl, substituted aryl, or can be joined together to form a homocyclic or heterocyclic ring composed of 3 to 8 atoms, preferably 3 to 6 atoms;

for cyclical orthoesters, $R_8$ is hydrogen, alkyl, cycloalkyl, aralkyl, aryl, substituted aralkyl, or substituted aryl, $R_9$ is alkyloxy, cycloalkyloxy, aralkyloxy, aryloxy, substituted aralkyloxy, or substituted aryloxy.

For compounds of Formula I, B and B' can independently be a purine residue, as in Formula IV, linked through the 9-position, or a pyrimidine residue, as in Formula V, linked through the 1-position. The ribosyl moieties in Formulae Ia, Ib, Ia-1, and Ib-1 are in the D-configuration as shown, but can also be L-, or D- and L-. The D-configuration is preferred for ribosyl moieties.

Formula IV

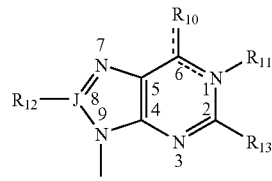

Formula V

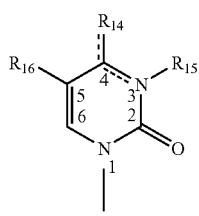

wherein:

$R_{10}$ and $R_{14}$ independently are hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or $R_{10}$ and $R_{14}$ independently are acylamino, provided that they incorporate an amino residue from the C-6 position of the purine or the C-4 position of the pyrimidine; or when $R_{10}$ in a purine or $R_{14}$ in a pyrimidine has as its first atom nitrogen, $R_{10}$ and $R_{11}$ or $R_{14}$ and $R_{15}$ can be taken together to form a 5-membered fused imidazole ring (to give an etheno compound), optionally substituted on the etheno ring with one or more alkyl, cycloalkyl, aralkyl, or aryl moieties, as described for $R_5$-$R_9$ above;

J is carbon or nitrogen, with the provision that when J=nitrogen, $R_{12}$ is not present;

$R_{11}$ is hydrogen, O (adenine 1-oxide derivatives) or is absent (adenine derivatives);

$R_{15}$ is hydrogen, or acyl (e.g. acetyl, benzoyl, phenylacyl, with or without substituents);

$R_{12}$ is hydrogen, alkyl, bromo, azido, alkylamino, arylamino or aralkylamino, alkoxy, aryloxy or aralkyloxy, alkylthio, arythio or aralkylthio, or $\omega$-A($C_{1-6}$alkyl)B-, wherein A and B are independently amino, mercapto, hydroxy or carboxyl;

$R_{13}$ is hydrogen, chlorine, amino, monosubstituted amino, disubstituted amino, alkylthio, arylthio, or aralkylthio, where the substituent on sulfur contains up to a maximum of 20 carbon atoms, with or without unsaturation, and with or without substituents on the chain;

$R_{16}$ is hydrogen, methyl, alkyl, halogen, alkyl, alkenyl, substituted alkenyl, alkynyl, or substituted alkynyl.

Compounds according to Formulae IV and V where $R_{10}$ or $R_{14}$ is acylamino fall within the scope of Formula VI:

Formula VI

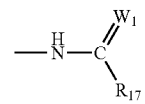

wherein:

NH is the amino residue at the C-6 position in a purine or the amino residue at the C-4 position in a pyrimidine;

C is a carbon atom;

$W_1$ is oxygen or sulfur;

$R_{17}$ is amino or mono- or disubstituted amino, with the amino substituent(s) being alkyl, cycloalkyl, aralkyl, or aryl, with or without further substituents, unsaturation, or heteroatoms, such that the moiety according to Formula VI is a urea or thiourea; or $R_{17}$ is alkoxy, aralkyloxy, aryloxy, substituted aralkyloxy, or substituted aryloxy, such that the moiety according to Formula VI is a carbamate or thiocarbamate; or $R_{17}$ is alkyl, cycloalkyl, aralkyl, or aryl, with or without substituents or heteroatoms, such that the moiety according to Formula VI is an amide; with definitions of alkyl, cycloalkyl, aralkyl, or aryl groups as previously defined for comparable groups in $R_5$ to $R_9$ When $R_5$, $R_6$ and $R_7$ are not the same, or when $R_8$ and $R_9$ are not the same, a compound according to Formula I can exist in several diastereomeric forms. The general structure of Formula I includes all diastereomeric forms of such materials, when not specified otherwise. Formula I also includes mixtures of compounds of Formula I, including mixtures of enantiomers, diastereomers and/or other isomers in any proportion.

One embodiment of the invention is that A=M, wherein M=H or a pharmaceutically acceptable inorganic or organic counterion. In such an embodiment, the compound can be a nucleoside monophosphate, nucleoside diphosphate, nucleoside triphosphate, nucleoside tetraphosphate, nucleoside pentaphosphate, or nucleoside hexaphosphate with one or both of the 2'- and/or 3'-positions of the furanose or carbocycle modified. Most preferred are nucleotide monophosphates, nucleotide diphosphates, nucleotide triphosphates, and nucleotide tetraphosphates. When $T_2$, W, V, or $T_1$ are sulfur, the preferred position for this atom is on the terminal phosphorous of the polyphosphate chain (i.e. the phosphorous furthest removed from the nucleoside residue).

For monophosphates, where m, n, and p are all equal to zero, preferably $R_8$ is hydrogen and $R_9$ is aryl or aralkyl, with 1, 2, 3, or 4 carbons inclusively in the alkyl portion of an aralkyl group, and 6 carbons inclusively in the aryl portion of an aralkyl or aryl group; when the number of carbons in the alkyl portion of an aralkyl group is 2, the carbon atoms are most preferably connected by either a double or triple bond.

Another embodiment of the invention is that A is a nucleoside residue defined as:

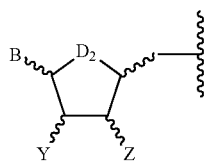

and linked to the phosphate chain via the 5'-position of the furanose or carbocycle (to give a dinucleoside polyphosphate with at least one of the 2'-, 3'-, 2"- and 3"-positions of the furanose or carbocycle moieties modified to be $OR_1$, $OR_2$, $OR_4$ or $OR_3$ respectively).

When $T_2$, W, V, and/or $T_1$ are sulfur, the preferred positions (for sulfur) are $T_1$ and $T_2$.

Further provisions are that when either $D_1$ or $D_2$ are oxygen, the corresponding furanose is preferably in the β-configuration; and that the corresponding furanose is preferably in the β-D-configuration.

In one embodiment, compounds of general Formula I are molecules whose structures fall within the definitions of Formula Ia or Formula Ib:

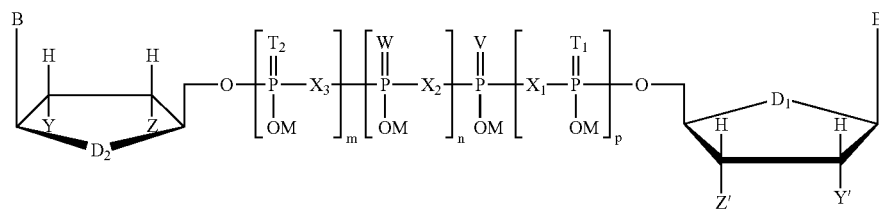

Formula Ia wherein:
$D_1$=O or $CH_2$;
$D_2$=O or $CH_2$;
B and B' are independently purine or pyrimidine residues according to general Formula IV or V;
m and p=0, 1 or 2; n=0 or 1; such that the sum of m+n+p is from 0 to 5, preferably 0 to 4, and most preferably 0 to 3;

B' is a purine or pyrimidine residue according to general Formulae IV and V;

$X_1$ and $X_2$ are independently O, NH, $CH_2$, CHF, CHCl, $CF_2$, $CCl_2$;
$T_1$, V, and W are independently O or S;
Y'=H, OH, or $OR_1$,
$X_1$, $X_2$, and $X_3$=are independently O, NH, $CH_2$, CHF, CHCl, $CF_2$, $CCl_2$;
$T_1$, $T_2$, V, and W are independently O or S;
M=H+, $NH_4^+$, $Na^+$ or other pharmaceutically-acceptable inorganic or organic counter ion;
Y'=H, OH, or $OR_1$;
Z'=OH or $OR_2$;
Z=OH or $OR_3$;
Y=H, OH, or $OR_4$, where $R_1$, $R_2$, $R_3$ and $R_4$ fall under the definition of general Formulae II or III, provided that at least one of Y', Z', Z and Y is $OR_1$, $OR_2$, $OR_3$, or $OR_4$.

Preferred compounds of Formula Ia include:
$D_1$=O or $CH_2$;
$D_2$=O or $CH_2$;
$X_1$, $X_2$, and $X_3$=O;
$T_1$, $T_2$, V, and W=O; or
$D_1$=O or $CH_2$;
$D_2$=O or $CH_2$;
$X_1$ and $X_3$=O;
$X_2$=methylene, monochloromethylene, dichloromethylene, monofluoromethylene, difluoromethylene, or imido;
T, $T_1$, $T_2$, V, and W=O; or
$D_1$=O or $CH_2$;
$D_2$=O or $CH_2$;
m, n, and p=1; or
$X_1$ and $X_3$=O;
$X_2$=methylene, monochloromethylene, dichloromethylene, monofluoromethylene, difluoromethylene, or imido;
$T_1$ and $T_2$=S;
V and W=O.

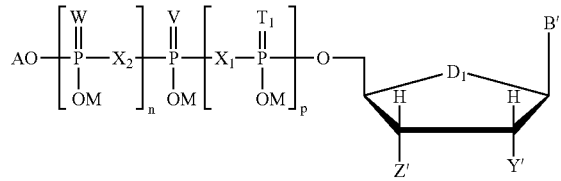

Formula Ib $D_1$=O or $CH_2$;
n and p=0, 1, or 2 such that the sum of n+p is from 0 to 3;
A=M; wherein M=H+, $NH_4^+$, $Na^+$ or other pharmaceutically-acceptable inorganic or organic counterion;

Z'=H, OH or OR$_2$, where R$_1$ and R$_2$ fall under the definitions of general Formulae II or III; with the proviso that at least one of Y' and Z' is OR$_1$ or OR$_2$, respectively.

Preferred compounds of Formula Ib include:

D$_1$=O or CH$_2$;

n and p=0, 1, or 2 such that the sum of n+p is from 0 to 3, preferably 1 to 2;

X$_1$ and X$_2$=O;

T$_1$, V, and W=O; or

D$_1$=O or CH$_2$;

X$_1$ and X$_2$=O;

T$_1$ and V=O;

W=S; or

D$_1$=O;

n and p=0 such that the sum of n+p is 0;

V=O;

B' is a purine residue of general Formula IV;

Y' and Z' fall under the definition of general Formula III; or

D$_1$=O or CH$_2$;

p=0, 1, or 2, n=1, such that the sum of n+p is from 1 to 3;

X$_1$=O;

X$_2$=methylene, monochloromethylene, dichloromethylene, monofluoromethylene, difluoromethylene, or imido;

T$_1$, V, and W=O;

Y'=H, OH, or OR$_1$;

Z'=H, OH or OR$_2$, where R$_1$ and R$_2$ fall under the definition of general Formulae II or III; with the proviso that at least one of Y' and Z' is OR$_1$ or OR$_2$, respectively.

Several preferred compounds also are described by Formulae Ia-1 and Ib-1:

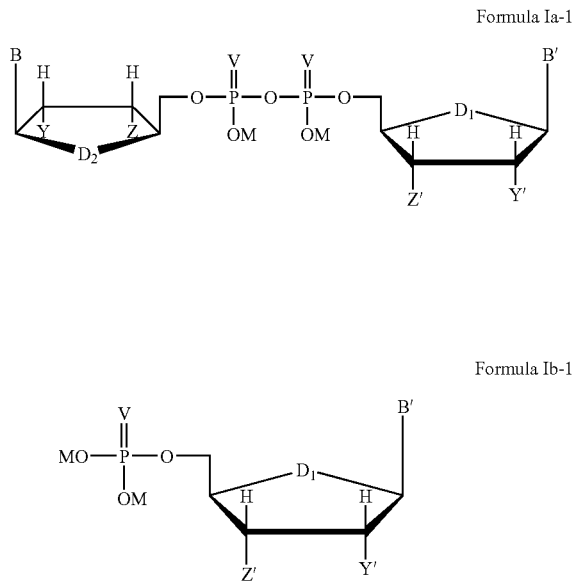

Novel Compounds

Novel compounds of the present invention include compounds of Formula Ia, wherein B and B' are independently pyrimidine (pyrimidine/pyrimidine dinucleotide), provided that when m+n+p=1, R$_{16}$=CH$_3$, and R$_5$ and R$_6$ are taken together as oxygen doubly bonded to C, then R$_7$ is not equal to CH$_3$ (Z' does not equal to acetate); also provided that when m+n+p=3, B and B'=uridine, and R$_5$ and R$_6$ are taken together as oxygen doubly bonded to C, then R$_7$ is not equal to phenyl for Y'=OR$_1$ and/or Y=OR$_4$ (Y and Y' does not equal to benzoyl); further provided that when m+n+p=1, then both R$_8$ and R$_9$ are not CH$_3$ (Z' and Y' taken together do not equal isopropylidine).

Novel compounds of the present invention also include compounds of Formula Ia, wherein B is a purine or residue according to general formula IV, and B' is a pyrimidine residue according to general formula V, (purine/pyrimidine dinucleotide); provided that Y' is not equal to OCH$_3$ when Z', Y, or Y'=H or OH; further provided that R$_8$ is not equal to OCH$_2$CH$_3$ when R$_9$=H (Z' and Y' or Z and Y taken together do not equal to an orthoethylester).

Novel compounds of the present invention also include compounds of Formula Ia, wherein B and B' are independently a purine residue according to general formula IV, (purine/purine dinonucleotide); provided that (a) Y or Y' is not equal to OCH$_3$ when R$_{10}$=NH$_2$ or O; (b) R$_8$ is not equal to OCH$_3$ or OCH$_2$CH$_3$ when R$_9$=H; (c) both R$_8$ and R$_9$ are not equal to CH$_3$; (d) when m+n+p=1, then R$_8$ and R$_9$ does not equal OCH$_2$CH$_3$; (e) when R$_{10}$=NH$_2$, and when R$_5$ and R$_6$ are taken together as oxygen doubly bonded to C, then R$_7$ is not equal to ortho-methylaminophenyl; (f) when m+n+p=1, and when R$_5$ and R$_6$ are taken together as oxygen doubly bonded to C, then R$_7$ is not equal to CH(CH$_2$CH$_2$SCH$_3$)NHS(o-NO$_2$-Ph) or CH(CH$_2$Ph)NHS(o-NO$_2$-Ph).

Novel compounds of the present invention include compounds of Formula Ib (mononucleotide), provided that when n=1, both X$_1$ and X$_2$ are not O; and when n=0, X$_1$ is not O; and provided when Y'=H, that X$_2$ is independently O, CH$_2$, CHF, CHCl, CF$_2$, CCl$_2$; also provided that when R$_{10}$=NH$_2$ or O, and when R$_5$ and R$_6$ are taken together as oxygen doubly bonded to C, then R$_7$ is not equal to ortho-methylamino phenyl; further provided that when n=p=1, X$_2$=CH$_2$ and B'=adenosine, then R$_1$ and R$_2$ are not equal to napththylenylmethyl, napthylenylmethylene, or phenylmethylene.

Novel dinucleoside 5'-diphosphates compounds include compounds of Formula Ia-1:

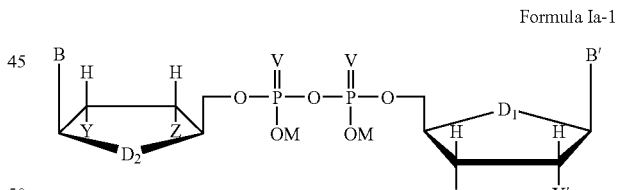

wherein:

V=O;

M=H or a pharmaceutically-acceptable inorganic or organic counterion;

D$_1$ and D$_2$=O;

Y'=H, OH, or OR$_1$;

Z'=H, OH or OR$_2$;

Z=H, OH or OR$_3$;

Y=H, OH, or OR$_4$, where R$_1$, R$_2$, R$_3$ and R$_4$ fall under the definition of general Formulae II or III, provided that at least one of Y', Z', Z and Y is OR$_1$, OR$_2$, OR$_3$, or OR$_4$;

R$_1$, R$_2$, R$_3$, and R$_4$ are residues which are linked directly to the 2' and/or 3' hydroxyls of the furanose via a carbon atom according to Formula II, or, preferably, comprise a moiety linked to the 2' and 3' hydroxyls of the furanose or carbocycle via a common carbon atom according to Formula III,

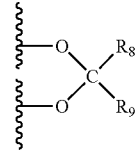

Formula III wherein:

the O atoms are the 2'- and 3'-oxygens of the furanose; and the 2'- and 3'-oxygens of the furanose are linked by a common carbon atom to form a cyclical acetal; and $R_8$ is hydrogen; and $R_9$ is selected from the group consisting of aralkyl, aryl, substituted aralkyl, and substituted in which the aralkyl groups are straight chained from 1 to 5 carbons, with or without unsaturation and without heteroatoms in the alkyl portion, and are monocyclic moieties from 5 to 6 carbons in the aryl portion; and the aryl groups are monocyclic moieties from 4 to 6 carbons, with or without heteroatoms;

B' is a purine residue according to general Formula IV;

wherein $R_{10}$ is acylamino, according to Formula VI;

$R_{17}$ is amino or mono- or disubstituted amino such that the moiety according to Formula VI is a urea;

J=carbon;

$R_{11}$ is absent;

$R_{12}$ is hydrogen; and $R_{13}$ is hydrogen.

Novel mononucleoside 5'-monophosphates compounds include compounds of Formula Ib-1:

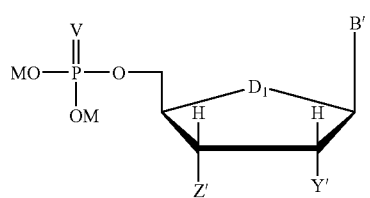

Formula Ib-1 wherein:

V=O;

M=H or a pharmaceutically-acceptable inorganic or organic counterion;

$D_1$=O;

Y'=H, OH, or $OR_1$;

Z'=H, OH, or $OR_2$; with the proviso that at least one of Y' and Z' is $OR_1$ or $OR_2$;

$R_1$ and $R_2$ are residues which are linked directly to the 2' and/or 3' hydroxyls of the furanose via a carbon atom according to Formula II, or both $R_1$ and $R_2$ are linked to the 2' and 3' hydroxyls of the furanose via a common carbon atom according to Formula III,

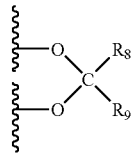

Formula III wherein:

the O atoms are the 2'- and 3'-oxygens of the furanose; and the 2'- and 3'-oxygens of the furanose are linked by a common carbon atom to form a cyclical acetal; and $R_8$ is hydrogen; and $R_9$ is selected from the group consisting of aralkyl, aryl, substituted aralkyl, and substituted aryl;

in which the aralkyl groups are straight chained from 1 to 5 carbons, with or without unsaturation and without heteroatoms in the alkyl portion, and are monocyclic moieties from 5 to 6 carbons in the aryl portion; and the aryl groups are monocyclic moieties from 4 to 6 carbons, with or without heteroatoms;

B' is a purine residue according to general Formula IV, wherein $R_{10}$ is acylamino, according to Formula VI; and $R_{17}$ is amino or mono- or disubstituted amino such that the moiety according to Formula VI is a urea;

J=carbon;

$R_{11}$ is absent;

$R_{12}$ is hydrogen; and $R_{13}$ is hydrogen.

The compounds of the present invention fall under the definition of general Formula I, which is further divided into general Formulae Ia (dinucleotides), Ib (mononucleotides), Ia-1 (dinucleoside diphosphates) and Ib-1 (mononucleoside monophosphates). While potent and selective $P2Y_{12}$ antagonists can be found within any of these subdivisions, mononucleotides have an advantage over dinucleotides in terms of ease of synthesis and cost. In general, mononucleoside diphosphates and mononucleoside triphosphates falling under general Formula Ib are more potent antagonists at $P2Y_{12}$ than the corresponding mononucleoside monophosphates of Formula Ib-1. However, nucleoside 5'-monophosphates and their analogues are easier to prepare and have greater chemical and biological stability comparing with mononucleoside diphosphates and mononucleoside triphosphates. Thus, for synthetic reasons, a nucleoside 5'-monophosphate with appropriate druglike properties is sometimes more advantageous than other mononucleotides bearing more than one phosphate, or related dinucleotides. For dinucleotides falling under general formula Ia, those having only two phosphates as described by formula Ia-1 are most desireable, as they can be prepared under simple reaction conditions in good yield from the corresponding mononucleoside 5'-monophosphates falling under formula Ib-1. When attacked by enzymes in the bloodstream, nucleoside 5'-monophosphate only gives one byproduct from loss of the phosphate. Dinucleoside diphosphates are the easiest dinucleotides to make; they are stable, and give a limited number of breakdown products, in contrase to dinucleotides with longer phosphate chain lengths. For inhibition of platelet aggregation, nucleoside 5'-monophosphate and dinucleoside diphosphates are preferred compounds.

Two modifications can be made to compounds of general Formulas Ia-1 and Ib-1 to render them potent antagonists of the platelet $P2Y_{12}$ receptor. In general, a preferred starting material of nucleoside 5'-monophosphate is adenosine 5'-monophosphate (AMP), or an AMP derivative, as it contains the appropriate functional groups for the desired modifications and gives rise to more potent and selective antagonists compared to similar modifications of other commonly available nucleotide monophosphates. The first modification is to install an aryl or aralkyl acetal bridging the 2'- and 3'-hydroxyls of the ribose, with the nature of the aryl or aralkyl group as previously described. Of these described groups, the most preferred are phenyl, benzyl, and styryl, which are the acetals arising from the reaction between the 2' and 3' hydroxyl groups of the ribose and benzaldehyde, phenylacetaldehyde, and cinnamaldehyde, respectively. These moieties provide several important advantages over many similar modifications. Firstly, they are derived from readily available, low cost aldehydes or aldehyde equivalents (for example, aldehyde, dialkyl acetals). Secondly, these moieties allow the synthesis of either of the two possible diastereomers that arise from the addition of the acetal to the chiral ribose residue, via several synthetic strategies. Finally, molecules bearing these acetal moieties provide for potent analogues of the present invention.

The second modification is to add an aminocarbonyl or substituted aminocarbonyl group to the 6-amino position of the adenine base, resulting in a urea moiety at that position. Substituents on the urea moiety fall under the definition of the amino substituents of $R_{17}$, i.e., alkyl, cycloakly, aralkyl, or aryl, with or without substituents, unsaturation, or heteroatoms. These urea substituents can be broadly categorized as either aromatic or aliphatic in nature. A preferred substituent chosen from aryl groups is phenyl. When the urea group is an aliphatic urea, a preferred substituent on nitrogen is a linear, branched, or cyclic, $C_1$-$C_6$ alkyl; with or without unsaturation. Preferred urea moieties are linear alkyl ureas from 2 to 6 carbons inclusively, or cyclic alkyl ureas having 3 to 6 carbons in the ring. More preferred urea moieties are linear alkyl ureas containing from 2 to 4 carbons inclusively in the chain or cycloalkyl ureas having from 3 to 5 carbons inclusively in the ring.

Novel compounds having the above modifications can be shown in general as formulae Ia-2 and Ib-2.

wherein:

$R_{18}$ and $R_{18'}$ are independently phenyl, benzyl, or styryl; and $R_{19}$ and $R_{19'}$ are independently $C_2$ to $C_6$ alkyl; $C_3$ to $C_6$ cycloalkyl; alkylcycloalkyl with one to two carbon atoms in the alkyl portion, and three to six carbons in the cycloalkyl portion; phenyl; substituted or unsubstituted.

For example, $R_{19}$ and $R_{19'}$, are independently ethyl, propyl, butyl, cyclopropyl, cyclopropylmethyl, cyclobutyl, cyclopentyl, or phenyl.

While $R_{18}$ and $R_{18'}$, and $R_{19}$ and $R_{19'}$ can be independently a given group, they are preferably identical pairs for practical synthetic reasons.

Formula Ib-2

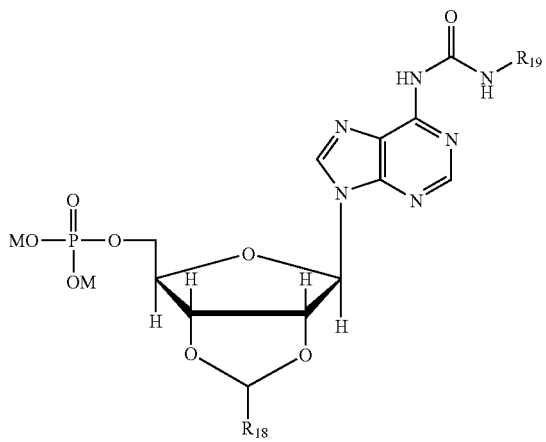

wherein:

$R_{18}$ is phenyl (benzaldehyde acetal), benzyl (phenylacetaldehyde acetal) or styryl (cinnamyl acetal);

Formula Ia-2

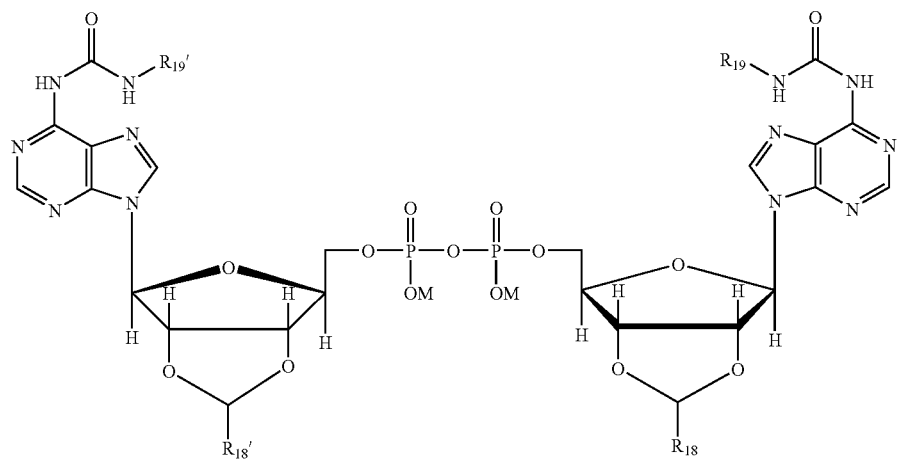

$R_{19}$ is $C_2$ to $C_6$ alkyl, $C_3$ to $C_6$ cycloalkyl, alkylcycloalkyl with one to two carbon atoms in the alkyl portion, and three to six carbons the cycloalkyl portion, phenyl, substituted or unsubstituted.

For example, $R_{19}$ is ethyl, propyl, butyl, cyclopropyl, cyclopropylmethyl, cyclobutyl, cyclopentyl, or phenyl.

An aspect of the present invention is that, while any of Formula I compounds is capable of antagonism of ADP-induced platelet aggregation, it is the combination of both 2'/3' and 6-N modifications in the same molecule that renders a highly potent and selective $P2Y_{12}$ antagonist compound.

Another aspect of the present invention is the effect of compound structure on the resultant potency in washed platelets versus potency in whole blood. In general, the potency of a given compound is lower in whole blood versus washed platelets, ostensibly the result of increased binding of the compound to the higher levels of blood proteins in the former. This property is particularly acute for nucleoside 5'-monophosphates versus the corresponding di- and triphosphates, since there are fewer ionizable groups available in the former to offset the lipophilic acetal and urea groups, which presumably increase protein binding in whole blood. Unexpectedly, we found that compounds having aliphatic ureas gave comparable results when tested in whole blood and washed platelet assays. Furthermore, we found that compounds with aliphatic ureas were more potent than their aromatic counterparts in washed platelets.

Novel compounds of the present invention include 2'- or 3'-phenylcarbamate UTP, 2',3'-di-phenylcarbamate UTP, 2',3'-phenylacetaldehyde acetal ADP, di[3'(phenylcarbamate) dUp2dU], 2',3'-phenylacetaldehyde acetal Up3U, di 2',3'-phenylacetaldehyde acetal Up3U, 2',3'-phenylacetaldehyde acetal Up4A, 2',3'-phenylacetaldehyde acetal Ap4U, di 2',3'-phenylacetaldehyde acetal Ap4U, 2',3'-phenylacetaldehyde acetal Ip4U, 2',3'-phenylacetaldehyde acetal Up4U, 2',3'-phenylacetaldehyde acetal Ip4U, 2',3'-phenylacetaldehyde acetal Up4dC, tetraphenylcarbamate Up4U, di2',3'-benzaldehyde acetal Ip4U, di 2',3'-benzaldehyde acetal Up4U, 2',3'-benzaldehyde acetal Up4U, di 2',3'-phenylacetaldehyde acetal Cp4U, 2',3'-phenylacetaldehyde acetal Cp4U, 2',3'-phenylacetaldehyde acetal Up4C, 2',3'-phenylacetaldehyde acetal Up4T, di 2',3'-benzaldehyde acetal Cp4U, 2',3'-benzaldehyde acetal Ip4U, 2',3'-benzaldehyde acetal Up4U, 2',3'-benzaldehyde acetal Up4dC, 2',3'-benzaldehyde acetal Cp4U, 2',3'-benzaldehyde acetal Up4C, 2',3'-phenylpropionaldehyde acetal Up4U, di 2',3'-phenylpropionaldehyde acetal Up4U, 2',3'-benzaldehyde acetal Cp4C, bis MANT Up4U, Mant Up4U, di 2',3'-benzylacetal Up4U, mono 2',3'-benzylacetal Up4U, triphenyl carbamate Up4U, 2',3'-phenylcarbamate Up4U, and monophenylcarbamate Up4U.

Novel dinucleoside 5'-diphosphate compounds include $P^1$, $P^2$-di-(2',3'-cinnamyl acetal-6-N-ethylurea adenosine 5'-) diphosphate (compound 44), $P^1$, $p^2$-di-(2',3'-phenylpropargyl acetal-6-N-ethylurea adenosine 5'-) diphosphate (compound 45), $P^1$, $P^1$-di-(2',3'-phenylacetaldehyde acetal-6-N-ethylurea adenosine 5'-) diphosphate (compound 46), and $P^1$, $P^2$-di-(2',3'-phenyl acetal-6-N-ethylurea adenosine 5'-) diphosphate (compound 47). Diastereomerically-pure dinucleoside diphosphates include $P^1$, P4-di-trans-(2',3'-cinnamyl acetal-6-N-ethylurea adenosine 5'-) diphosphate (compound 48), $P^1$, $P^4$-di-trans-(2',3'-phenyl acetal-6-N-ethylurea adenosine 5'-) diphosphate (compound 49), and $P^1$, $P^4$-di-trans-(2',3'-phenylpropargyl acetal-6-N-ethylurea adenosine 5'-) diphosphate (compound 50).

Novel mononucleoside 5'-monophosphate compounds include 2',3'-phenylacetaldehyde acetal-6-N-phenylurea AMP (compound 22), 2',3'-phenylacetaldehyde acetal-6-N-n-hexylurea AMP (compound 23), 2',3'-phenylacetaldehyde acetal-6-N-ethylurea AMP (compound 24), 2',3'-phenylacetaldehyde acetal-6-N-cyclopentylurea AMP (compound 25), 2',3'-cinnamyl acetal-6-N-n-hexylurea AMP (compound 26), 2',3'-cinnamyl acetal-6-N-ethylurea AMP (compound 27), 2',3'-cinnamyl acetal-6-N-phenylurea AMP (compound 28), 2',3'-cinnamyl acetal-6-N-n-propylurea AMP (compound 29), 2',3'-cinnamyl acetal-6-N-n-butylurea AMP (compound 30), 2',3'-phenylpropargyl acetal-6-N-phenylurea AMP (compound 31), 2',3'-phenylpropargyl acetal-6-N-n-hexylurea AMP (compound 32), 2',3'-phenylpropargyl acetal-6-N-n-butylurea AMP (compound 33), 2',3'-phenylpropargyl acetal-6-N-n-propylurea AMP (compound 34), 2',3'-phenylpropargyl acetal-6-N-ethylurea AMP (compound 35), 2',3'-benzaldehyde acetal-6-N-ethylurea AMP (compound 36), 2',3'-benzaldehyde acetal-6-N-n-propylurea AMP (compound 37), 2',3'-benzaldehyde acetal-6-N-n-butylurea AMP (compound 38), 2',3'-benzaldehyde acetal-6-N-n-hexylurea AMP (compound 39), 2',3'-benzaldehyde acetal-6-N-cyclopentylurea AMP (compound 40), 2'3'-(trans)cinnamyl acetal-6-N-ethylurea AMP(compound 41), 2'3'-(trans)phenyl acetal-6-N-ethylurea AMP (compound 42), and 2'3'-(cis)phenyl acetal-6-N-ethylurea AMP (compound 43). In Compounds 41-43, cis or trans refers to the relative position of hydrogen atoms on the dioxole ring.

More preferred mononucleoside monophosphates of the present invention include 2', 3'-cinnamyl acetal-6-N-n-hexylurea AMP (compound 26), 2',3'-cinnamyl acetal-6-N-ethylurea AMP (compound 27), 2',3'-benzaldehyde acetal-6-N-ethylurea AMP (compound 36), 2'3'-(trans)cinnamyl acetal-6-N-ethylurea AMP (compound 41), 2'3'-(trans)phenyl acetal-6-N-ethylurea AMP (compound 42), and 2'3'-(cis)phenyl acetal-6-N-ethylurea AMP (compound 43). More preferred dinucleoside diphosphates include $P^1$, $P^4$-di-trans-(2', 3'-cinnamyl acetal-6-N-ethylurea adenosine 5'-) diphosphate (compound 48), $P^1$, $P^4$-di-trans-(2',3'-phenyl acetal-6-N-ethylurea adenosine 5'-) diphosphate (compound 49), and $P^1$, $P^4$-di-trans-(2',3'-phenylpropargyl acetal-6-N-ethylurea adenosine 5'-) diphosphate (compound 50).

The structures of the novel Compounds 1-50 are shown as follows. In the following structures, hydrogens that are understood to be present have been omitted for the sake of simplicity. Tautomers drawn represent all tautomers possible. As diastereomers are generated with the introduction of the acetal group, structures containing this moiety without the stereochemistry explicitly defined (Compounds 1-20 and 23-26) are taken to mean either of the possible diastereomers alone or a mixture of diasteromers in any ratio.

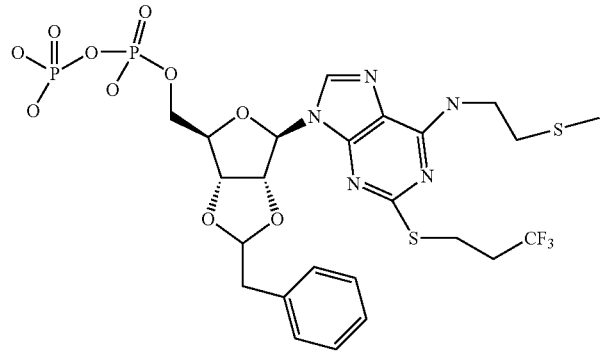
Compound 1
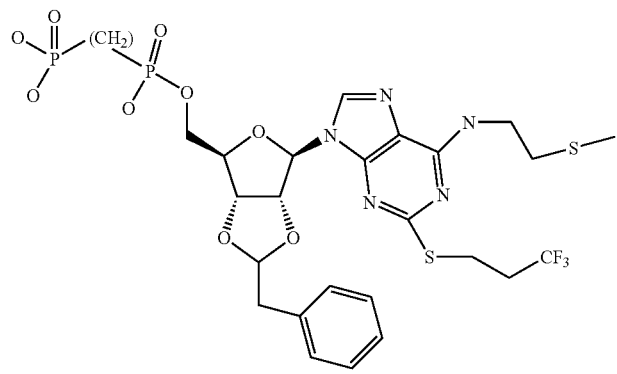
Compound 2
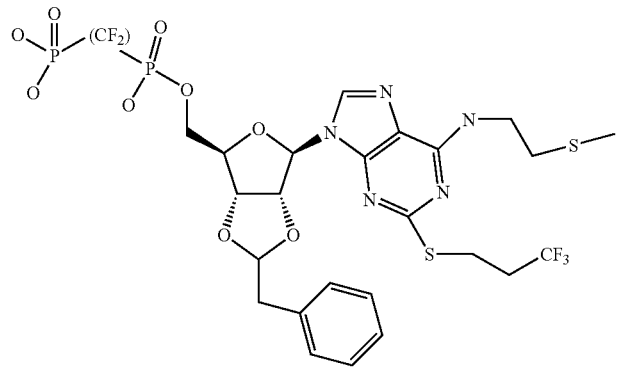
Compound 3
2-(3-trifluoromethylpropyl)thio-6-(2-methylthio) ethylamino-2', 3'-(benzyl)methylenedioxy purine riboside 5'-α, β-difluoromethylene diphosphate
Compound 4
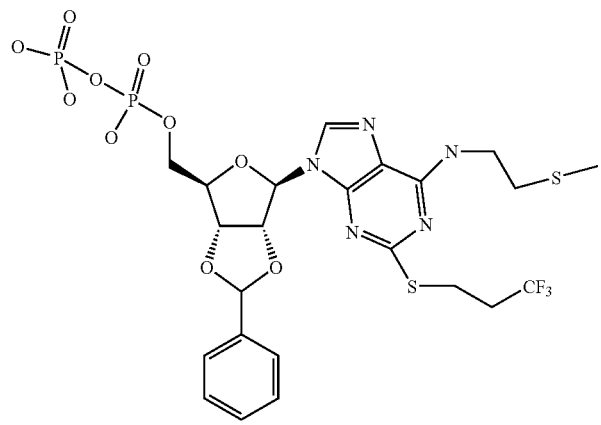

-continued
Compound 5
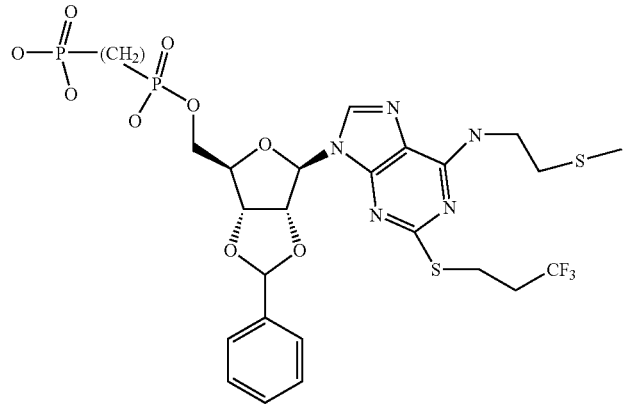
Compound 6
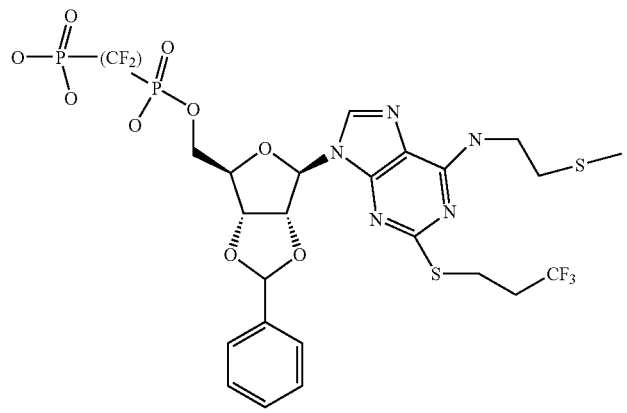
Compound 7
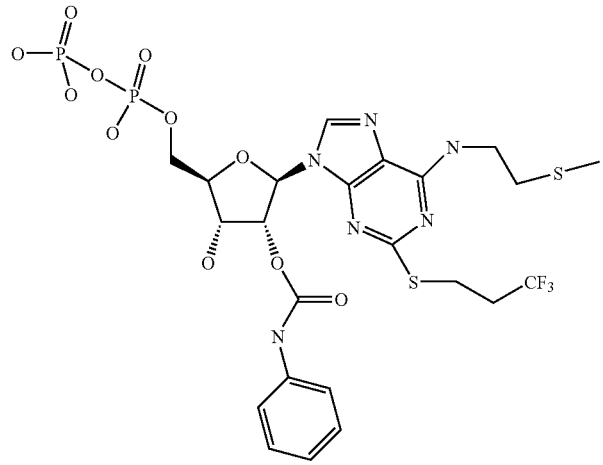

-continued
Compound 8
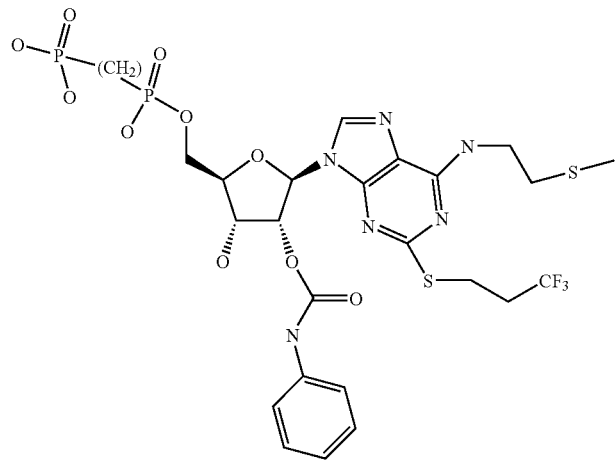
Compound 9
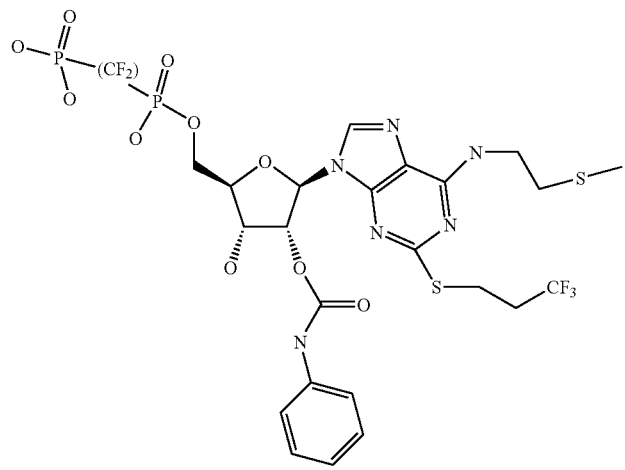
Compound 10
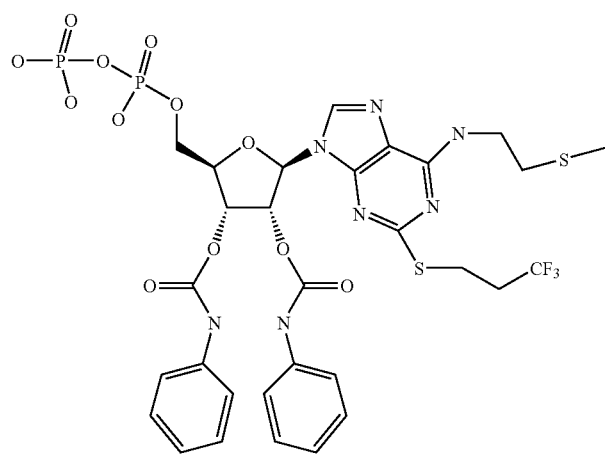

-continued
Compound 11
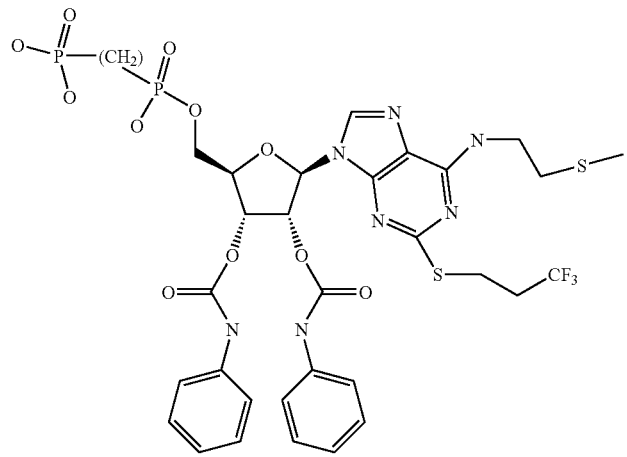
Compound 12
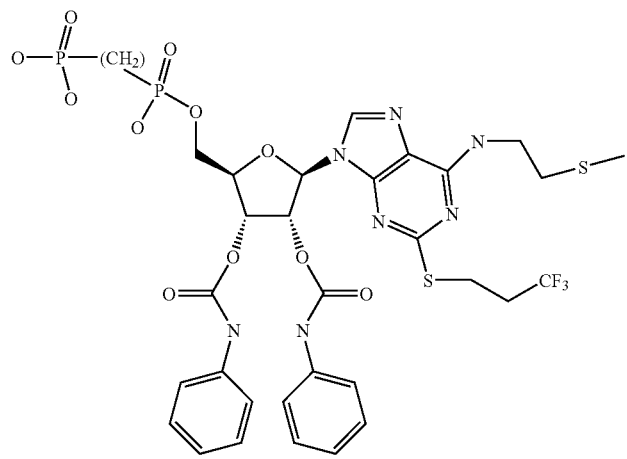
Compound 13
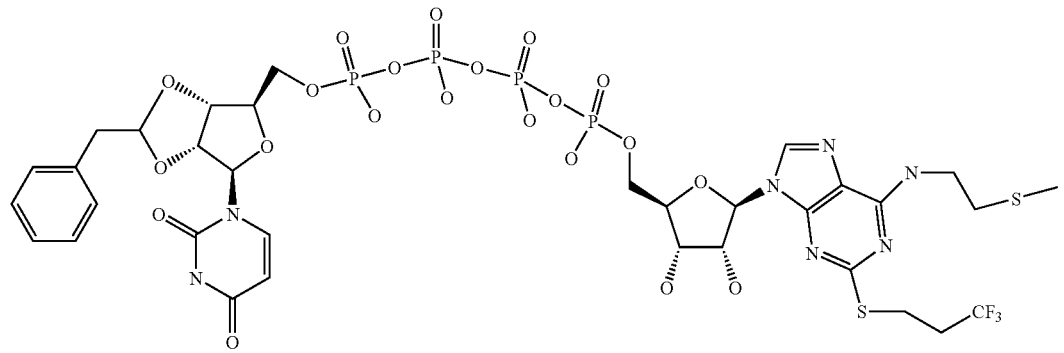

-continued
Compound 14
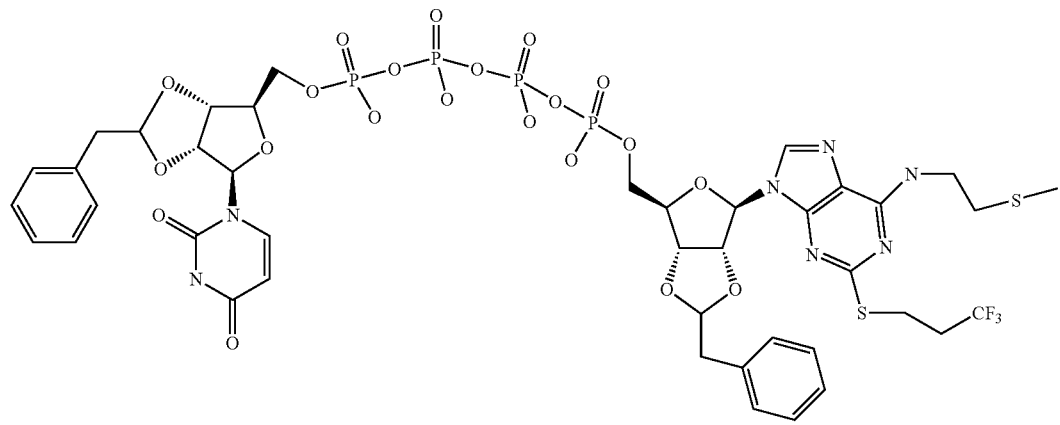
P$^1$-[2-(3-trifluoromethylpropyl)thio-6-(2-methylthio)ethylamino 2′, 3′-(benzyl)methylene
dioxy purine riboside]-P$^4$-(2′, 3′-(benzyl)methylene dioxy uridine) tetraphosphate
Compound 15
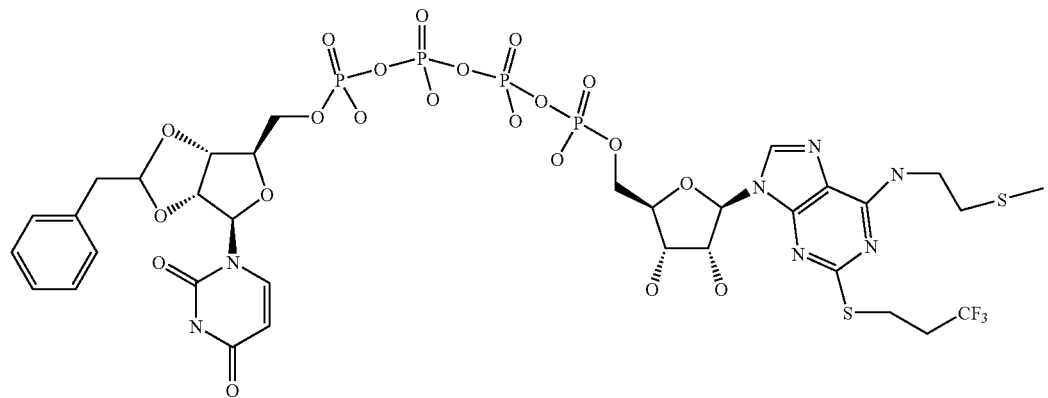
Compound 16
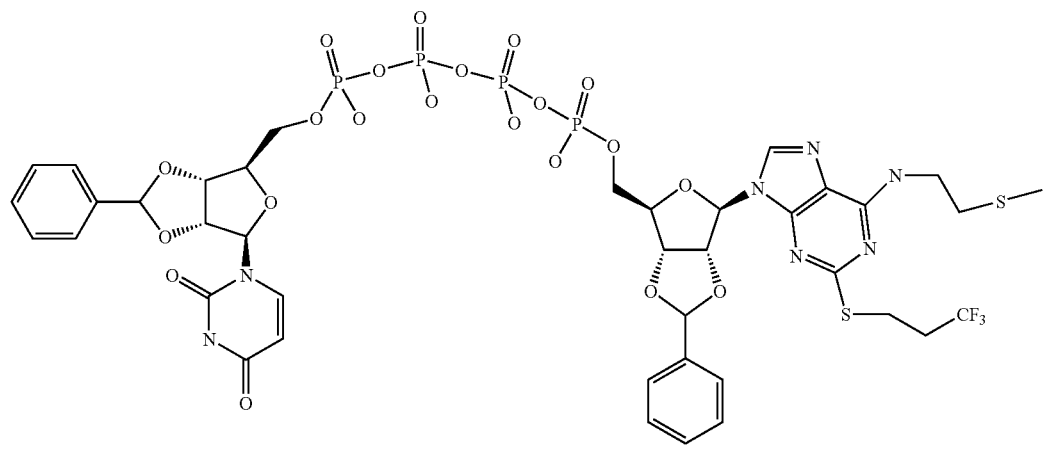

-continued
Compound 17
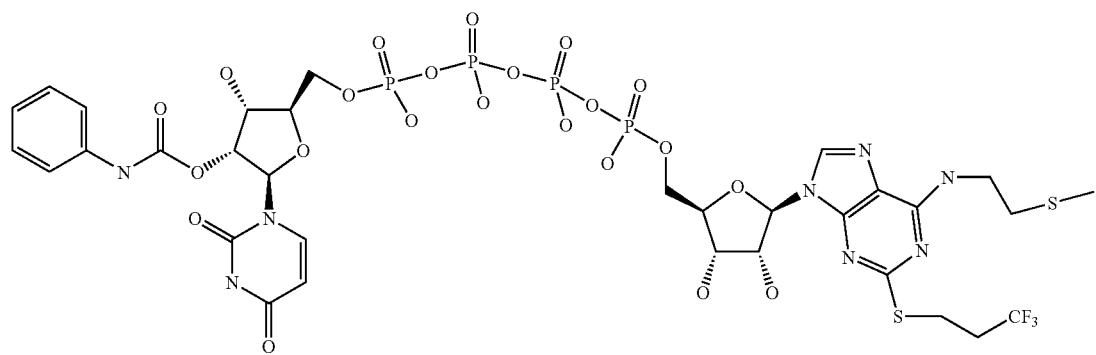
Compound 18
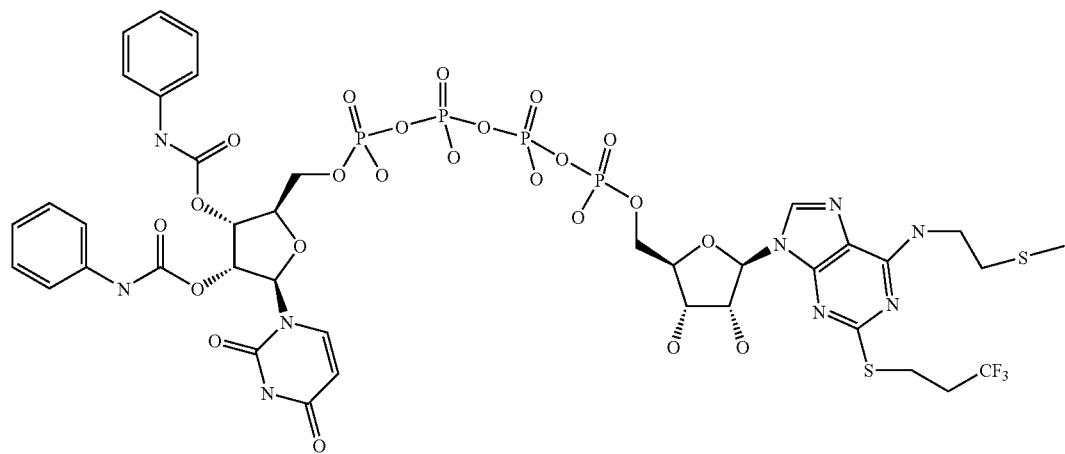
Compound 19
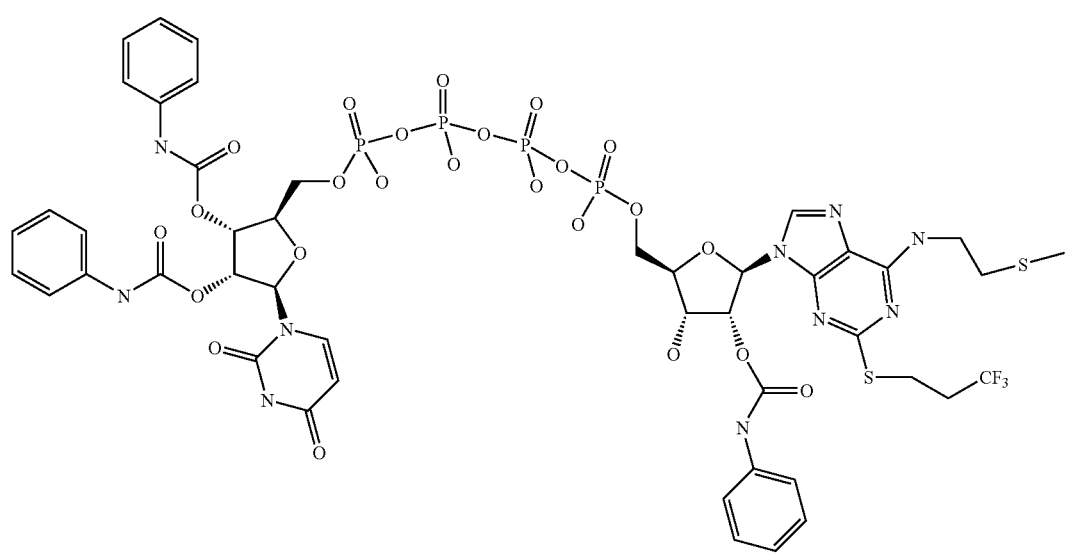

Compound 20
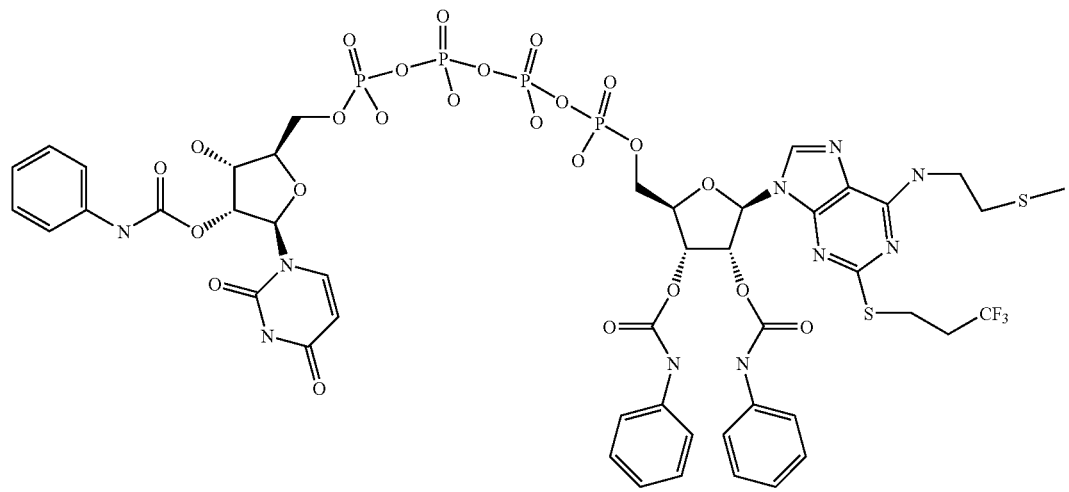
Compound 21
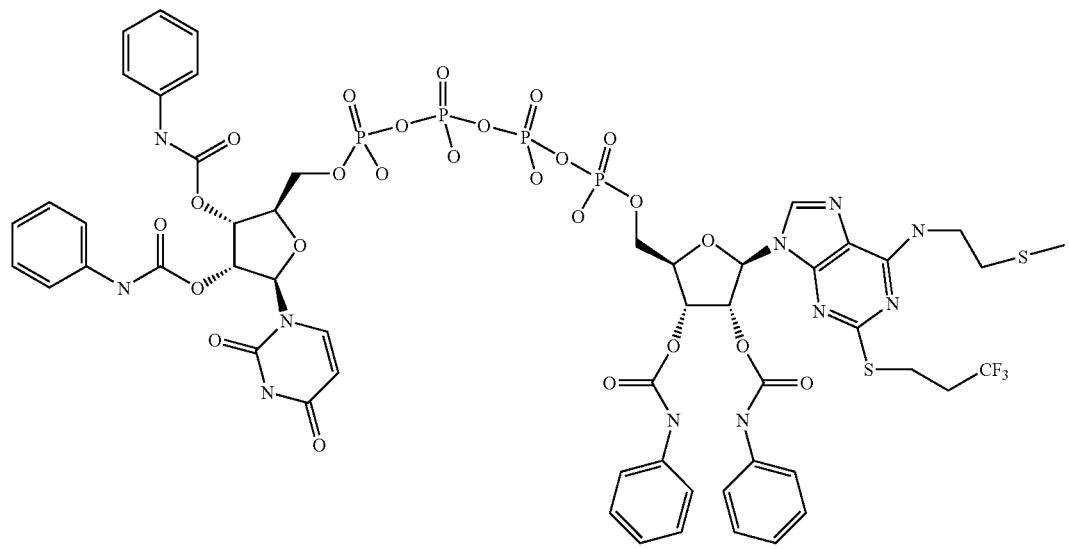
Compound 22
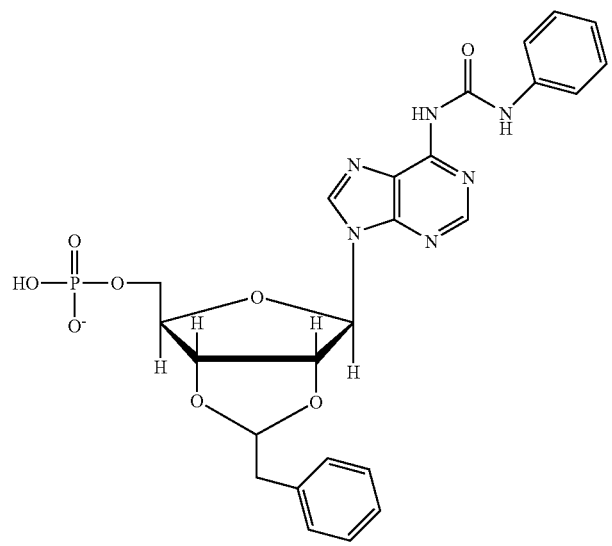

-continued
Compound 23
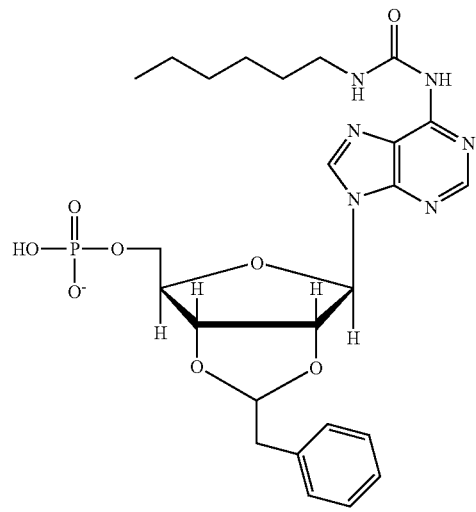
Compound 24
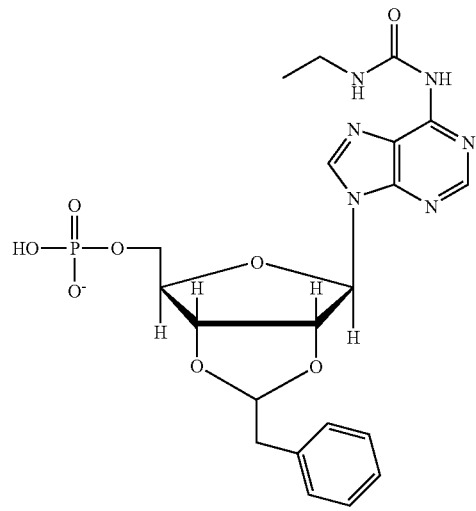
Compound 25
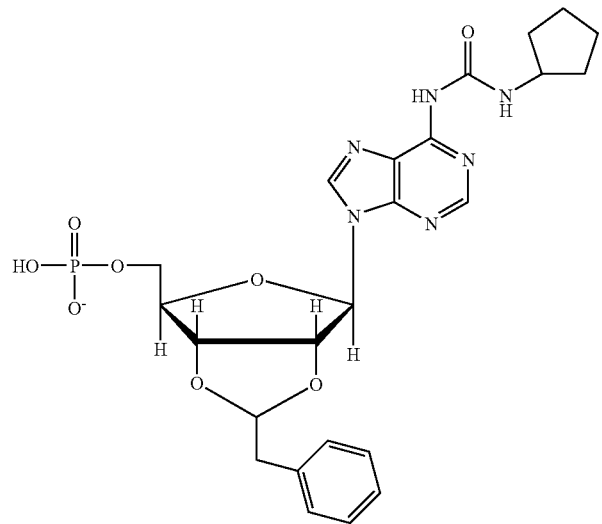

-continued
Compound 26
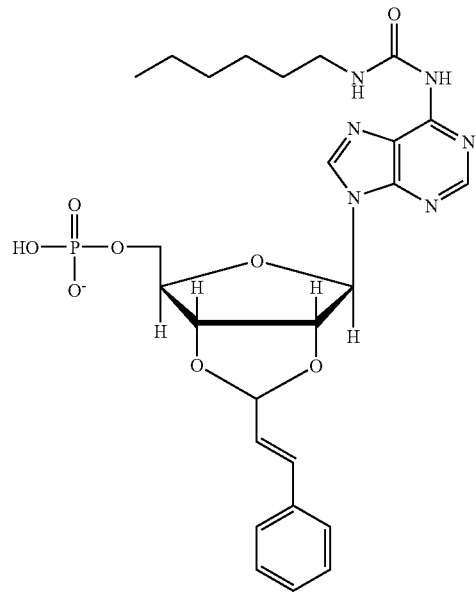
Compound 27
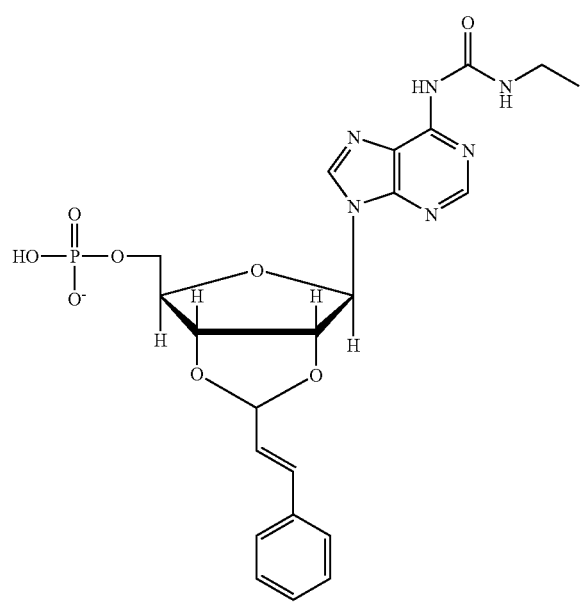

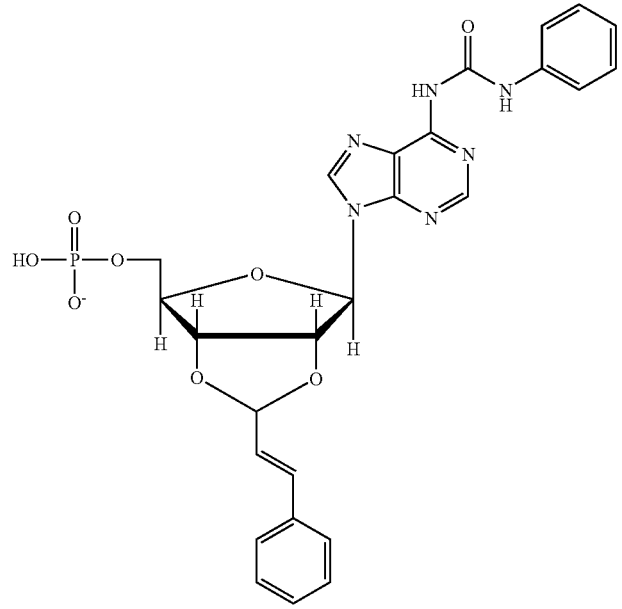
Compound 28
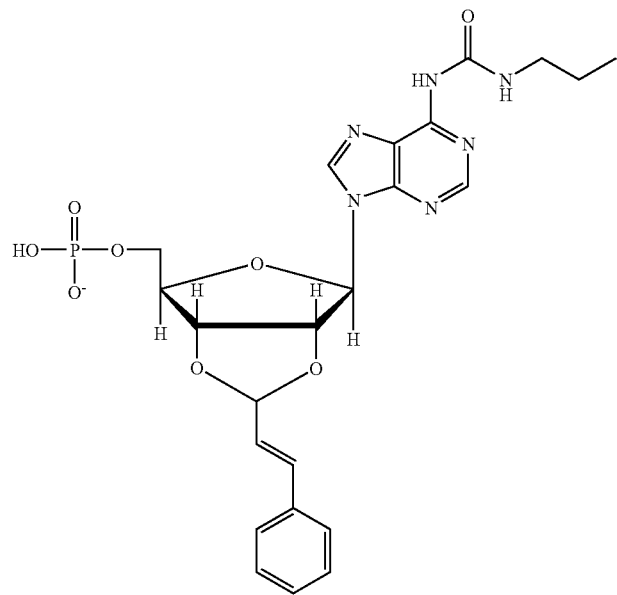
Compound 29

-continued
Compound 30
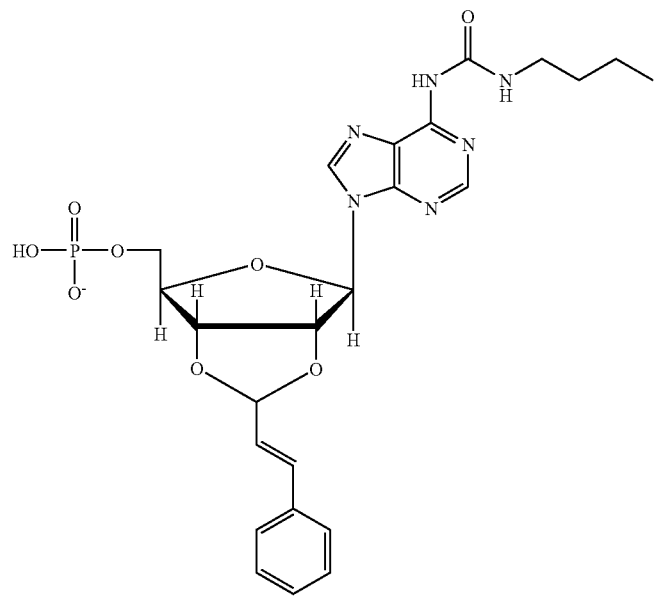
Compound 31
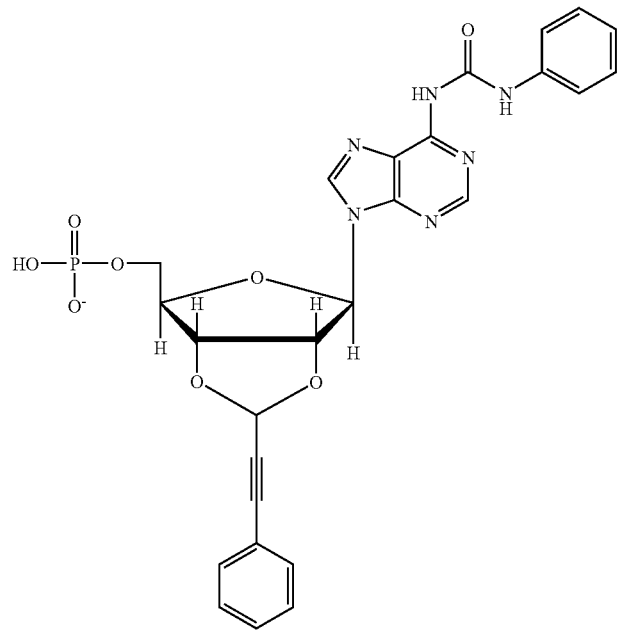

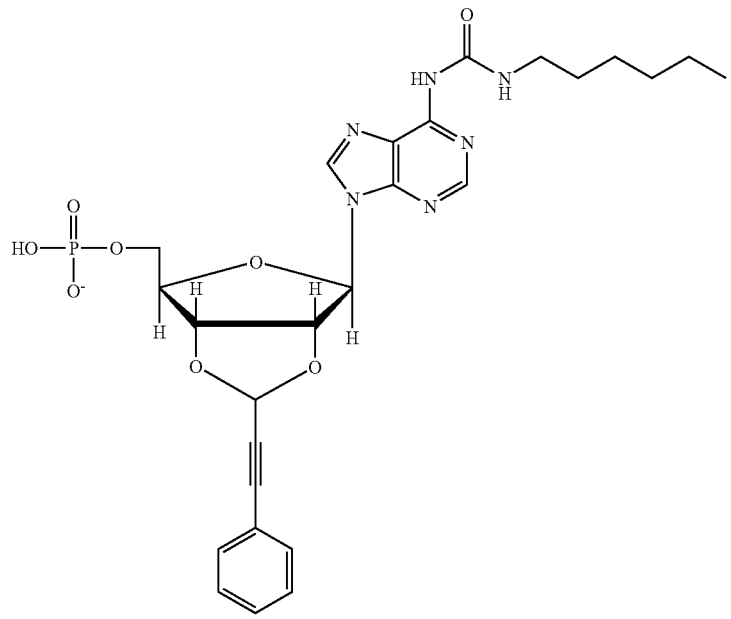
Compound 32
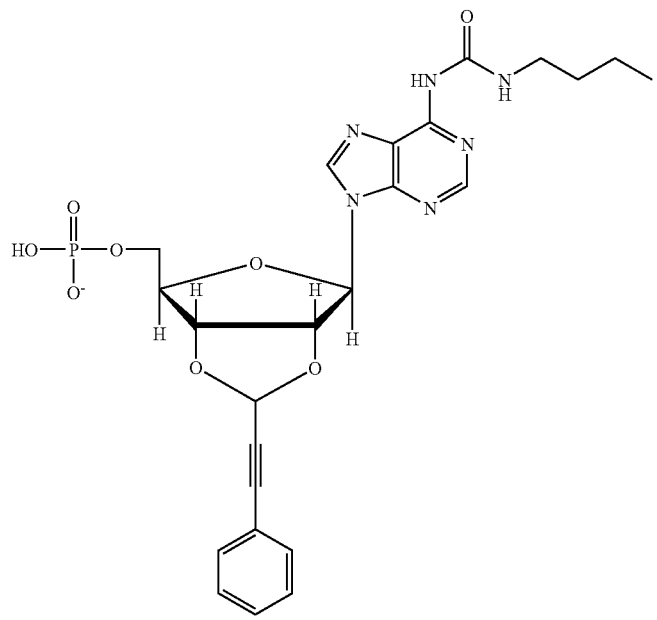
Compound 33

-continued
Compound 34
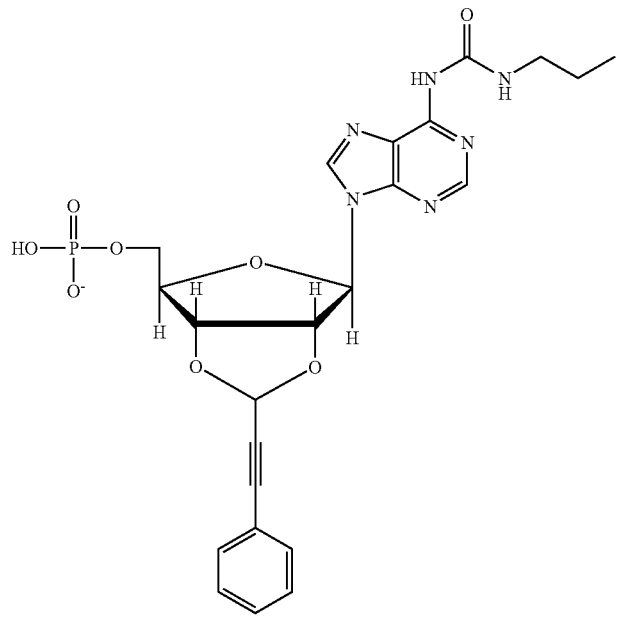
Compound 35
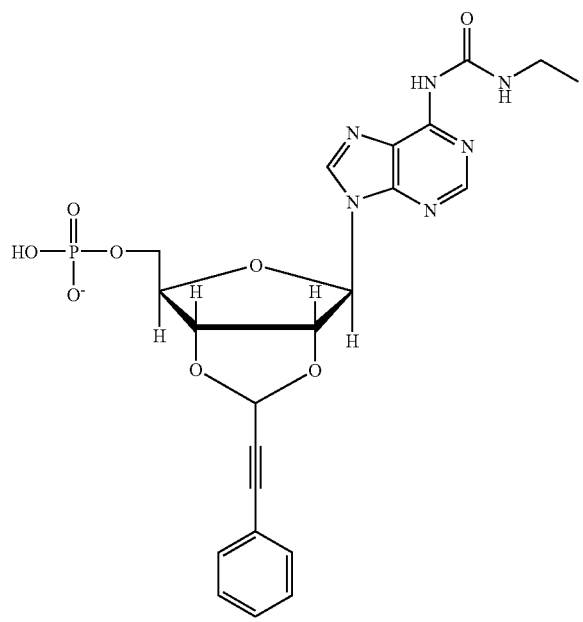

-continued
Compound 36
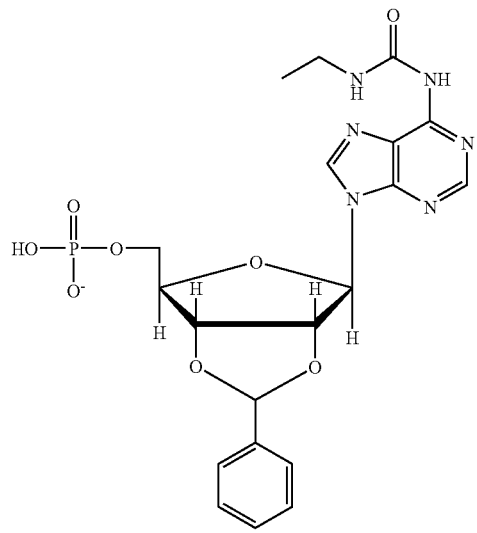
Compound 37
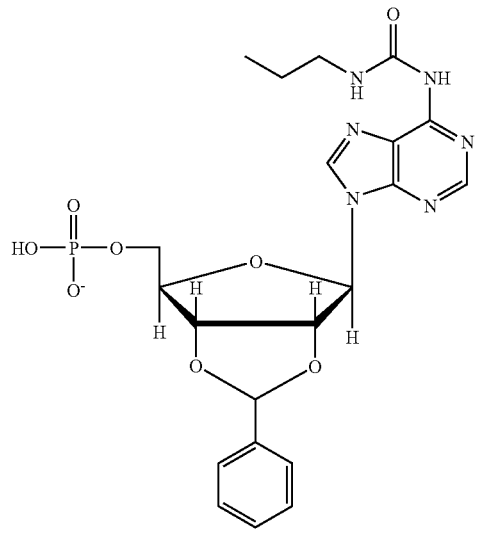
Compound 38
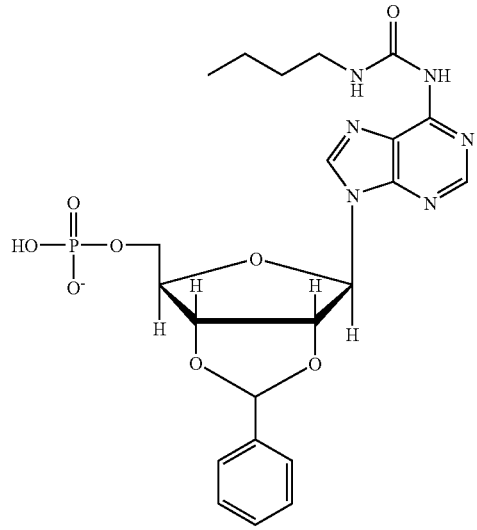

-continued
Compound 39
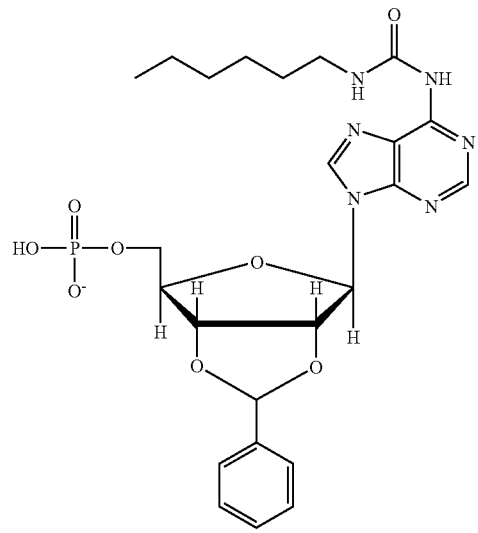
Compound 40
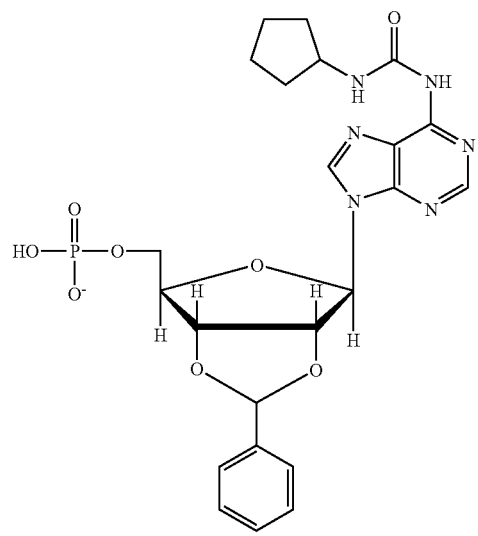

-continued
Compound 41
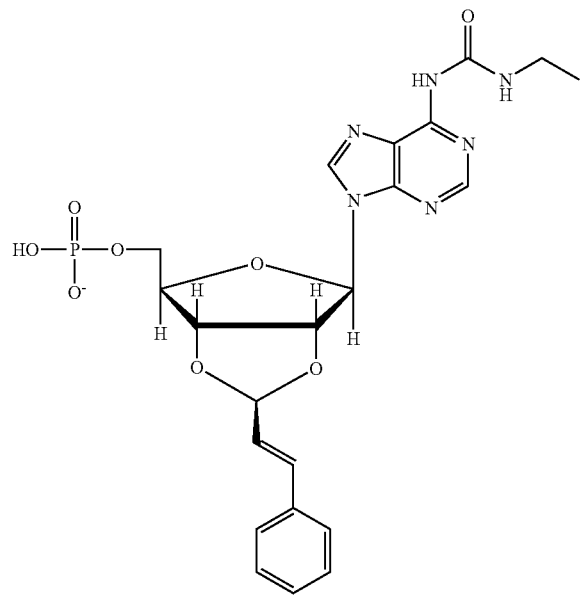
Compound 42
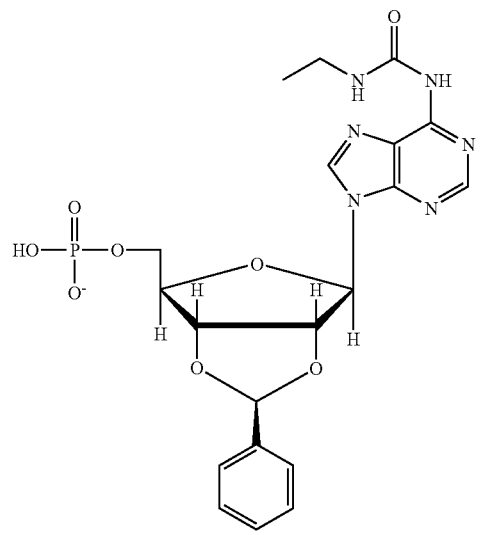

-continued
Compound 43
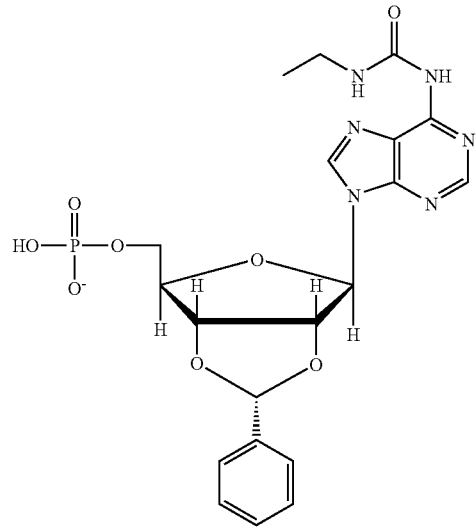
Compound 44
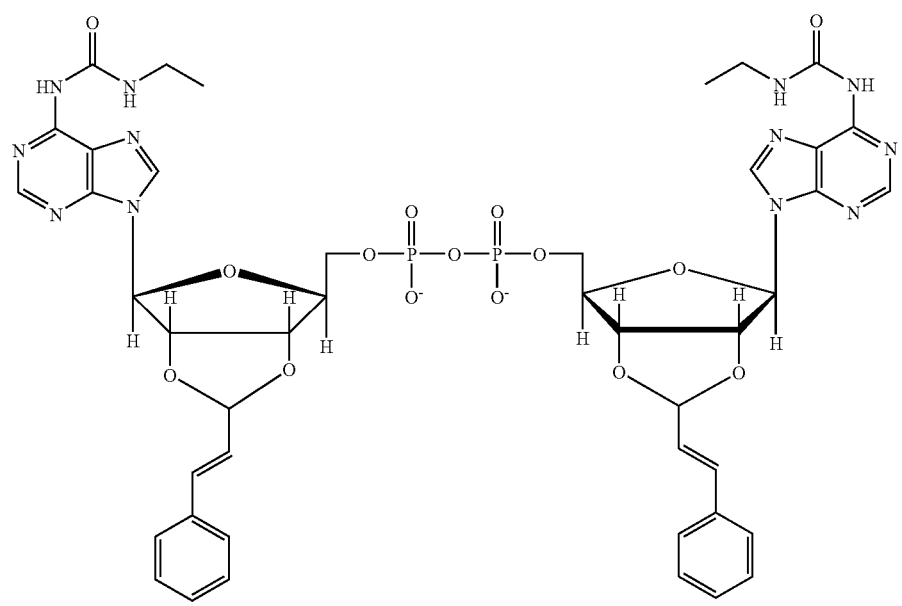

-continued
Compound 45
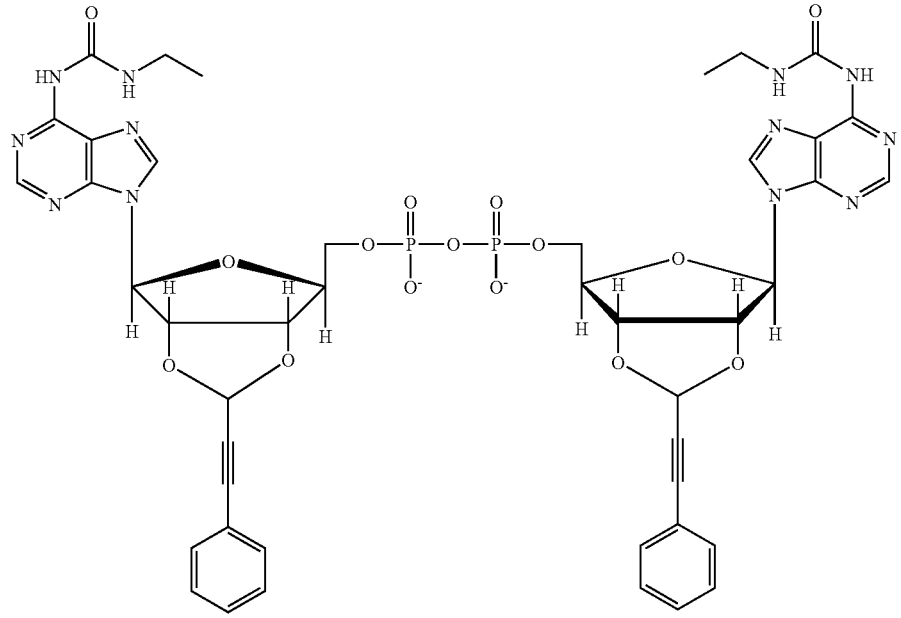
Compound 46
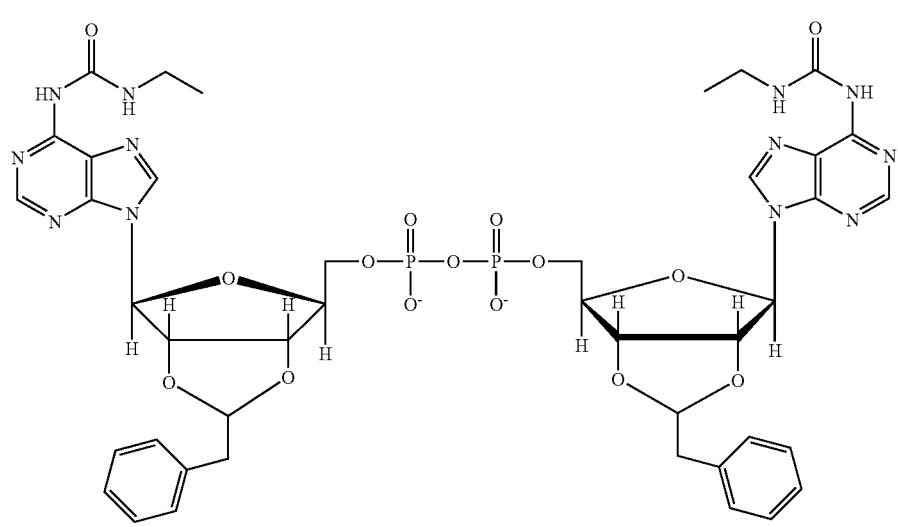

-continued
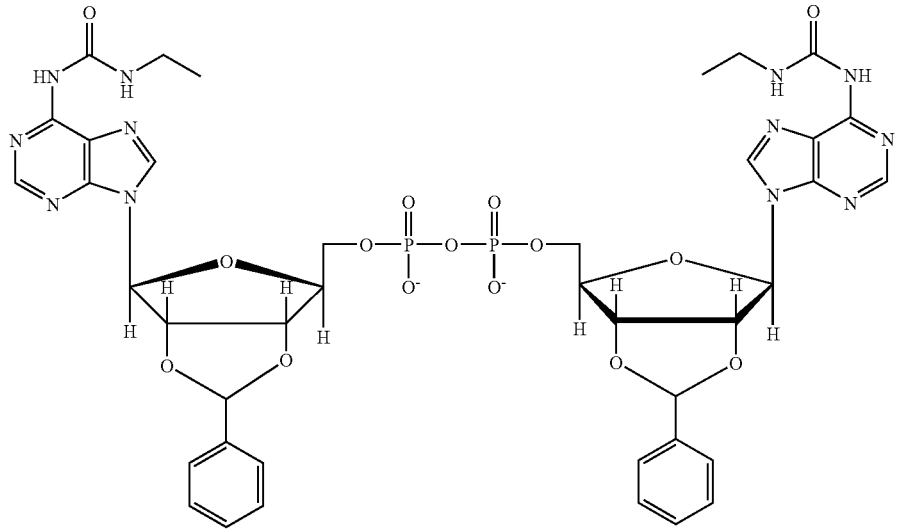
Compound 47
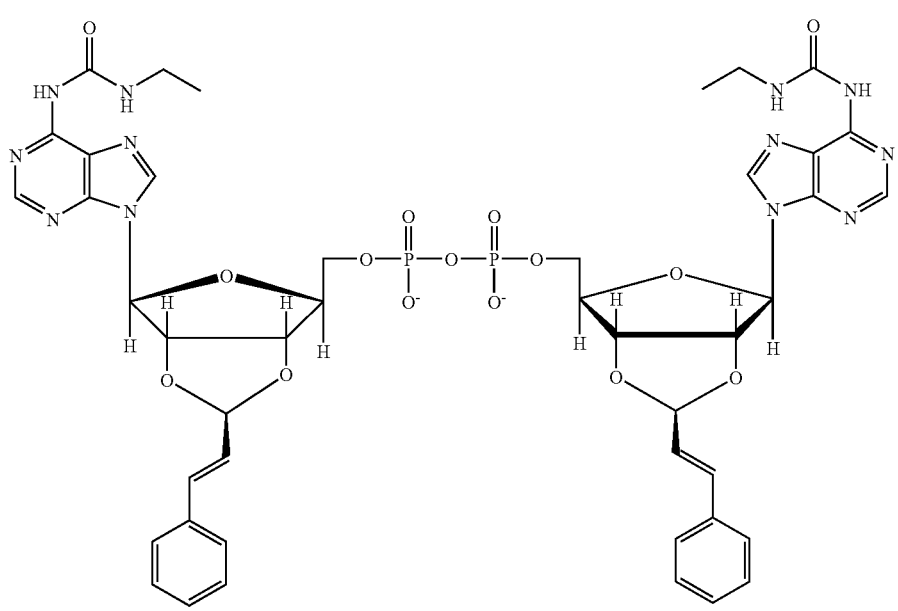
Compound 48

-continued

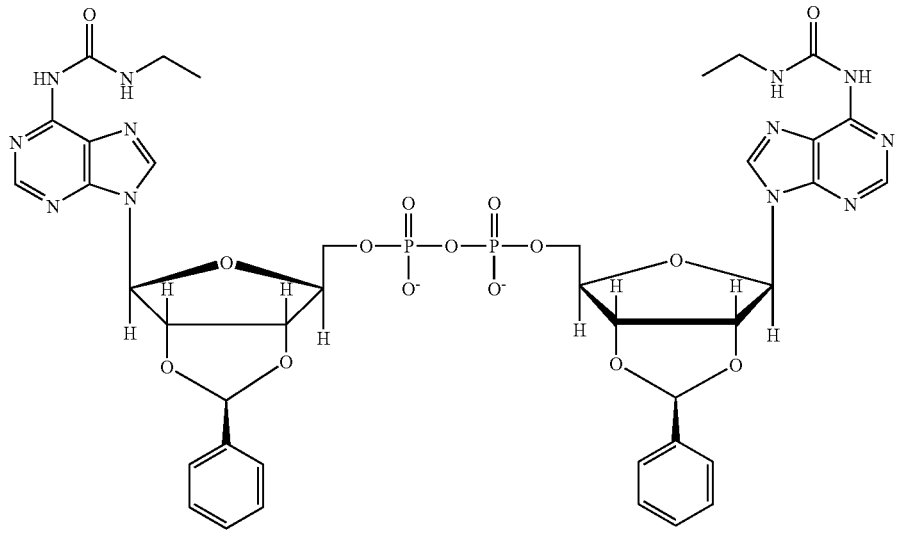

Compound 49

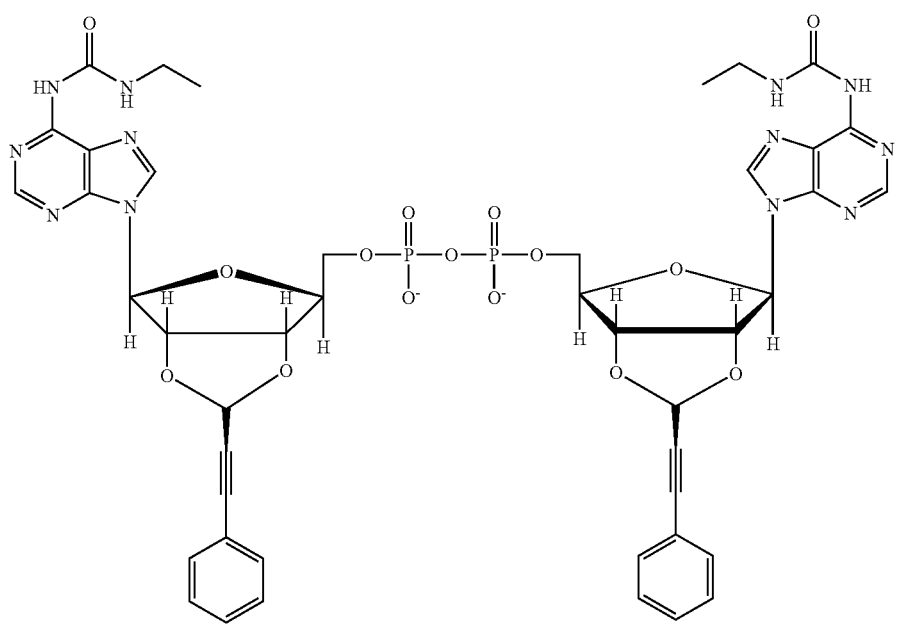

Compound 50

Pharmaceutical Formulations

The present invention additionally provides novel pharmaceutical formulations comprising compounds of Formula I, Ia, Ib, Ia-1, Ib-1, Ia-2, or Ib-2, or a pharmaceutically acceptable salt, solvate, or hydrate thereof, and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicy modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation of the present invention provides an aqueous solution comprising water, suitable ionic or non-ionic tonicity modifiers, suitable buffering agents, chelating agent, pH adjusters, and a compound of Formula I, Ia, Ib, Ia-1, Ib-1, Ia-2, or Ib-2 at 0.005 to 3% w/v, wherein said aqueous solution has a tonicity of 200-400 mOsm/kG and a pH of 4-9. In a preferred embodiment, the pharmaceutical formulation comprises 0.025-3, 0.05 to 2.5% or 0.01 to 1.5% w/v of a compound of Formula I, Ia, Ib, Ia-1, Ib-1, Ia-2, or Ib-2. In another preferred embodiment, the pharmaceutical formulation has the tonicity of 220-360 or 250-350 mOsm/kG. In another preferred embodiment, the pharmaceutical formulation has a pH of 4.5-8.5 or 5.5-7.5. In yet another preferred embodiment, the chelating agent in the amount of 0.005-0.01% w/v; preferably 0.008-0.01% w/v.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to intravenous administration.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 3.5-5%, and more preferably 4.2-5% w/v. Mannitol and dextrose are preferred over other possible non-ionic tonicity modifiers such as, propylene glycol and related glycols, polyethylene glycol of varying molecular ranges, sorbitol, polymers such as polyvinyl alcohol, PVP, sorbitol, sucrose, and trehalose, because most of these non-ionic tonicity modifiers are not suitable for long-term administration via the intravenous route. For example, sucrose and trehalose are not metabolized when given via the intravenous route and are excreted unchanged, thus, they are not candidates for an intravenous dosage form. In addition, the formulation containing mannitol has the advantages of being adaptable for freeze-drying or lyophilization.

In one embodiment, the pharmaceutical formulation comprises 0.5-0.9% ionic tonicity modifier such as sodium chloride; the formulation optionally contains additional buffering agents (such as sodium phosphates and/or sodium citrate) within a range of 0.01-0.2% w/v, a chelating agent in a range of 0.005-0.01% w/v, and pH adjusters. Such an aqueous composition has a tonicity of 250-350 mOsm/kG and is formulated at a physiologically acceptable pH. However, depending on the compound type and concentration, this NaCl formulation tends to form a precipitate at higher concentration (>0.1% w/v) of some compounds.

Nucleoside compounds, including mono-, di-, and triphosphates, are generally soluble in aqueous solutions. However, depending on the degree and nature of substituent groups as well as the salt forms, the relative aqueous solubility can be altered.

In order to prepare aqueous solution formulations for intravenous administration, it is preferred that the solution be clear (i.e. free of precipitates), isotonic, and at a physiologically acceptable pH. The aqueous solubility of the compounds of the present invention varies as a function of both the subsitution and the salt form; with the latter having a greater effect on aqueous solubility. The salt forms of some compounds, even at a low concentration (such as <0.05% w/v), tend to form precipitates or have a limiting solubility in a normal aqueous saline solution (0.9% NaCl), which is a typical vehicle for intravenous administration.

Applicants have discovered that pharmaceutical formulations prepared using the compounds of the present invention in a non-ionic, iso-osmotic based vehicle provided clear, isotonic preparations at physiological pH. The level of non-isotonic tonicity modifiers such as mannitol or dextrose in the pharmaceutical formulations varied as a function of the desired target concentration of the said compounds (since the compounds themselves had an impact on the tonicity and contributed to the overall tonicity of the preparations). The pharmaceutical formulations made in non-ionic vehicles can be adjusted for a target pH over a wide range without compromising the solubility of the parent compound.

In one embodiment, the present invention provides a pharmaceutical formulation comprising a compound of Formula I, Ia, Ib, Ia-1, Ib-1, Ia-2, or Ib-2, or a pharmaceutically acceptable salt, solvate, or hydrate thereof, in an amount of 0.0005-0.3% w/v, a buffering agent, a chelating agent (such as EDTA), a non-ionic tonicity modifier, wherein the pharmaceutical formulation has a tonicity of 250-350 mOsm/kG and pH of 4-9. A preferred non-ionic tonicity modifier is dextrose or mannitol, in the amount of at least 2%, or at least 2.5%, or at least 3%, and no more than 7.5%; for example, in the range of 3-5, preferably 3.5-5, and more preferably 4.2-5% w/v. Such pharmaceutical formulation can or can not contain any ionic tonicity modifier such as NaCl. For example, the pharmaceutical formulation contains a compound of 2',3'-cinnamyl acetal-6-N-hexylurea AMP (compound 26), 2',3'-cinnamyl acetal-6-N-ethylurea AMP (compound 27), 2',3'-benzaldehyde acetal-6-N-ethylurea AMP (compound 36), trans-2',3'-cinnamyl acetal-6-N-ethylurea AMP (compound 41), trans-2',3'-benzaldehyde acetal-6-N-ethylurea AMP (compound 42), cis-2',3'-benzaldehyde acetal-6-N-ethylurea AMP (compound 43), $P^1$, $P^4$-di-trans-(2',3'-cinnamyl acetal-6-N-ethylurea adenosine 5'-) diphosphate (compound 48), $P^1$, $P^4$-di-trans-(2',3'-phenyl acetal-6-N-ethylurea adenosine 5'-) diphosphate (compound 49), or $P^1$, $P^4$-di-trans-(2',3'-phenylpropargyl acetal-6-N-ethylurea adenosine 5'-) diphosphate (compound 50).

Preparation of the Compounds

The compounds of the present invention can be conveniently synthesized by those skilled in the art using well-known chemical procedures. Mononucloside mono-, di- and triphosphates can be obtained from commercial sources or can be synthesized from the nucleoside using a variety of phosphorylation reactions which can be found in the chemical literature. Symmetrical and unsymmetrical dinucleotide polyphosphates can be prepared by activation of a nucleoside mono-, di- or triphosphate with a coupling agent such as, but not limited to, dicyclohexylcarbodiimide or 1,1'-carbonyldiimidazole, followed by condensation with another nucleoside mono-, di-, or triphosphate, which can be the same or different as the activated moiety. Activation of nucleoside triphosphates with dicyclohexylcarbodiimide gives a cyclical trimetaphosphate as the activated species, which can be advantageously reacted with a variety of nucleophiles to install unique substituents on the terminal phosphate of a triphosphate.

The compounds of the present invention can be prepared by derivatization or substitution at the level of the nucleoside, followed by phosphorylation and condensation as previously described, or the reactions can be carried out directly on the preformed mono- or dinucleotides. In the general Formulae Ia and Ib, the substituents at Y', Z', Y, and Z can be esters, carbamates, or carbonates, which are generally described by Formula II. Esters can be readily prepared by reacting a hydroxyl group of the furanose in a nucleoside or nucleotide with an activated form of an appropriate organic acid, such as an acid halide or acid anyhydride in the presence of an organic or inorganic base. Alternately, use of a suitable coupling reagent such as dicyclohexylcarbodiimide, 1,1'-carbonyldiimidazole and the like to activate the organic acid can be used to achieve the same result.

Carbamates or thiocarbamates can be most conveniently prepared by reaction of a hydroxyl group of the furanose in a nucleoside or nucleotide with any of a number of commercially available isocyanates or isothiocyanates, respectively, in an inert solvent. Alternately, when a desired isocyanate or isothiocyanate cannot be obtained from commercial sources, it can be prepared from the corresponding amine by the use of phosgene or thiophosgene, respectively, or their chemical equivalents. Carbonates or thiocarbonates can be synthesized by reacting the hydroxyl groups of a furanose in a nucleoside or nucleotide with an appropriate haloformate in the presence of an organic or inorganic base.

In the general Formulae Ia, Ib and Ib-1, the substituents at Y'and Z', and Y and Z, when taken together, can be taken to mean acetals, ketals or orthoesters, as described in Formula III.

Acetals and ketals can be readily prepared by reaction of the neighboring 2'- and 3'-hydroxyl groups of the furanose in an appropriate nucleoside or nucleotide with an aldehyde or ketone, respectively, or their chemical equivalents, in the presence of an acid catalyst. Particularly advantageous is the use of an organic acid, which can effect the transformation without affecting the integrity of the rest of the molecule. Alternately, strong acids such as trichloroacetic, p-toluenesulfonic, methanesulfonic and the like can be employed in catalytic amounts, in conjunction with inert solvents. Most preferred is formic acid, which can be removed by evaporation under reduced pressure, and is ideally suited to serve as both solvent and catalyst for these reactions. Alternately, trifluoroacetic acid can be substituted for formic acid in the reaction; provided that the reaction is carried out at low temperatures and the aldehyde or aldehyde equivalent used to prepare the acetal is stable to strong acid conditions.

Either of the two possible diastereomers that arise from the addition of the acetal to the chiral ribose residue can be synthesized by various procedures. In one example for preparing 2',3'-phenyl acetal-6-N-ethylurea AMP, one of the diastereomers of the acetal substituted with phenyl (cis-isomer, Compound 43) is prepared by the reaction between benzaldehyde and the 2' and 3' hydroxyl groups of the ribose at low temperature such as −10 to 0° C. The other trans isomer (Compound 42) is prepared by first performing the same acetal-forming reaction at room temperature to produce an equilibrium mixture of both cis and trans diastereomers, then followed by selective degradation under aqueous acid conditions of the cis-isomer. In another example for preparing 2',3'-cinnamyl acetal-6-N-ethylurea AMP (compound 27), a mixture of cis and trans isomers of the acetal substituted with styryl is prepared by the reaction between cinnamaldehyde and the 2' and 3' hydroxyl groups of the ribose at temperature such as 20° C. The trans isomer (Compound 41) is prepared from the mixture by selective degradation under aqueous acid conditions of the cis-isomer.

Cyclical orthoesters can be prepared by reaction of the neighboring 2'- and 3'-hydroxyl groups of a furanose with an acylic orthoester, in the presence of an acid. When the nucleoside or nucleotide to be derivatized is a purine that contains a 6-amino functionality or is a pyrimidine that contains a 4-amino functionality, it can be converted to the respective urea or thiourea by treatment with an isocyanate or isothiocyanate, respectively, as was previously described for carbamates or thiocarbamates of the 2'- or 3'-hydroxyls of a furanose. It was found that reactions of such an amino group with isocyanates or isothiocyanates can be carried out in the presence of one or more hydroxyl groups on a furanose, by appropriate manipulation of the stoichiometry of the reaction.

All of the derivitization reactions described herein can be carried out on preformed dinucleotide polyphosphates, which results in multiple products dependent on reaction stoichiometry and on whether multiple reactive groups are present. When multiple products are obtained, these can be conveniently separated by the use of preparative reverse phase high performance liquid chromatography (HPLC). Particularly advantageous is the use of C18 or phenyl reverse phase columns, in conjunction with gradients that start with ammonium acetate buffer and end with methanol. The use of a buffer provides for nucleotide stability and improved peak shape of the eluting products and the use of methanol allows for effective desorption of these lipophilic compounds from the column. Particularly advantageous is the use of ammonium acetate buffer solutions in conjunction with methanol, as these solvents are miscible in all proportions and can be readily removed from the chromatographed products by evaporation, followed by lyophilization.

While separation of multiple products can be done by HPLC, another strategy is to use nucleosides or nucleotides which contain only a single reactive functionality, whether because only one is present, or by the use of protecting groups to block side reactions at other positions in the molecule. This can be done at the level of preformed dinucleotide polyphosphates, or alternately, can be carried out on nucleoside mono-, di-, or triphosphates, leading to novel products in their own right, or can be coupled to other nucleoside mono-, di, or triphosphates by the methods which have already been described.

The above reactions and purification techniques can also be applied to carba-ribose analogues (e.g., $D_1=CH_2$) of nucleosides, nucleotides and their derivatives, and the terms such as "mononucleotide" and "dinucleotide" also apply to the carba-ribose analogues and other derivatives defined by Formulae I-IV.

Those skilled in the art will recognize various synthetic methodologies that can be employed to prepare non-toxic pharmaceutically acceptable salts and acylated prodrugs of the compounds.

Use of $P2Y_{12}$ Receptor Antagonist Compounds

This invention provides a method of preventing or treating diseases or conditions associated with platelet aggregation and/or platelet activation. The method also provides a method of treating thrombosis. The method comprises administering to a subject a pharmaceutical composition comprising a therapeutic effective amount of $P2Y_{12}$ receptor antagonist compound, wherein said amount is effective to bind the $P2Y_{12}$ receptors on platelets and inhibit ADP-induced platelet aggregation.

The compounds of general Formula I are antagonists of the effect of ADP on its platelet membrane receptor, the $P2Y_{12}$ receptor. The compounds of general Formula I are useful in therapy, in particular in the prevention or treatment of platelet aggregation. The compounds provide efficacy as antithrombotic agents by their ability to block ADP from acting at its platelet receptor site and thus prevent platelet aggregation. The compounds provide a more efficacious antithrombotic effect than aspirin, but with less profound effects on bleeding than antagonists of the fibrinogen receptor.

The $P2Y_{12}$ receptor antagonists of this invention, in contrast with currently available marketed products clopidogrel (PLAVIX®) and ticlopidine (TICLID®), bind to the $P2Y_{12}$ receptor in a reversible fashion and therefore, the effects of the treatment with compounds described in this invention are reversed by the simple discontinuation of the treatment, restoring the hemostatic functionality of the platelet as necessary. Since platelets are non-nucleated cell particles that lack the ability to synthesize new proteins, treatment of subjects with irreversible $P2Y_{12}$ antagonists results in the impairment of platelet function that lasts for the lifespan of the platelet (approximately 8 to 10 days). The use of irreversible $P2Y_{12}$ antagonists such as clopidogrel has been associated with increases in blood loss, transfusion requirements and rate of reoperation after cardiac surgery (Kapetanakis, et al., *Eur Heart J.* 26: 576-83, 2005). To avoid these complications, subjects undergoing elective surgeries are required to discontinue the treatment with irreversible antagonists for at least five days prior to the surgery, which increases the risk of a thrombotic event during this period. Therefore, the compounds described in this invention represent an advantage over the currently marketed compounds.

The ADP-induced platelet aggregation is mediated by the simultaneous activation of both $P2Y_{12}$ and $P2Y_1$ receptors, thus the combined administration of the Formula I compounds with antagonists of platelet $P2Y_1$ receptors can provide a more efficacious antithrombotic effect at concentrations of each antagonist that are below the effective concentrations to block each receptor subtype in other systems, resulting in a decrease of the potential manifestation of adverse effects. In addition, these compounds can be used in conjunction with lower doses of other platelet aggregation inhibitors, which work by different mechanisms, to reduce the possible side effects of said agents.

The compounds of the present invention are useful as antithrombotic agents, and are thus useful in the treatment or prevention of unstable angina, coronary angioplasty (PTCA) and myocardial infarction.

The compounds of the present invention are useful in the treatment or prevention of primary arterial thrombotic complications of atherosclerosis such as thrombotic stroke, peripheral vascular disease, and myocardial infarction without thrombolysis.

The compounds of the invention are useful for the treatment or prevention of arterial thrombotic complications due to interventions in atherosclerotic disease such as angioplasty, endarterectomy, stent placement, coronary and other vascular graft surgery.

The compounds of the invention are useful for the treatment or prevention of thrombotic complications of surgical or mechanical damage such as tissue salvage following surgical or accidental trauma, reconstructive surgery including skin flaps, and "reductive" surgery such as breast reduction.

The compounds of the present invention are useful for the prevention of mechanically-induced platelet activation in vivo, for example, caused by cardiopulmonary bypass, which results in temporary platelet dysfunction (prevention of microthromboembolism). The compounds of the present invention are useful for prevention of mechanically-induced platelet activation in vitro. For example, the compounds are useful in the preservation of blood products, e.g. platelet concentrates, prevention of shunt occlusion such as renal dialysis and plasmapheresis, and thrombosis secondary to vascular damage/inflammation such as vasculitis, arteritis, glomerulonephritis and organ graft rejection.

The compounds of the present invention are useful in disorders with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

The compounds of the invention are useful for the treatment or prevention of venous thrombosis such as deep vein thrombosis, veno-occlusive disease, hematological conditions such as thrombocythemia and polycythemia, and migraine.

The compounds of the present invention are useful in treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The compounds of the present invention are useful in treating chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment.

The compounds of the present invention are useful in treating diseases or conditions associated with platelet activation and/or aggregation produced by the contact of blood with an artificial device. In one embodiment, the artificial device is a paracorporeal artificial lung and an extracorporeal membrane oxigenation device. In another embodiment, the artificial device is an internal implantable artificial heart. In another embodiment, the artificial device is an apheresis instrument used to remove or isolate a specific component of the blood, and returning the remaining blood components to the donor. In yet another embodiment, the artificial device is a hemodialysis instrument.

The compounds of the present invention are useful in vitro to inhibit the aggregation of platelets in blood and blood products, e.g. for storage, or for ex vivo manipulations such as in diagnostic or research use. In such applications, the compounds are administered to the blood or blood product.

Additionally, if the compounds of the present invention have sufficient binding affinity and bear a fluorescent moiety, they are useful as biochemical probes for the $P2Y_{12}$ receptor.

In a preferred embodiment, the compounds are used in the treatment of unstable angina, coronary angioplasty and myocardial infarction.

In another preferred embodiment, the compounds are useful as adjunctive therapy in the prevention or treatment of thrombotic disorders, such as coronary arterial thrombosis during the management of unstable angina, coronary angioplasty and acute myocardial infarction, for example, as adjuvants of thrombolytic therapy. The compounds are also administered in combination with other antiplatelet and/or anticoagulant drugs such as heparin, aspirin, GP IIIb/IIIa antagonists, or thrombin inhibitors.

This invention provides a method of inhibiting platelet aggregation and clot formation in a mammal, especially a human, which comprises administering to the subject a compound of Formula (I) and a pharmaceutically acceptable carrier.

This invention further provides a method for inhibiting the reocclusion of an artery or vein and the formation of new blood clots following fibrinolytic therapy, which comprises administering to a subject a compound of Formula (I) and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule.

The increased clinical efficacy of the combination of the compounds described in this invention with fibrinolytic agents allows to use lower concentrations of the fibrinolytic agent and decrease the risk of hemorrhagic events. This in turn, allows the administration of fibrinolytic therapy over an extended period of time after a heart attack or stroke.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention can be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The active compounds can be administered systemically to target sites in a subject in need such that the extracellular concentration of a $P2Y_{12}$ agonist is elevated to block the binding of ADP to $P2Y_{12}$ receptor, thus inhibit the platelet aggregation. The term systemic as used herein includes subcutaneous injection, intravenous, intramuscular, intrasternal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile indictable preparation can be a sterile indictable solution or suspension in a non-toxic acceptable diligent or solvent. Among the acceptable vehicles and solvents that can be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds can also be systemically administered to the platelet aggregation sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target platelets in a pharmaceutically effective amount. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Intravitreal delivery can include single or multiple intravitreal injections, or via an implantable intravitreal device that releases $P2Y_{12}$ antagonists in a sustained capacity. Intravitreal delivery can also include delivery during surgical manipulations as either an adjunct to the intraocular irrigation solution or applied directly to the vitreous during the surgical procedure.

For systemic administration, plasma concentrations of active compounds delivered can vary according to compounds; but are generally $1\times10^{-10}$-$10$-$1\times10^{-4}$ moles/liter, and preferably $1\times10^{-8}$-$1\times10^{-5}$ moles/liter.

The pharmaceutical utility of $P2Y_{12}$ antagonist compounds of this invention is indicated by their inhibition of ADP-induced platelet aggregation. This widely used assay, as described in S. M. O. Hourani et al. *Br. J. Pharmacol.* 105, 453-457 (1992) relies on the measurement of the aggregation of a platelet suspension upon the addition of an aggregating agent such as ADP.

$P2Y_{12}$ Receptor Antagonist Compound-Eluting Stents

Coating stents with pharmaceutical agents has an inherent advantage over systemic administration, due to the ability to precisely deliver a much lower dose of the drug to the target area thus achieving high tissue concentration while minimizing the risk of systemic toxicity.

The present invention is also directed to a $P2Y_{12}$ receptor antagonist compound-eluting stent, which is a stent coated with one or more $P2Y_{12}$ receptor antagonist compounds of Formula I, Ia-1, Ia-2, Ib-1, or Ib-2, or a pharmaceutically acceptable salt, solvate, or hydrate thereof. When the stent is placed in a narrowed or damaged arterial vessel, a therapeutically effective amount of the compound(s) is eluted continuously from the stent to the local environment of the stent. Local delivery to vasculature facilitates the achievement of high regional drug concentrations, achieves a continuous exposure of the tissue to the drug, and reduces potential adverse effects and systemic toxicity due to lower systemic doses. The drug can be targeted directly to the required site. A therapeutically effective amount of the $P2Y_{12}$ receptor antagonist compound is an amount that is effective in preventing thrombosis and maintaining blood flow rate of the stented vessel, by decreasing in shear forces, relaxing vascular smooth muscle, and reducing narrowing of the vascular lumen restenosis.

By coating with one or more $P2Y_{12}$ receptor antagonist compounds, it is meant that the stent is coated with the $P2Y_{12}$ receptor antagonist compound itself (without a carrier), or the stent is coated with the compound in a carrier, i.e., the compound is in the form of a component of a mixture or matrix. In one embodiment, the stent is coated with a carrier that comprises at least one $P2Y_{12}$ receptor antagonist compound. The carrier is usually a biocompatible and non-toxic polymer. The polymer is preferably a biodegradable polymer or a biostable polymer. Biodegradable polymers suitable for this invention can be chosen from, but are not limited to, polycaprolactone, polylactic acid (D/L or L), poly(lactide-co-glycolide), poly(hydroxybutyrate), poly(hydroxybutyrate-covalerate), polydioxanone, polyorthoester, polyanhydride, poly(glycolic acid), poly(glycolic acid-cotrimethylene carbonate), polyphosphoester, polyphosphoester urethane, poly(amino acids), poly(trimethylene carbonate), poly(iminocarbonate), cyanoacrylates, polyalkylene oxalates, polyphosphazenes, and aliphatic polycarbonates. Alternately, natural biomolecules such as cellulose, starch, dextran, hyaluronic acid, and collagen can also be used. Biostable polymers can be chosen from, but are not limited to, polyurethanes, polyesters, polyamides, polyolefins, polycaprolactam, polyvinyl chloride, polyvinyl alcohol, poly(ethylene-vinyl alcohol), polyethers, silicones, acrylate polymers and copolymers, polyvinylmethyl ether, polyimide, and polyacrylonitrile.

The concentration of the $P2Y_{12}$ receptor antagonist compound in the stent is in general in the range of 0.001-20, preferably 0.01-10, and more preferably 0.1-5 $\mu g/mm^2$. Alternatively, the concentration of the $P2Y_{12}$ receptor antagonist compound in the stent is 1-500, preferably 10-100 $\mu g/mm$. Muni, et al. (*American Heart Journal*, 149:415-433, (2005)) have reported stent drug carriers, drug concentrations, stent sizes, and types of lesions; the article is incorporated herein by reference in its entirety.

In one embodiment, the elution of the $P2Y_{12}$ receptor antagonist compound is slow release and long-acting, i.e., the compound is eluted constantly and provides a local therapeutically effective amount at least until the epithelium damaged by the stent placement is healed. The local elution of the $P2Y_{12}$ receptor antagonist compound into the tissue surrounding the stent is preferably over a period of 3 to 6 months, and preferably 6 months. When the stent is coated with biodegradable polymers, the elution of the compound from the stent directly relates to the rate of degradation of the polymer.

$P2Y_{12}$ receptor antagonists useful in this invention are compounds that do not require hepatic, renal or any other metabolic transformation to become pharmacologically active.

The compound can be a prodrug if the conversion of the prodrug into the active species is carried out locally in the release area. For example, an ester prodrug can be converted into an active drug by tissue esterases such as endothelial esterases. All ester forms of $P2Y_{12}$ receptor antagonists are included in the application.

Recently, Wihlborg et al. describe the presence of $P2Y_{12}$ receptors in vascular smooth muscle (*Arterioscler. Thromb. Vasc. Biol.* 2004; 24: 1810-1815). The activation of these $P2Y_{12}$ receptors by endogenously released ADP results in vasoconstriction. This effect contributes to tonic contraction of smooth muscle cells by circulating ADP, or by released ADP from adhering platelets, endoethelial cells and leukocytes attracted to the damaged area as part of the healing process. $P2Y_{12}$ receptor activation is associated with an increase in cell proliferation and the onset of inflammation; both of these effects contribute to in-stent restenosis observed in approximately 10% of the patients treated with currently marketed stents.

Applicants have discovered the therapeutic benefits of $P2Y_{12}$ receptor antagonists-eluting stents. The elution of $P2Y_{12}$ receptor antagonists to local stented tissues can prevent the stenosis of stented arteries by relaxing the arterial smooth muscle, which results in an increase in blood flow rate of the stented artery and a decrease in shear forces that could promote thrombosis. Additionally, the inhibition of vascular smooth muscle contraction in stented arteries can decrease the risk of ischemia and thrombosis. Therefore, the use of $P2Y_{12}$ receptor antagonists-eluting stents improves the therapeutic benefit of current stents by decreasing the incidence of thrombosis and restenosis and improving of the flow rate of perfusion of the stented artery due to the relaxing activity of smooth muscle cells.

$P2Y_{12}$ receptor antagonist compound-eluting stents can be used as in situ antithrombotics to decrease the risk of stent thrombosis by a constant delivery of the $P2Y_{12}$ antagonist for several months. This treatment will decrease the risk of thrombosis by inhibiting the aggregation of platelets in the stented artery. $P2Y_{12}$ receptor antagonist compounds are useful to coat all types of stents, including coronary stents, cerebral arterial stents (basilar or vertebral arteries), other arterial stents (aortic, carotid, renal, peripheral, etc), and vein stents (portal, renal, including vein graft conduits). Peripheral artery is defined as an artery that carries blood to upper and lower extremities. $P2Y_{12}$ receptor antagonist eluting stents are useful for saphenous vein grafts previously grafted in coronary arteries, which have reduced patency due to restenosis or thrombosis. Preferred stents for this invention are coronary stents.

Marketed P2Y$_{12}$ antagonists such as PLAVIX® and TICLID® are not suitable for coating stents because PLAVIX® and TICLID® need to be metabolized in the liver in order to generate the active metabolites. The P2Y$_{12}$ receptor antagonists of the present invention do not require metabolism for activation, and therefore they are capable of exerting their antithrombotic and smooth muscle relaxing activity in situ.

P2Y$_{12}$ receptor antagonist compound-eluting stents provide the advantages of inhibiting the contraction of vascular smooth muscle cells, inhibiting cell proliferation, and reducing inflammation. P2Y$_{12}$ receptor antagonist compound-eluting stents are useful in preventing the thrombosis and restenosis observed on patients after placement of bear metal and other drug-eluting stents.

Currently, patients who receive stents require the prophylactic treatment with anti thrombotic drugs for at least 3 months to reduce the risk of thrombosis. The local delivery of an antiplatelet and vascular smooth muscle relaxant drug with potential for anti-inflammatory effects (due to the inhibition of platelet activation and release of pro-inflammatory substances) such as the P2Y$_{12}$ receptor antagonists of the present invention provide additional benefit compared with the current stent therapy.

The present invention provides a method for treating blocked or narrowed arteries. The method comprises the step of placing a P2Y$_{12}$ receptor antagonist compound-eluting stent according to claim 1 in a narrowed or blocked artery of a patient, whereby a therapeutically effective amount of the compound is eluted to the stented area, whereby the blood flow is resumed by the stent and the restenosis and thrombosis are prevented by the P2Y$_{12}$ receptor antagonist compound. The artery can be, for example, coronary artery, cerebral artery, or peripheral artery, which has been narrowed or blocked by a plaque or a plaque rupture, respectively. The inserted stent delivers P2Y$_{12}$ receptor antagonist compound locally to the stented area, and decreases the incidence of thrombosis and restenosis. The method optionally comprises the step of monitoring the patient to ensure patency of the stented artery. For example, when the stent is inserted into the coronary artery, the patient can be monitored by clinical symptoms of the cardic function, e.g., electrocardiogram (EKG), to determine if the blood flow in the heart muscle is restored. When the stent is inserted into the carotid artery, the patient can be monitored by ultrasound to determine if the narrowed artery is restored, and by evaluation of clinical symptoms such as headache, facial droop, loss of coordination, vertigo and depressed mental status. When the stent is inserted into the cerebral arteries, the patient can be monitored by neurological examinations including clinical symptoms such as headache, facial droop, loss of coordination, vertigo and depressed mental status.

Preparation of P2Y$_{12}$ Receptor Antagonist Compound-Eluting Stents

Stents are frequently made from stainless steel. Stents can be made of any biocompatible metal, including, but not limited to, steel, cobalt, titanium, tantalum, chromium, zirconium, niobium, tungsten, platinum, palladium, vanadium, silver, gold, molybdenum, nickel, or magnesium, and alloys thereof in any combination. Alternately, stents can be constructed of non-metallic biocompatible materials, such as bioabsorbable or biostable polymers.

The preparation of drug-eluting stents has been described in Kavanagh, et al. (*Pharmacology & Therapeutics*, 102: 1-15, 2004), Doorty, et al. (*Cardiovascular Pathology*, 12: 105-110, 2003), Hossainy (U.S. Pat. No. 6,908,624). Both articles are incorporated herein by reference in their entirety.

In general, P2Y$_{12}$ receptor antagonist compounds of the present invention are preferably not attached directly (covalently or non-covalently) to the surface of an unmodified stent. In order to deliver the compounds of the present invention to the site of action, the stent is preferably coated with an organic or inorganic polymer (or polymers) or some other substance (such as an inorganic coating) that is able to retain the compound to be delivered and release it at a desired rate. The nature of this retention can be covalent or non-covalent, with the latter being preferred.

In one embodiment, the stent is first modified by coating it with an inorganic substance or an organic or inorganic polymer which is capable of binding the compound to the stent surface. For example, when the P2Y$_{12}$ receptor antagonist compound bears a phosphate or other acidic moiety, the stent is first coated with a substance or a polymer that bears a basic moiety, and the compound is bound to the modified stent by an ionic interaction. When the P2Y$_{12}$ receptor antagonist compound bears a basic moiety, the stent is first coated with a substance or a polymer that bears an acidic moiety, and the compound is bound to the modified stent by an ionic interaction.

In another embodiment, the P2Y$_{12}$ receptor antagonist compound is first incorporated into a compatible polymer matrix, which is then used to coat a stent. The advantage of this approach is that the elution of the P2Y$_{12}$ receptor antagonist compound from the stent depends on the property of the polymer, thus one can select a suitable polymer, which provides controlled and sustained release of the P2Y$_{12}$ receptor antagonist compound to the site of action. The polymer can be hydrophilic, hydrophobic, biodegradable, or biostable, thus one can further select a polymer to optimize the desired therapeutic effect.

The present invention provides a composition comprising at least one biodegradable polymer and at least one P2Y$_{12}$ receptor antagonist compound of general Formula I, wherein said biodegradable polymer is selected from the group consisting of polycaprolactone, polylactic acid, poly(lactide-co-glycolide), poly(hydroxybutyrate), poly(hydroxybutyrate-covalerate), polydioxanone, polyorthoester, polyanhydride, poly(glycolic acid), poly(glycolic acid-cotrimethylene carbonate), polyphosphoester, polyphosphoester urethane, poly (amino acids), poly(trimethylene carbonate), poly(iminocarbonate), cyanoacrylates, polyalkylene oxalates, polyphosphazenes, aliphatic polycarbonates, cellulose, starch, dextran, hyaluronic acid, and collagen.

The present invention further provides a composition comprising at least one biostable polymer and at least one P2Y$_{12}$ receptor antagonist compound of general Formula I, wherein said biostable polymer is selected from the group consisting of polyurethanes, polyesters, polyamides, polyolefins, polycaprolactam, polyvinyl chloride, polyvinyl alcohol, poly(ethylene-vinyl alcohol), polyethers, silicones, acrylate polymers and copolymers, polyvinylmethyl ether, polyimide, and polyacrylonitrile.

When biodegradable polymers are used, the P2Y$_{12}$ receptor antagonist compound is incorporated into the polymer matrix and released in a controlled manner by a gradual degradation of the polymer matrix. This degradation can occur by various processes, including hydrolysis, metabolism, bulk erosion, or polymer surface erosion. When biostable polymers are used, the P2Y$_{12}$ receptor antagonist compound is uniformly distributed in the polymer or encapsulated within the polymer, from which the compound is eluted via diffusion processes or through pores of the polymer structure.

The P2Y$_{12}$ receptor antagonist compound can be incorporated into the polymer via processes known to those skilled in the art. These include, but are not limited to, encapsulation of the compound within a polymer matrix during polymer synthesis prior to application of the polymer to the stent, dissolving both polymer and the compound in an appropriate solvent and applying the solution to a stent, after which the solvent is allowed to evaporate and the stent is allowed to dry, or pre-coating a stent with a polymer, after which the therapeutic agent is applied as a solution in an appropriate solvent. Application methods can include, but are not limited to, spraying, dipping, or spin coating processes.

The invention is illustrated further by the following examples that are not to be construed as limiting the invention in scope to the specific procedures described in them.

EXAMPLES

Example 1

2'(3')—O-((phenylaminocarbonyl)-uridine 5'-)triphosphate

Uridine 5'-triphosphate, ditributylammonium salt (100 mg, 0.176 mmol; prepared from the trisodium salt by treatment with Dowex 50Wx4H$^+$ in water, followed by mixing the protonated species with an excess of tributylamine, stripping and lyophilization) was dissolved in dry DMF (1 mL) and phenylisocyanate (19 µL, 0.176 mmol) added. The reaction mixture was heated at 45° C. for 15 minutes, at which point a further portion of phenylisocyanate (19 µL, 0.176 mmol) was added. The solution was heated at 45° C. overnight and the DMF was removed on a rotary evaporator. The residual oil was partitioned between water (2 mL) and ethyl acetate (2 mL) and the layers were separated. The aqueous layer was extracted twice more with ethyl acetate (2 mL each) and the water was removed on a rotary evaporator. The residue was dissolved in water (1.5 mL) and the product isolated by repeated injections onto a preparative HPLC column (Alltech Nucleotide/Nucleoside C18, 7 um, 10×250 mm, gradient from 0.1 M ammonium acetate to methanol over 30 minutes, 5 mL/min, monitor at 260 nm). The yield of the carbamate was 26 mg (22%, calculated for the tetraammonium salt). $^1$H NMR showed the product to be a mixture of 2' and 3' carbamates. The product so obtained can be used for the purposes of this invention per se or can be activated with a suitable coupling agent (e.g. a carbodiimide) and reacted with a variety of nucleotides to generate novel dinucleoside polyphosphates.

1H NMR (D2O, 300 MHz): δ 4.10-4.47 (m, 4H), 5.17 (m, 1H), 5.83 (dd, 1H), 5.96 (m, 1H), 7.04 (t, 1H), 7.25 (m, 4H), 7.79 (m, 1H). 31P NMR (D2O, 121.47 MHz): δ−9.54 (m, 1P), −10.20 (m, 1P), −21.87 (m, 1P).

Example 2

2'(3')-O-(phenylaminocarbonyl)-P$^1$,P$^4$-di(uridine 5'-)tetraphosphate ["monophenylcarbamate Up4U"], Di-2'(3')-O-(phenylaminocarbonyl)-P$^1$,P$^4$-di(uridine 5'-)tetraphosphate ["diphenylcarbamate Up4U"] and Tri-2'(3')-O-(phenylaminocarbonyl)-P$^1$,P$^4$-di(uridine 5'-)tetraphosphate ["triphenylcarbamate Up4U"]

P$^1$,P$^4$-Di(uridine 5'-) tetraphosphate, ditributylammonium salt (211 mg, 0.182 mmol; prepared from the tetrasodium salt by treatment with Dowex 50Wx4H$^+$ in water, followed by mixing the protonated species with an excess of tributylamine, stripping and lyophilization) was dissolved in dry DMF (2 mL) and phenylisocyanate (40 µL, 3.64 mmol) added in a single portion. The homogeneous reaction mixture was heated overnight at 45° C., whereupon TLC (silica gel, 50% isopropanol/50% ammonium hydroxide) indicated a substantial conversion to two products. The solvent was removed on a rotary evaporator and the residue was partitioned between water (7 mL) and ethyl acetate (10 mL). The layers were separated, and the aqueous was extracted twice more with ethyl acetate. (10 mL each). The water was removed from the aqueous extract and the residual oil lyophilized overnight. The solid obtained was reconstituted in water (3 mL) and the two products separated by repeated injections onto a semi-preparative HPLC column (Alltech Nucleotide/Nucleoside C18, 7 um, 10×250 mm, gradient from 0.1 M ammonium acetate to methanol over 30 minutes, 5 mL/min, monitor at 260 nm). Stripping and lyophilization gave the mono-phenylcarbamate (48 mg, 27% yield), di-phenylcarbamate (16 mg, 8% yield) and a trace amount of the triphenylcarbamate, as the tetraammonium salts. All three products were mixtures of the corresponding 2'/3' regiosiomers.

Monophenylcarbamate: $^1$H NMR (D$_2$O, 300 MHz): δ 4.08-4.65 (m, 9H), 5.14 (d, 1H), 5.75-5.94 (m, 4H), 7.01 (t, 1H), 7.22 (m, 4H), 7.76 (m, 2H). $^{31}$P NMR (D$_2$O, 121.47 MHz): δ−10.17 (m, 2P), −21.81 (m, 2P).

Diphenylcarbamate: $^1$H NMR (D$_2$O, 300 MHz): δ 4.13-4.43 (m, 8H), 5.12 (m, 2H), 5.84 (m, 4H), 7.01 (m, 2H), 7.21 (m, 8H), 7.75 (dd, 2H). $^{31}$P NMR (D$_2$O, 121.47 MHz): δ −10.19 (m, 2P), −21.65 (m, 2P).

Triphenylcarbamate: $^1$H NMR (D$_2$O, 300 MHz): δ 4.29 (m, 7H), 4.5.10 (m, 1H), 5.27 (m, 2H), 5.87 (m, 4H), 7.09 (m, 15H), 7.76 (d, 2H). $^{31}$P NMR (D$_2$O, 121.47 MHz): δ−10.30 (m, 2P), −21.73 (m, 2P).

Example 3

P$^1$,P$^4$-Tetra-(2'(3')-O-(phenylaminocarbonyl) di(uridine 5'-)tetraphosphate [tetraphenylcarbamate Up4U"]

This derivative was prepared according to the method of example 2. P$^1$,P$^4$-Di(uridine 5'-) tetraphosphate, ditributylammonium salt (200 mg, 0.172 mmol) was treated with 16 eq of phenylisocyanate (300 uL, 2.76 mmol) in DMF and stirred overnight at 35° C. The solvent was evaporated and the excess reagents removed by extraction of an aqueous solution of the product with ethyl acetate. Following preparative HPLC as previously described, 93 mg (30% yield) of the tetraphenylcarbamate was obtained.

Tetraphenylcarbamate: $^1$H NMR (D$_2$O, 300 MHz): δ 7.75 (d, 2H), 7.11 (m, 16H), 6.94 (m, 4H), 5.95 (d, 2H), 5.80 (d, 2H), 5.32 (m, 2H), 5.23 (m, 2H), 4.42 (m, 2H), 4.25 (m, 2H), 4.16 (m, 2H). $^{31}$P NMR (D$_2$O, 121.47 MHz): δ −10.30 (m, 2P), −22.32 (m, 2P).

Example 4

2',3'-(benzyl)methylenedioxy-P$^1$,P$^4$-di(uridine 5'-) tetraphosphate ["Mono 2'/3' benzylacetal Up4U"] and P$^1$,P$^4$-Di-(2',3'-((benzyl)methylenedioxy) di(uridine 5'-)tetraphosphate ["Di 2'/3' benzylacetal Up4U"]

P$^1$,P$^4$-Di(uridine 5'-) tetraphosphate, tetrasodium salt (290 mg, 0.332 mmol) was dissolved in 98% formic acid and phenylacetaldehyde, dimethyl acetal (110 uL, 0.662 mmol) added. The reaction was stirred at ambient temperature for 3 days, at which point TLC (silica gel, 50% isopropanol/50% ammonium hydroxide) and HPLC (C18) showed good conversion to two less polar products. The formic acid was removed on a rotary evaporator, and the residue partitioned between 0.7 M ammonium bicarbonate (15 mL) and butyl acetate (15 mL). The layers were separated and the aqueous was washed with a further portion of butyl acetate (10 mL). The aqueous layer was stripped and the residue lyophilized overnight. The crude product was dissolved in water (5 mL) and the components separated by preparative HPLC (Waters Novapak C18, 6 um, 25×100 mm, gradient from 0.1 M ammonium acetate to methanol over 30 minutes, 30 mL/min, monitor at 260 nm). The yield of the monoacetal was 88 mg (28%) and of the diacetal 60 mg (17%), both as the tetraammonium salts.

Monoacetal: $^1$H NMR (D$_2$O, 300 MHz): δ 2.99 (d, 2H), 4.01-4.32 (m, 8H), 4.77 (m, 2H), 5.33 (m, 2H), 5.74 (d, 1H), 5.81 (m, 2H), 7.21 (m, 5H), 7.64 (d, 1H), 7.79 (d, 1H). $^{31}$P NMR (D$_2$O, 121.47 MHz): δ −10.18 (m, 1P), −10.78 (m, 1P), −22.00 (m, 2P).

Diacetal: $^1$H NMR (D$_2$O, 300 MHz): δ 2.98 (d, 4H), 3.99 (m, 4H), 4.27 (m, 2H), 5.27 (m, 2H), 5.36 (m, 2H), 5.73 (d, J=8.1 Hz, 2H), 7.21 (m, 10H), 7.61 (d, J=8.1 Hz, 2H). $^{31}$P NMR (D$_2$O, 121.47 MHz): δ −10.57 (m, 2P), −21.81 (m, 2P).

Example 5

2',3'-((benzyl)methylenedioxy) P$^1$,P$^3$-uridine 5'-) triphosphate ["2'3' phenylacetaldehyde acetal Up3U"] and P$^1$,P$^3$-Di-(2',3'-((benzyl)methylenedioxy) uridine 5'-)triphosphate ["di 2'3' phenylacetaldehyde acetal Up3U"]

P$^1$,P$^3$-Di(uridine 5'-) triphosphate, trisodium salt (100 mg, 0.129 mmol) was dissolved in 98% formic acid and phenylacetaldehyde, dimethyl acetal (64 uL, 0.386 mmol) added. After overnight stirring at room temperature, the formic acid was removed, and the residue partitioned between 1 M sodium bicarbonate and ethyl acetate. Following removal of the organic layer, the product was purified on preparative HPLC, as previously described. Following lyophilization, 40 mg (36%) of the monoacetal and 24 mg (19%) of the diacetal were obtained.

Monoacetal: $^1$H NMR (D$_2$O, 300 MHz): δ 7.7s (d, 2H), 7.54 (d, 2H), 7.16 (s, 5H), 5.70 (m, 3H), 5.31 (s, 1H), 5.23 (s, 1H), 4.66 (m, 2H), 4.10 (m, 8H), 2.93 (d, 2H). $^{31}$P NMR (D$_2$O, 121.47 MHz): δ −10.30 (m, 1P), 10.81 (m, 1P), −21.99 (m, 1P).

Diacetal: $^1$H NMR (D$_2$O, 300 MHz): δ 7.51 (d, 2H), 7.15 (m, 10H), 5.65 (d, 2H), 5.31 (d, 2H), 5.20 (t, 2H), 4.63 (m, 2H), 4.13 (m, 2H), 3.88 (m, 4H), 2.90 (d, 4H). $^{31}$P NMR (D$_2$O, 121.47 MHz): δ −10.75 (m, 2P), −21.97 (m, 1P).

Example 6

P$^1$-2',3'-((benzyl)methylenedioxy) (uridine 5'-) P$^4$-(deoxycytidine 5'-) tetraphosphate ["2'3' phenylacetadehyde acetal Up4dC"]

P$^1$-(uridine 5'-) P$^4$-(deoxycytidine 5'-) tetraphosphate, tetrasodium salt (100 mg, 0.16 mmol) was dissolved in 98% formic acid (1 mL), and phenylacetaldehyde, dimethyl acetal (57 uL, 0.384 mmol) added. After overnight stirring, the formic acid was removed and the residue partitioned between 1 M sodium bicarbonate and ethyl acetate. After separation of the layers, the product was purified on preparative HPLC, as previously described. Yield 40 mg (36%). This product was amenable to subsequent modification of the deoxy cytidine base by the procedures described in examples 9-13, giving rise to lipophilic bifunctional molecules falling within the scope of this invention.

Monoacetal: $^1$H NMR (D$_2$O, 300 MHz): δ 7.98 (d, 1H), 7.62 (d, 1H), 7.21 (m, 5H), 6.11 (m, 2H), 5.74 (d, 1H), 5.39 (d, 1H), 5.31 (t, 1H), 4.77 (m, 2H), 4.45 (m, 1H), 4.32 (m, 1H), 4.03 (m, 5H), 2.99 (d, 2H), 2.29 and 2.21 (M, 2H). $^{31}$P NMR (D$_2$O, 121.47 MHz): δ−10.15 (m, 1P), −10.68 (m, 1P), −21.98 (m, 2P).

Example 7

3'-O-(phenylaminocarbonyl)-2'-deoxy (uridine 5')-monophosphate

Deoxyuridine 5'-monophosphate, tetrabutylammonium salt (135 mg, 0.274 mmol; prepared from the disodium salt by treatment with Dowex 50Wx4H$^+$, followed by stirring the resultant neutral species with excess tributylamine, stripping and lyophilization) was dissolved in dry DMF (1 mL). Phenylisocyanate (60 uL, 0.547 mmol) was added and the mixture heated overnight at 45° C., at which time TLC (silica gel, 50% isopropanol/50% ammonium hydroxide) and HPLC (C18) indicated a substantial conversion to a less polar product. The DMF was stripped on a rotary evaporator and the oily residue partitioned between water (10 mL) and ethyl acetate (10 mL). The layers were separated and the aqueous layer was rewashed with ethyl acetate (2×10 mL). The water was removed and the residue was dissolved in water (2 mL). The product was isolated by repeated injections onto semi-preparative HPLC (Alltech Nucleotide/Nucleoside C18, 7 um, 10×250 mm, gradient from 0.1 M ammonium acetate to methanol over 30 minutes, 5 mL/min, monitor at 260 nm). The yield was 67 mg as the diammonium salt (53%).

$^1$H NMR (D$_2$O, 300 MHz): δ 2.21 (m, 2H), 3.84 (s, 2H), 4.13 (s, 1H), 5.08 (d, 1H), 5.63 (d, 1H), 6.06 (t, 1H), 6.89 (br. t, 1H), 7.10 (m, 4H), 7.72 (d, 1H). $^{31}$P NMR (D$_2$O, 121.47 MHz): δ−2.31 (s).

Example 8

P$^1$-(3'-O-(phenylaminocarbonyl)-2'-deoxyuridine 5'-)P$^4$-(uridine 5'-)tetraphosphate Uridine 5'-triphosphate, ditributylammonium salt (prepared from the trisodium salt by treatment with Dowex 50Wx4H$^+$, followed by stirring the resultant neutral species with excess tributylamine, stripping and lyophilization) is treated with 1.5 equivalents of dicyclohexylcarbodiimide in DMF for 2 hours at room temperature. The dicyclohexylurea is filtered off, and the resultant uridine 5'-cyclical triphosphate is treated with 3'-O-(phenylaminocarbonyl)-2'-deoxy (uridine 5')-monophosphate (Example 7 compound), which is in the monotributylammonium salt form. The reaction mixture is stirred for several days at 45° C., and the solvent is removed. The products are separated by preparative HPLC, as has been previously described.

Example 9

2'(3')-(2-methylamino)benzoyl-P$^1$,P$^4$-di(uridine 5'-) tetraphosphate ("MANT Up4U") and P$^1$,P$^4$-Di-(2' (3')-(2-methylamino)benzoyl uridine 5'-)tetraphosphate ("Bis MANT Up4U")

P$^1$,P$^4$-Di(uridine 5'-) tetraphosphate, tetrasodium salt (800 mg, 0.93 mmol) was dissolved in water (5 mL) and the pH adjusted to 7.6 by the addition of solid sodium bicarbonate. N,N-dimethylformamide (DMF, 5 mL) was added, followed by N-methylisatoic anhydride (231 mg, 1.3 mmol) and the suspension was heated at 50° C. for 2.5 hrs. TLC (silica gel, 50% isopropanol, 50% ammonium hydroxide) indicated that the reaction was not done by this time, so a further portion of N-methylisatoic anhydride (100 mg, 0.56 mmol) was added and the reaction heated for another hour. The DMF was removed on a rotary evaporator and the residue was dissolved in a minimum of water and applied to a DEAE Sephadex A-25 column (3×60 cm). The column was eluted with a stepwise gradient from water to 1 M ammonium bicarbonate and the eluent monitored with a UV detector set at 254 nm. The two products that eluted were collected separately and the solvent was removed from each and the residue lyophilized overnight. $^1$H NMR indicated that the first product to elute was the monoacylated compound, while the latter was the diacylated derivative, and that both were mixtures with the acylation at either the 2' or 3' hydroxyls, but without two carbamates on the same sugar. The yield of the monoaminobenzoylated product was 150 mg (16%); the yield of the diaminobenzoylated compound was 91 mg (8.7%).

Monoaminobenzoylated derivative: $^1$H NMR (D$_2$O, 300 MHz): δ 2.70 (s, 3H), 4.09-4.55 (m, 9H), 5.34 (m, 1H), 5.71 (m, 2H), 5.83 (dd, 1H), 6.01 (m, 1H), 6.57 (m, 1H), 6.65 (m, 1H), 7.25 (t, 1H), 7.72 (d, 2H), 7.81 (m, 2H). $^{31}$P NMR (D$_2$O, 121.47 MHz): δ −10.20 (m, 2P), −21.83 (m, 2P).

Diaminobenzoylated derivative: $^1$H NMR (D$_2$O, 300 MHz): δ 2.69 (s, 6H), 4.15-4.51 (m, 8H), 5.27 (m, 2H), 5.86 (m, 4H), 6.60 (m, 4H), 7.30 (m, 2H), 7.79 (m, 4H). $^{31}$P NMR (D$_2$O, 121.47 MHz): δ −10.16 (m, 2P), −21.76 (m, 2P).

Example 10

P$^1$-(4-N-(4-methoxyphenyl)aminocarbonylcytidine 5'-)-P$^4$-(uridine 5'-) tetraphosphate P$^1$-(cytidine 5'-)-P$^4$-(uridine 5'-) tetraphosphate, ditributylammonium salt (50 mg, 0.043 mmol; prepared from the tetraammonium salt by treatment with Dowex 50Wx4H$^+$ in water, followed by mixing the protonated species with an excess of tributylamine in methanol, stripping and lyophilization) was dissolved in dry DMF (1 mL) and tributylamine (10 uL, 0.43 mmol), and p-methoxyphenylisocyanate (8.4 uL, 0.648 mmol) were added in a single portion. The homogeneous reaction mixture was heated overnight at 35° C., whereupon TLC (silica gel, 50% isopropanol/50% ammonium hydroxide) and HPLC (C18) indicated a substantial conversion to a single product. The solvent was removed on a rotary evaporator and the residue dissolved in water (1 mL). The product was isolated by repeated injections onto a semi-preparative HPLC column (Alltech Nucleotide/Nucleoside C18, 7 um, 10×250 mm, gradient from 0.1 M ammonium acetate to methanol over 30 minutes, 5 mL/min, monitor at 260 nm). Stripping and lyophilization gave the p-methoxyphenylurea (24 mg, 55% yield), as the tetraammonium salt.

The product so obtained can be derivatized on the 2' and/or 3' hydroxyl groups according to the foregoing methods (e.g. Examples 2-6).

$^1$H NMR (D$_2$O, 300 MHz): δ 3.59 (s, 3H), 4.01-4.20 (m, 10H), 5.68 (m, 3H), 6.19 (d, 1H), 6.71 (d, 2H), 7.18 (d, 2H), 7.67 (d, 1H), 8.06 (d, 1H). $^{31}$P NMR (D$_2$O, 121.47 MHz): δ −10.13 (m, 2P), −21.76 (m, 2P).

Example 11

P$^1$-((4-bromophenyl)ethenocytidine 5'-)-P$^4$-(uridine 5'-) tetraphosphate

P$^1$-(cytidine 5'-)-P$^4$-(uridine 5'-) tetraphosphate, tetrasodium salt (500 mg, 0.57 mmol) was dissolved in water (5 mL) and a solution of 2,4'-dibromoacetophenone (792 mg, 2.85 mmol) in DMF (15 mL) added. The mixture was heated overnight at 40° C., and a further portion of the dibromoketone (400 mg, 1.44 mmol) in DMF (5 mL) added. The rection was heated a further 5 hrs, and the solvents removed by evaporation. The residue was partitioned between water (20 mL) and ethyl acetate (25 mL) and the layers separated. The aqueous layer was washed with further ethyl acetate (2×15 mL) and the aqueous evaporated to dryness. The residue was dissolved in water (5 mL) and the product was isolated by repeated injections onto a semi-preparative HPLC column (see example 6 for conditions). The yield of the pure etheno compound was 80 mg (13.5%)

$^1$H NMR (D$_2$O, 300 MHz): δ 4.06 (m, 8H), 4.36 (m, 2H), 5.64 (dd, 2H), 6.07 (d, 1H), 6.74 (d, 1H), 7.45 (d, 2H), 7.54 (d, 2H), 7.59 (d, 1H), 7.63 (d, 1H), 7.93 (s, 1H). $^{31}$P NMR (D$_2$O, 121.47 MHz): δ −10.09 (m, 2P), −21.59 (m, 2P).

Example 12

P$^1$-((4-bromophenyl)etheno-2'-deoxycytidine 5'-)-P$^4$-(uridine 5'-) tetraphosphate Example 11 product was prepared from 100 mg P$^1$-(2'-deoxycytidine 5'-)-P$^4$-(uridine 5'-) tetraphosphate, tetrasodium salt and 2,4'-dibromoacetophenone, according to the general method of example 10. Yield=35 mg (30%).

$^1$H NMR (D$_2$O, 300 MHz): δ 2.31 (m, 2H), 4.03 (m, 8H), 5.60 (dd, 2H), 6.41 (t, 1H), 6.73 (d, 1H), 7.53 (m, 5H), 7.65 (d, 1H), 7.93 (s, 1H). $^{31}$P NMR (D$_2$O, 121.47 MHz): δ −10.11 (m, 2P), −21.58 (m, 2P).

Example 13

P$^1$,P$^4$-Di((4-bromophenyl)ethenocytidine 5'-)-tetraphosphate

Example 12 product was prepared from 50 mg P$^1$,P$^4$-Di (cytidine 5'-) tetraphosphate, tetrasodium salt and 2,4'-dibromoacetophenone, according to the general method of example 10. Yield=20 mg (29%).

$^1$H NMR (D$_2$O, 300 MHz): δ 4.24 (m, 10H), 5.98 (d, 2H), 6.39 (d, 2H), 7.14 (m, 8H), 7.45 (m, 4H).). $^{31}$P NMR (D$_2$O, 121.47 MHz): δ −10.13 (m, 2P), −21.68 (m, 2P).

Example 14

P$^1$-((4-phenylphenyl)ethenocytidine 5'-)-P$^4$-(cytidine 5'-) tetraphosphate

Example 14 product was prepared from 50 mg P$^1$,P$^4$-Di (cytidine 5'-) tetraphosphate, tetrasodium salt and 2-bromo-4'-phenylacetophenone, according to the general method of example 10. Yield=15 mg (13%).

$^1$H NMR (D$_2$O, 300 MHz): δ 4.10 (m, 10H), 5.48 (d, 1H), 5.87 (m, 2H), 6.68 (d, 1H), 7.20 (m, 3H), 7.36 (m, 6H), 7.68 (m, 3H). $^{31}$P NMR (D$_2$O, 121.47 MHz): δ −10.08 (m, 2P), −21.78 (m, 2P).

The products of Examples 12-14 can be further derivatized according to the methods of Examples 1-8, to give bifunctional molecules that fall within the scope of the invention.

Example 15

2',3'-phenylacetaldehyde acetal adenosine 5'-monophosphate

Adenosine 5'-monophosphate, free acid (10.0 g, 28.8 mmol) was dissolved in trifluoroacetic acid (50 mL) and phenylacetaldehyde, dimethylacetal (18.50 mL, 121 mmol) added. The reaction was stirred at ambient temperature for 3 hours, after which the trifluoroacetic acid was evaporated and the residue partitioned between 1 M sodium bicarbonate (80 mL) and ethyl acetate (40 mL). The layers were separated, and the product was isolated from the aqueous layer via $C_{18}$ preparative HPLC. Yield=7.50 g (59%). The ammonium salt so obtained was converted to the mono-tributylammonium salt via treatment with a slight excess of tributylamine in aqueous N,N-dimethylformamide, followed by evaporation and drying.

$^1$H NMR (D$_2$O, 300 MHz): δ 3.06 (d, 2H), 3.86 (m, 2H), 4.39 (m, 1H), 4.91 (m, 1H), 5.18 (m, 1H), 5.36 (t, 1H), 5.63 (d, 1H), 7.23 (m, 5H), 8.09 (s, 1H), 8.20 (s, 1H). $^{31}$P NMR (D$_2$O, 121.47 MHz): δ 2.17 (s).

Example 16

2',3'-cinnamyl acetal adenosine 5'-monophosphate

Adenosine 5'-monophosphate, free acid (1.0 g, 2.88 mmol) was dissolved in 98% formic acid (5 mL) and cinnamaldehyde (1.14 g, 8.65 mmol) added. The reaction was stirred at ambient temperature for 3 hours, after which the formic acid was evaporated and the residue partitioned between 1 M sodium bicarbonate (25 mL) and ethyl acetate (20 mL). The layers were separated, and the product was isolated from the aqueous layer via preparative HPLC. Yield=0.202 g (15%).

$^1$H NMR (D$_2$O, 300 MHz): δ 3.97 (m, 2H), 4.50 (m, 1H), 5.04 (m, 1H), 5.29 (m, 1H), 5.65 (d, 0.4H), 5.86 (d, 0.6H), 6.24 (m, 2H), 6.87 (dd, 1H), 7.27 (m, 3H), 7.43 (m, 2H), 8.12 (d, 1H), 8.28 (d, 1H). $^{31}$P NMR (D$_2$O, 121.47 MHz): δ 1.42 (d).

Example 17

2',3'-phenylacetaldehyde acetal-6-N-phenylurea adenosine 5'-monophosphate (compound 22)

2',3'-phenylacetaldehyde acetal adenosine 5'-monophosphate, tributylammonium salt (prepared according to example 14, 1.0 g, 2.15 mmol) was dissolved in N,N-dimethylformamide (10 mL) and phenylisocyanate (1.17 g, 10.72 mmol) added. The reaction was heated at 35° C. for 4 hrs, after which the solvent was removed and the residue partitioned between 1 M sodium bicarbonate (30 mL) and ethyl acetate (25 mL). The layers were separated and the product isolated from the aqueous layer via preparative HPLC. Yield=0.85 g (68%).

$^1$H NMR (D$_2$O, 300 MHz): δ 2.97 (d, 2H), 3.81 (m, 2H), 4.31 (m, 1H), 4.78 (m, 1H), 4.98 (m, 1H), 5.23 (t, 1H), 5.63 (d, 1H), 6.74 (m, 1H), 6.96 (m, 4H), 7.19 (m, 5), 8.12 (s, 1H), 8.30 (s, 1H). $^{31}$P NMR (D$_2$O, 121.47 MHz): δ 1.19 (s).

Example 18

2',3'-cinnamyl acetal-6-N-ethylurea adenosine 5'-monophosphate (Compound 27)

Compound 27 was prepared according to example 16, starting with 2'3' cinnamyl acetal adenosine 5'-monophosphate (Example 16) and substituting ethyl isocyanate for phenylisocyanate. Yield=65%.

$^1$H NMR (D$_2$O, 300 MHz): δ 1.07 (t, 3H), 3.21 (q, 2H), 3.93 (m, 2H), 4.45 (m, 1H), 4.99 (m, 1H), 5.28 (m, 1H), 5.54 (d, 0.3H), 5.70 (d, 0.7H), 5.95 (m, 1H), 6.14 (m, 1H), 6.61 (dd, 1H), 7.14 (m, 5H), 8.29 (m, 2H). $^{31}$P NMR (D$_2$O, 121.47 MHz): δ 1.93 (d).

Example 19

Trans-2',3'-cinnamyl acetal-6-N-ethylurea adenosine 5'-monophosphate (compound 41)

Compound 41 (trans-2',3'-cinnamyl acetal-6-N-ethylurea adenosine 5'-monophosphate) was obtained by the separation of the two diastereomers contained within Compound 27 (Example 18) by HPLC. Compound 41 is typically converted to the bis-sodium salt form to enhance its isolation from solution and to increase the stability of the resultant dry powder.

HPLC Method: Column: Phenomenex Synergi Polar RP, 4 μm, 80 angstrom, 150×3.0 mm; Mobile Phase: 0.1 M ammonium acetate buffer, pH=5:acetonitrile (70:30); Detection: UV, 254 nm; Column temperature: RT; Flow Rate: 1.5 mL/min; Retention time of Compound 41=6.4 min.

Example 20

NMR data of trans-2',3'-cinnamyl acetal-6-N-ethylurea adenosine 5'-monophosphate (Compound 41)

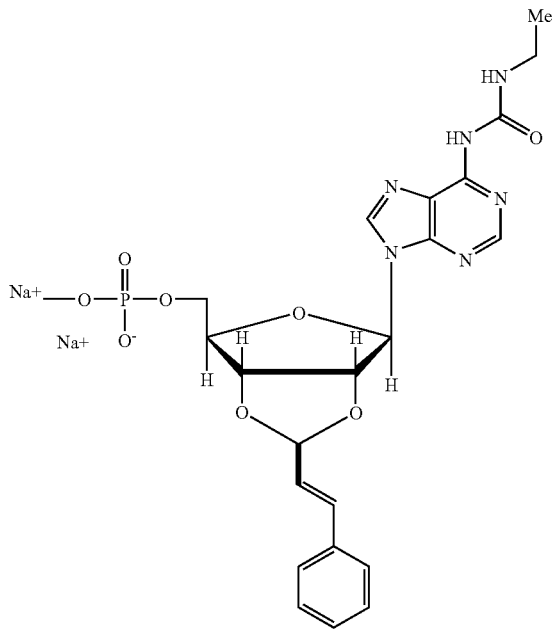

Chemical Name: Phosphoric acid mono-{6-[6-(3-ethyl-ureido)-purin-9-yl]-2-styryl-tetrahydro-furo[3,4-d][1,3]dioxol-4-ylmethyl} ester bis sodium salt
Molecular Formula: $C_{22}H_{23}N_6Na_2O_8P$
Molecular Weight: 576.41

$^1$H NMR (D$_2$O, 300 MHz): δ 1.11 (t, 3H, J=7.3 Hz), 3.24 (q, 2H, J=3.27 Hz), 3.90 (d, 2H), 4.49 (m, 1H), 4.99 (m, 1H), 5.07 (dd, 1H, J=3.3 Hz), 5.32 (dd, 1H, J=6.4 Hz), 5.79 (d, 1H, J=6.6 Hz), 6.02 (dd, 1H, J=6.6 and 16.0 Hz), 6.18 (d, 1H, J=3.7 Hz), 6.62 (d, 1H, J=16.0 Hz), 7.14-7.23 (m, 5H), 8.33 (s, 1H), 8.47 (s, 1H). $^{13}$C NMR (D$_2$O, 121 MHz): 14.2, 63.9, 80.24, 83.54, 83.9, 87.83, 119.23, 142.11, 149.27, 149.34, 150.87 $^{31}$P NMR (D$_2$O, 75 MHz): δ 5.168 (s). Optical rotation=−0.201° at a concentration of 5 mg/mL in water (specific rotation =−50.4°)

Example 21

Compounds 31-47

2', 3'-phenyl acetal adenosine 5'-monophosphate was prepared from the reaction between adenosine 5'-monophosphate, free acid, and benzaldehyde in trifluoroacetic acid according to Example 15; the yield was 82%.

2',3'-phenyl acetal adenosine 5'-monophosphate was further elaborated into Compounds 36-40. Compound 36 was prepared by acylation of the adenine 6 position with the ethyl isocyanate according to the general method of Example 16. Compounds 37-40 are derived from the reaction between 2',3'-phenyl acetal adenosine 5'-monophosphate and an appropriate isocyanate (propyl, butyl, hexyl, and cyclopentyl, respectively).

Similarly, Compounds 31, 32, 33, and 35 were prepared first by reacting adenosine 5'-monophosphate, free acid and phenylpropargyl aldehyde in formic acid (35% yield), followed by acylation of the adenine 6 position with the appropriate isocyanate (phenyl, hexyl, butyl, or ethyl respectively). Compound 34 is prepared from 2',3'-phenylpropargyl acetal adenosine 5'-monophosphate and propyl isocyanate. Compounds 42 and 43 were obtained by separation of the two diastereomers contained in the mixture compound 36, as previously described for compound 41. The dinucleoside diphosphates 45, 46, and 47 were prepared according to the method of example 21, via the self-condensation of their corresponding nucleoside monophosphates (27, 35, 24, and 36, respectively). Likewise, compound 44 is prepared according to the same method via the self-condensation of compound 27. Alternately, the diastereomerically-pure versions of dinucleoside diphosphates 44-47 are prepared by the self-condensation of the diastereomerically-pure mononucleoside monophosphates, such as compounds 41-43.

Example 22

P$^1$, P$^4$-Di-(2',3'-phenyl acetal-6-N-ethylurea adenosine 5'-) diphosphate (compound 47)

2',3'-phenylacetal-6-N-ethylurea adenosine 5'-monophosphate (compound 36, as its ammonium salt, 24.0 g, 45.9 mmol) was dissolved in dry pyridine (100 mL). The solution was reduced to half its volume by distillation under reduced pressure to remove water, and a further 50 mL of pyridine was added. Methyl chloroformate (6.0 mL, 77.7 mmol) was added in 5 equal portions (1.2 mL each) over 20 min, and the reaction mixture heated at 50° C. for 3 hrs, followed by 35° C. overnight. The solvent was removed and the residue dissolved in water (250 mL) and 1 M sodium bicarbonate (60 mL). The mixture was heated at 55° C. for 10 min, after which diethyl ether was added. The layers were separated and the product in the aqueous layer was purified by repeated injections onto preparative HPLC (Waters NovaPak C$_{18}$, 40×200 mm column, gradient from 0.05 M NH$_4$OAc (pH 6) to methanol) The yield of the title compound was 14.4 g. (61%)

$^{31}$P NMR (D$_2$O, 121.47 MHz): δ−10.1 (m).

Example 23

Coating of a Stent with a Polymer Incorporating a P2Y$_{12}$ Antagonist Compound A stent is coated with a P2Y$_{12}$ antagonist compound with procedures modified from that described in Example 4 of U.S. Pat. No. 6,908,624 (Hossainy). A stent is suspended in isopropanol and cleaned in an ultrasonic bath for 30 minutes. The stent is dried and cleaned in a plasma chamber. A poly (ethylene-vinyl alcohol) solution is made by dissolving one part poly(ethylene-vinyl alcohol) in seven parts dimethylsulfoxide, with stirring and shaking at 60° C. for 24 hours. A P2Y$_{12}$ antagonist compound (for example compound 41; typically in the range of 2-10% by weight of the total) is added to the poly(ethylene-vinyl alcohol)/dimethyl sulfoxide solution and the solution is mixed, vortexed and placed in a tube. The stent is attached to a mandrel wire and dipped into the solution. The coated stent is briefly passed over a hotplate at 60° C., then is cured for 6 hours at ambient temperature, after which it is dried for 24 hours in a vacuum oven at 40-60° C. The above process is repeated two or three times to give two or three layers. Following final drying, the stent is optionally sterilized by electron beam radiation.

Example 24

Platelet Aggregation Assays

Blood was collected from healthy volunteers into syringes containing ⅙ final blood volume of anti-coagulant ACD (65 mM citric acid, 85 mM sodium citrate, 110 mM dextrose) for washed platelet (WP) preparation or into a syringe containing a final concentration of 10 units/mL heparin or 300 µM PPACK for whole blood (WB) assays. The blood collected for whole blood assays was maintained at room temperature and immediately tested as described below. The blood collected for WP was centrifuged at 180 g for 15 minutes and the supernatant (platelet rich plasma) was removed. The platelet rich plasma was centrifuged and the platelets were pelleted and resuspended in a buffer consisting of (mM): NaCl (137), KCl (2.7), CaCl$_2$ (2) MgCl$_2$ (1), NaH$_2$PO$_4$ (3), Glucose (5), HEPES (10), pH 7.4, 0.2% BSA. These centrifugations and washes were repeated twice following by resuspension in the media described above containing 0.25 U apyrase/mL. Platelet aggregation was measured using the optical mode of a CHRONOLOG® aggregometer (Havertown, Pa.). Five hundred µl of platelet suspension containing 1 mg/mL Fibrinogen were warmed to 37° C. and stirred at 1000 rpm. Indicated concentrations of ADP were added to the sample and aggregation was monitored for 8 minutes. The effect of the compounds described in this invention were studied following the same protocol with the exception that the inhibitor was incubated for 2-5 minutes prior to the addition of a maximally effective concentration of ADP. For whole blood aggregation, blood was diluted 1:1 with saline and then aggregation was performed in the same manner as described above using the impedance mode of the aggregometer. The potency of agonists and inhibitors of platelet aggregation was calculated from both, the rate of aggregation and the maximal extent of aggregation obtained for each determination by fitting the data to a four-parameter logistic equation using the GRAPH-PAD® software package (GraphPad Corp. San Diego, Calif.).

The ability of $P2Y_{12}$ antagonists to inhibit platelet aggregation is presented in this application as the percent inhibition of the aggregation induced by a maximally effective concentration of ADP. When a broad range of concentrations of $P2Y_{12}$ antagonist was tested (usually from 1 nM to 100 µM), an $IC_{50}$ value was also obtained. $IC_{50}$ values represent the concentration of antagonist needed to inhibit by 50% the aggregation elicited by a given concentration of ADP.

Example 25

Effect of Different Compounds on ADP-Induced Aggregation

Different compounds were tested for their inhibition of ADP-induced aggregation and their $IC_{50}$ according to the protocols in Example 19; the results are shown in FIG. 1. The bar graphs in the figure illustrate the effect of 100 µM concentration of the compound on ADP-induced platelet aggregation, and the data are expressed as % inhibition of the ADP response.

FIG. 1 shows the structure and abbreviated name of each compound and its activity. Where hydrogens are understood to be present, they have been omitted for the sake of simplicity. For example, for the first structure of the figure, it is implied that there are hydrogens at the 3-position of the pyrimidine ring, at the 3'-position of the ribose on the oxygen, and on the nitrogen of the carbamate at the 2'-position of the ribose. In addition, as disclosed within the scope of the present invention, it is implied that the oxygens that are not doubly bonded to the phosphorous atoms are either present in the ionized form as salts with a counterion, or are bonded to a hydrogen atom. For simplicity, some of the structures in the figure are portrayed in the salt form, but this should not be interpreted as excluding the possibility that hydrogens could be present instead.

Several parent compounds, Up4U, Ip4U, Up3U, and Cp4U, without modifications on the furanose hydroxyl groups, have been included at the end of the figure to illustrate the utility of the present invention. However, these unmodified parent compounds do not inhibit the ADP-induced aggregation and are not within the scope of the present invention.

Example 26

Calcium Mobilization Assay

For calcium mobilization assays, cells expressing $P2Y_1$, $P2Y_2$, and $P2Y_6$ were seeded in black wall/clear bottom cell culture plates (Corning Inc., Corning, N.Y.), and assays were conducted 48 hours after plating. On the day of the assay, the growth medium was aspirated and replaced with a solution of Fluo-3 AM (2.5 µM final concentration) in an assay buffer consisting of (mM): KCl (10.0), NaCl (118), $CaCl_2$ (2.5), $MgCl_2$ (1.0), HEPES (20), glucose (10), pH 7.4. After 60-minute incubation with Fluo-3 AM at 25° C., cells were washed free of dye. Cells were treated with different concentrations of test compound followed 1-2 minutes later with the addition of a maximally effective concentration of the cognate receptor agonist. Intracellular calcium levels in response to the treatment of cells with the test compound and the receptor agonist were continuously monitored in each well simultaneously by measuring the changes in fluorescence intensity using the a fluorescence imaging plate reader (FLIPR®, Molecular Devices Corp., Sunnyvale, Calif.). The results of this assay are presented in Table I.

Example 27

Effect of Different Compounds on ADP-Induced Aggregation and on Activation of P2Y Receptors Various compounds were tested for their effects on inhibition of ADP-induced platelet aggregation using the washed platelet preparation as described in Example 24. In addition, the effects of these compounds on the activation of $P2Y_1$, $P2Y_2$, $P2Y_4$, and $P2Y_6$ receptors were estimated according the calcium mobilization described in Example 23. The results are shown in Table 1. All compounds tested showed no response (NR) at $P2Y_1$, $P2Y_2$, $P2Y_4$, and $P2Y_6$ receptors. Data presented are from the average of at least two separate experiments.

TABLE 1

| Compound # | Platelet Aggregation $IC_{50}$ (nM) | Calcium Mobilization | | | |
|---|---|---|---|---|---|
| | | $P2Y_1$ | $P2Y_2$ | $P2Y_4$ | $P2Y_6$ |
| 22 | 160 ± 27 | NR | NR | NR | NR |
| 23 | 53 ± 16 | NR | NR | NR | NR |
| 24 | 41 ± 7 | NR | NR | NR | NR |
| 25 | 36 ± 9 | NR | NR | NR | NR |
| 26 | 36 ± 9 | NR | NR | NR | NR |
| 27 | 9 ± 3 | NR | NR | NR | NR |
| 28 | 209 | NR | NR | NR | NR |
| 31 | 230 | NR | NR | NR | NR |
| 32 | 210 | NR | NR | NR | NR |
| 33 | 67 | NR | NR | NR | NR |
| 35 | 25 | NR | NR | NR | NR |
| 36 | 13 ± 3 | NR | NR | NR | NR |
| 41 | 13 ± 2 | NR | NR | NR | NR |
| 42 | 12 | NR | NR | NR | NR |
| 43 | 11 | NR | NR | NR | NR |
| 45 | 10 | NR | NR | NR | NR |
| 46 | 53 | NR | NR | NR | NR |
| 47 | 55 | NR | NR | NR | NR |

Example 28

Effects of Compounds on Platelet Aggregation In Vivo

To evaluate the ability of these compounds to inhibit platelet aggregation in vivo, an experimental protocol similar to the method of R. G. Humphries et al. (*Br. J. Pharmacol.* 115:1110-1116, 1995) will be performed.

Surgical Preparation and Instrumentation: Male Sprague-Dawley rats are anesthetized. Body temperature is maintained at 37±0.5° C. with a heating lamp. Animals breathe spontaneously and a tracheotomy is performed to ensure a patent airway. A cannula containing heparinized saline is introduced into the left femoral artery and connected to a transducer to record blood pressure and heart rate. Cannulae containing non-heparinized saline are introduced into the left common carotid artery and left jugular vein for withdrawal of arterial blood samples and i.v. administration of compounds, respectively. Experimental Protocol: Either compound or vehicle is administered to each animal as an infusion. Blood samples are taken immediately prior to the first infusion, at the end of each infusion and 20 min after cessation of the final infusion for measurement of platelet aggregation ex vivo.

Immediately after sampling, ADP-induced platelet aggregation is measured in duplicate in 0.5 ml blood samples diluted 1:1 with saline and incubated at 37° C. for 4 min. For the final minute of this period, cuvettes are transferred to aggregometer and the sample stirred at 900 rpm. ADP (3 μM) is added in a volume of 20 μl and the aggregation response is recorded.

Example 29

Inhibition of Thrombus Formation in Anesthetized Rats

To evaluate the effect of these compounds on thrombus formation in vivo, the following experimental protocol is performed.

Rats (CD-1; male; approximately 350 grams; Charles River, Raleigh, N.C.), are anesthetized with sodium pentobarbital (70 mg/kg i.p.). The abdomens are shaved and a 22 gauge intravenous catheter is inserted into a lateral tail vein. A midline incision is made and the intestines are wrapped in saline-soaked gauze and positioned so the abdominal aorta is accessible. The inferior vena cava and abdominal aorta are carefully isolated and a section (approx. 1 cm) of the abdominal aorta (distal to the renal arteries proximal to the bifurcation) is dissected. All branches from the aorta in this section are ligated with 4-0 silk suture. A 2.5 mm diameter flow probe connected to a TRANSONIC® flow meter is placed on the artery and a baseline (pre-stenosis) flow is recorded. Two clips are placed around the artery decreasing the vessel diameter by approximately 80%. A second baseline flow measurement is taken (post-stenosis) and the hyperemic response is tested. Animals are then treated with either compound or saline i.v., via tail vein catheter. Thrombosis is induced five minutes after treatment by repeated external compressions of the vessel with hemostatic forceps. Two minutes post-injury, the vessel compressions are repeated and a 10-minute period of flow monitoring is started. Animals are monitored continuously for a minimum of the first ten minutes post-injury. After twenty minutes (post-injury), a flow measurement is repeated and the animals are euthanized. The section of the aorta that includes the injured section is harvested and placed in 10% formalin for possible histologic evaluation.

Example 30

Inhibition of Thrombus Formation in Anesthetized Dogs

To evaluate the effect of these compounds on dynamic thrombus formation in vivo, the following experimental protocol similar to the method of J. L. Romson et al. (*Thromb. Res.* 17:841-853, 1980) is performed.

Surgical Preparation and Instrumentation: Briefly, purpose-bred dogs are anesthetized, intubated and ventilated with room air. The heart is exposed by a left thoracotomy in the fifth intercostal space and suspended in a pericardial cradle. A 2-3 cm segment of the left circumflex coronary artery (LCCA) is isolated by blunt dissection. The artery is instrumented from proximal to distal with a flow probe, a stimulation electrode, and a Goldblatt clamp. The flow probe monitors the mean and phasic LCCA blood flow velocities. The stimulation electrode and its placement in the LCCA and the methodology to induce an occlusive coronary thrombus have been described previously (J. K. Mickelson et al., *Circulation* 81:617-627, 1990; R. J. Shebuski et al., Circulation 82:169-177, 1990; J. F. Tschopp et al., Coron. Artery Dis. 4:809-817, 1993).

Experimental Protocol: Dogs are randomized to one of four treatment protocols (n=6 per treatment group) in which the control group receives saline i.v. and the three drug-treated groups are administered compound i.v. Upon stabilization from the surgical interventions, dogs receive either saline or compound. After approximately 30 minutes, an anodal current is applied to the LCCA for 180 min. The number and frequency of cyclic flow variations (CFV) that precede formation of an occlusive thrombus are recorded. These cyclic phenomena are caused by platelet thrombi that form in the narrowed lumen as a result of platelet aggregation (J. D. Folts et al., Circulation 54:365-370, 1976; Bush et al., Circulation 69:1161-1170, 1984). Zero flow in the LCCA for a minimum of 30 minutes indicates a lack of antithrombotic efficacy (L. G. Frederick et al., *Circulation* 93:129-134, 1996).

Example 31

Dose-Dependent Inhibition of Platelet Aggregation in Mice

In order to evaluate the effects of inhibition of platelet aggregation in-vivo by the compounds described in this invention, experimental protocols similar to those described by Leon et al. (*Circulation* 103:718-723, 2001) were performed.

Anesthetized mice were injected intravenously with either saline or with different doses of trans-2',3'-cinnamyl acetal-6N-ethylurea adenosine 5'-monophosphate, bis sodium salt (Compound 41), usually between 1 and 100 μg/kg. Five minutes after the administration of the compound, 700 μL of blood were obtained from each animal. The blood of two animals was combined and immediately processed to obtain platelet rich plasma for the assessment of platelet aggregation stimulated by 1 and 5 μM ADP. Platelet aggregation was measured using optical aggregometry as described in Example 21. The $P2Y_{12}$ receptor antagonists described here and tested in this ex-vivo model produced a dose-dependent inhibition of platelet aggregation.

Example 32

Figures 1, 2:
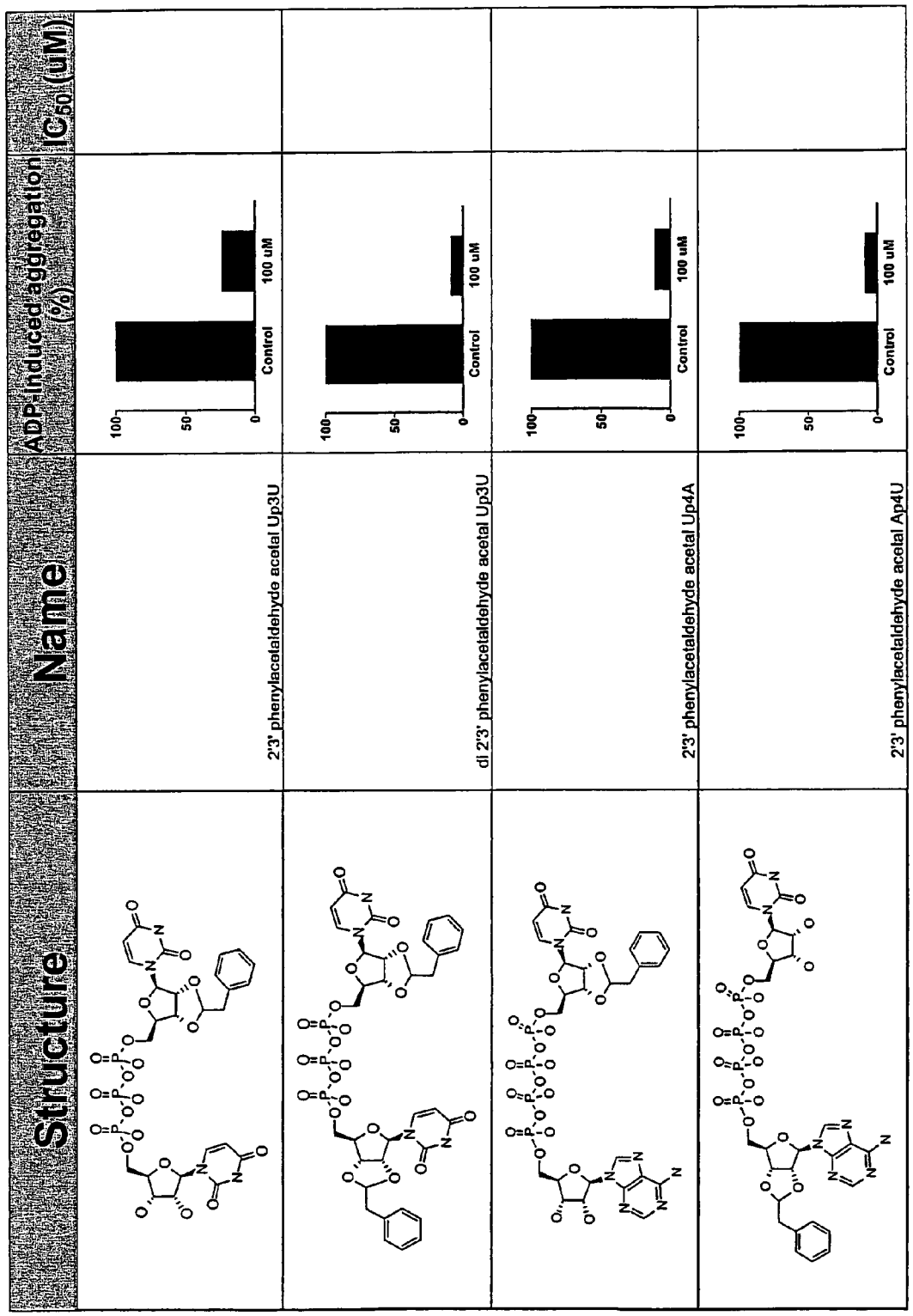
FIG. 2 shows the kinetics of inhibition of ADP-induced aggregation following intravenous administration of 2'3'-(trans)cinnamyl acetal-6-N-ethylurea AMP (compound 41, INS50589) in mice.

Reversible Inhibition of Platelet Aggregation by $P2Y_{12}$ Receptor Antagonists in Mice A key characteristic of the compounds described in this invention is the reversible nature of the inhibition of platelet aggregation. The model system described in Example 28 was also used to study the kinetics of in-vivo inhibition of platelet aggregation with selected compounds. Briefly, a maximally effective concentration of test compound was administered intravenously, and blood samples were obtained before and at different times (usually 0, 1, 5, 15 and 30 minutes) after the administration of trans-2',3'-cinnamyl acetal-6N-ethylurea adenosine 5'-monophosphate, bis sodium salt (Compound 41). Blood samples were processed immediately and aggregation induced by 1 μM and 5 μM ADP was estimated as described in Example 31. Complete inhibition of ADP-induced platelet aggregation was observed five minutes after administration of the test compound, and by 30 minutes the aggregation response to ADP returned to values similar to those observed in control animals, suggesting that the effect of the test compound in mice is reversible (FIG. 2).

Example 33

Figures 1, 2, 3:
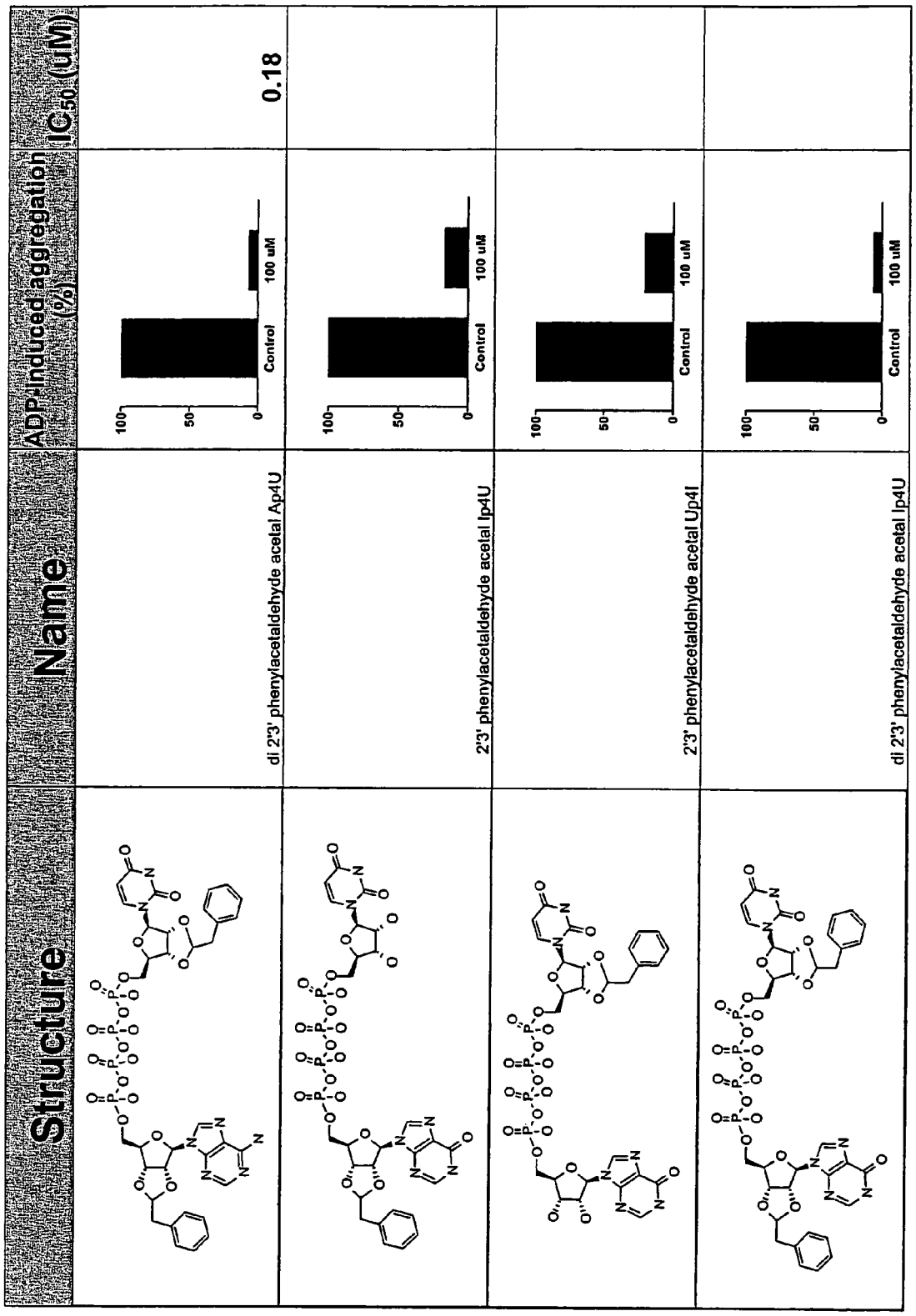
FIG. 3 shows the protection against thromboembolism-induced mortality in mice by the treatment with INS50589.

Prevention of Thromboembolism-Iinduced Mortality in Mice by the Treatment with $P2Y_{12}$ Receptor Antagonists Ten anesthetized mice were treated with vehicle (control) or with a single bolus intravenous administration of test compound (usually between 10 and 25 mg/kg). Five minutes after treatment, the animals were injected with a mixture of 0.3 mg/kg collagen and 60 μg/kg epinephrine. The survival time after the administration of collagen and epinephrine in animals pretreated with saline or 25 mg/kg of the test compound 2'3'-(trans)cinnamyl acetal-6-N-ethylurea AMP (compound 41), are shown using the Kaplan-Meier plot in FIG. 3. Ninety percent of the vehicle-pretreated animals died within 6 minutes after the IV injection of collagen and epinephrine. In contrast, mortality resulting from systemic intravascular thromboembolism was observed in only 20% of the animals pretreated with the test compound (FIG. 3). These results demonstrate a significant antithrombotic effect of the in vivo administration of compounds described in this invention.

Example 34

Inhibition of Platelet Aggregation by Administration of $P2Y_{12}$ Antagonists in Dogs Two weeks prior to the study, beagle dogs were implanted with jugular catheters and vascular access ports. Groups of four dogs (two of each sex) were fitted with jackets and connected to ambulatory infusion pumps for drug administration.

The day of the study, dogs were treated with a continuous infusion of different concentrations of test compound (usually between 0.1 and 1.5 mg/kg/h) for 90 minutes at a rate of 3 mL/kg/h. Approximately 30 minutes and 15 minutes prior to the start of infusion (predose samples), at different times during each infusion period (usually 10, 30, 60, and 90 minutes), and after the termination of the infusion (usually 5, 10, 20, 30, 40, 60, 120, and 240 minutes and 18, 20, 22, and 24 hours), blood was withdrawn from a cephalic vein catheter for the assessment of ex-vivo whole blood platelet aggregation assays and/or for bioanalytical determination of the plasma levels of the test compound. Platelet aggregation was estimated using the impedance mode of a CHRONOLOG® aggregometer as described in Example 24, and the plasma levels of the test compound were analyzed on an API 4000 LC/MS/MS system coupled with an Agilent 1100 series liquid chromatograph.

Figures 1, 2, 3, 4:
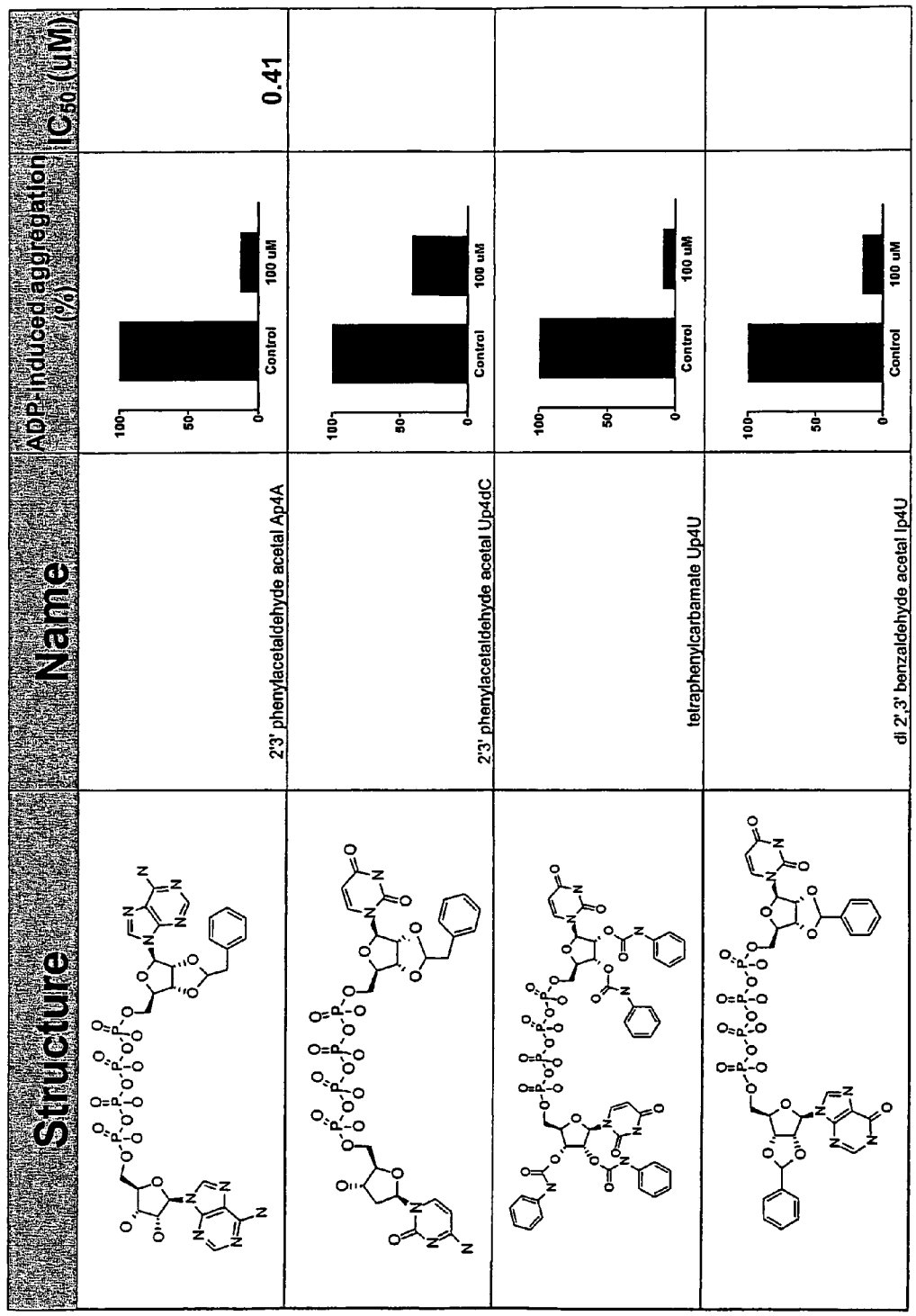
FIG. 4 shows the dose-dependent inhibition of platelet aggregation by continuous IV infusion of INS50589 in dogs.
Figures 1, 2, 3, 4, 5:
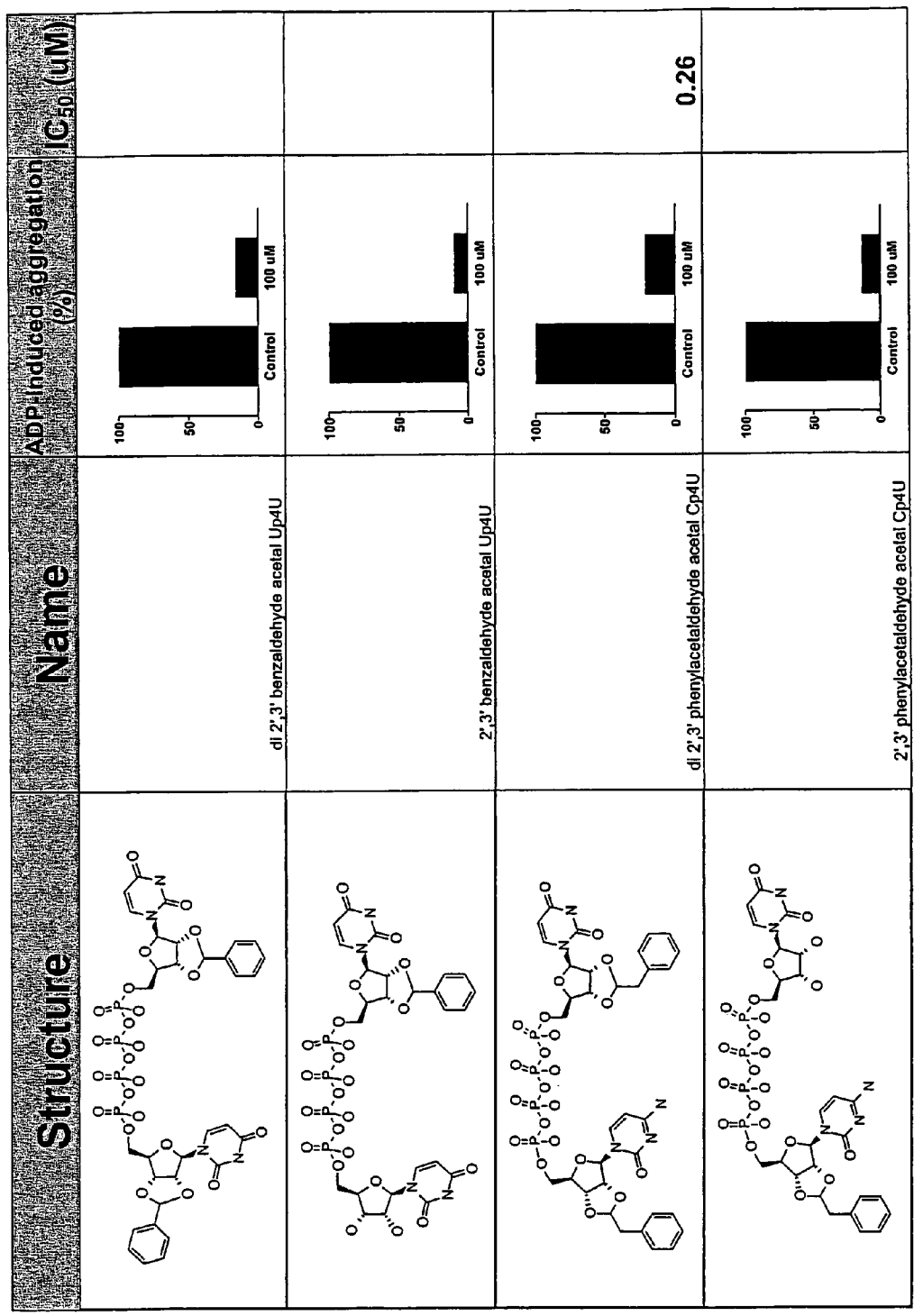
Figures 1, 2, 3, 4, 5, 6:
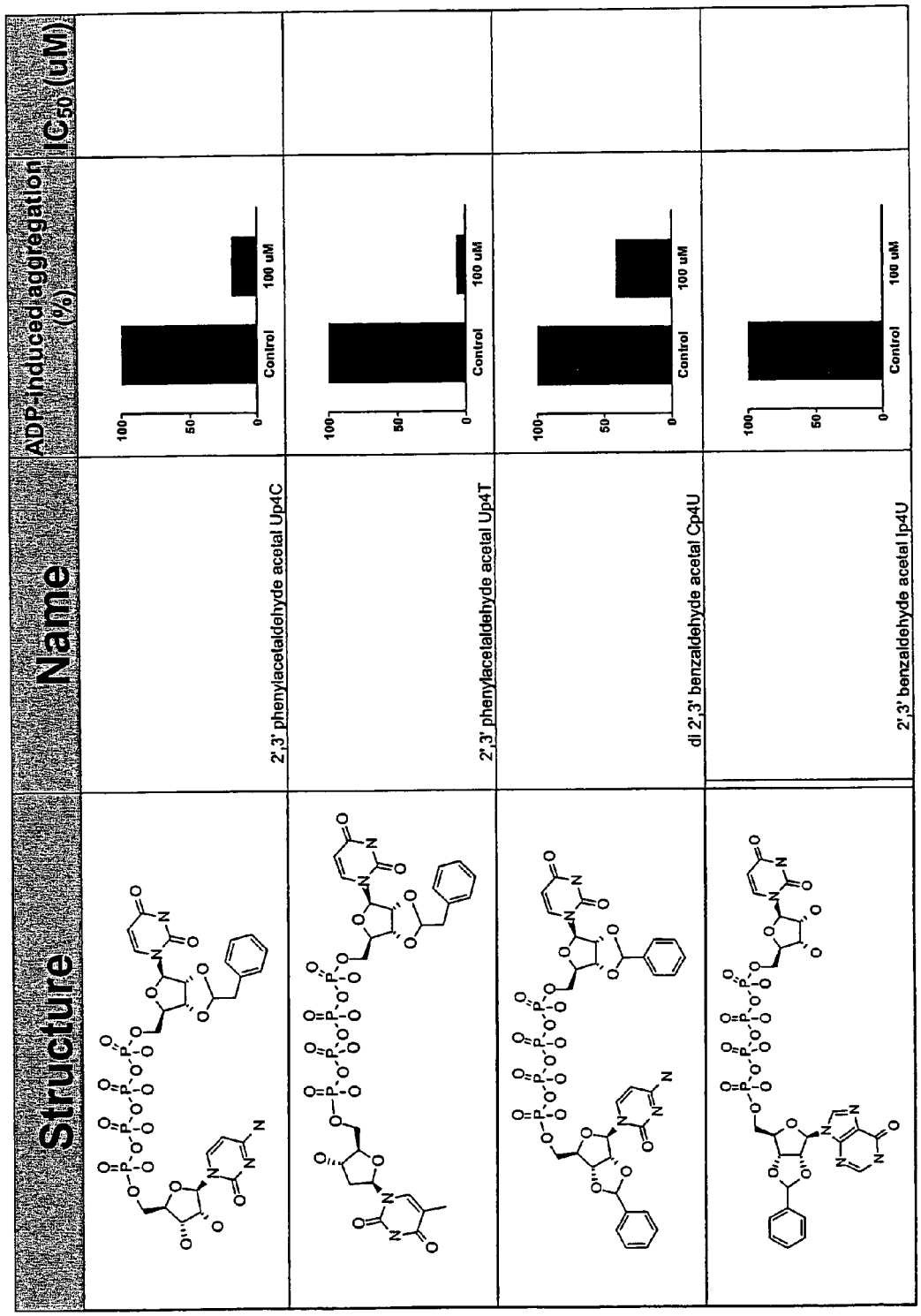
Figures 1, 2, 3, 4, 5, 6, 7:
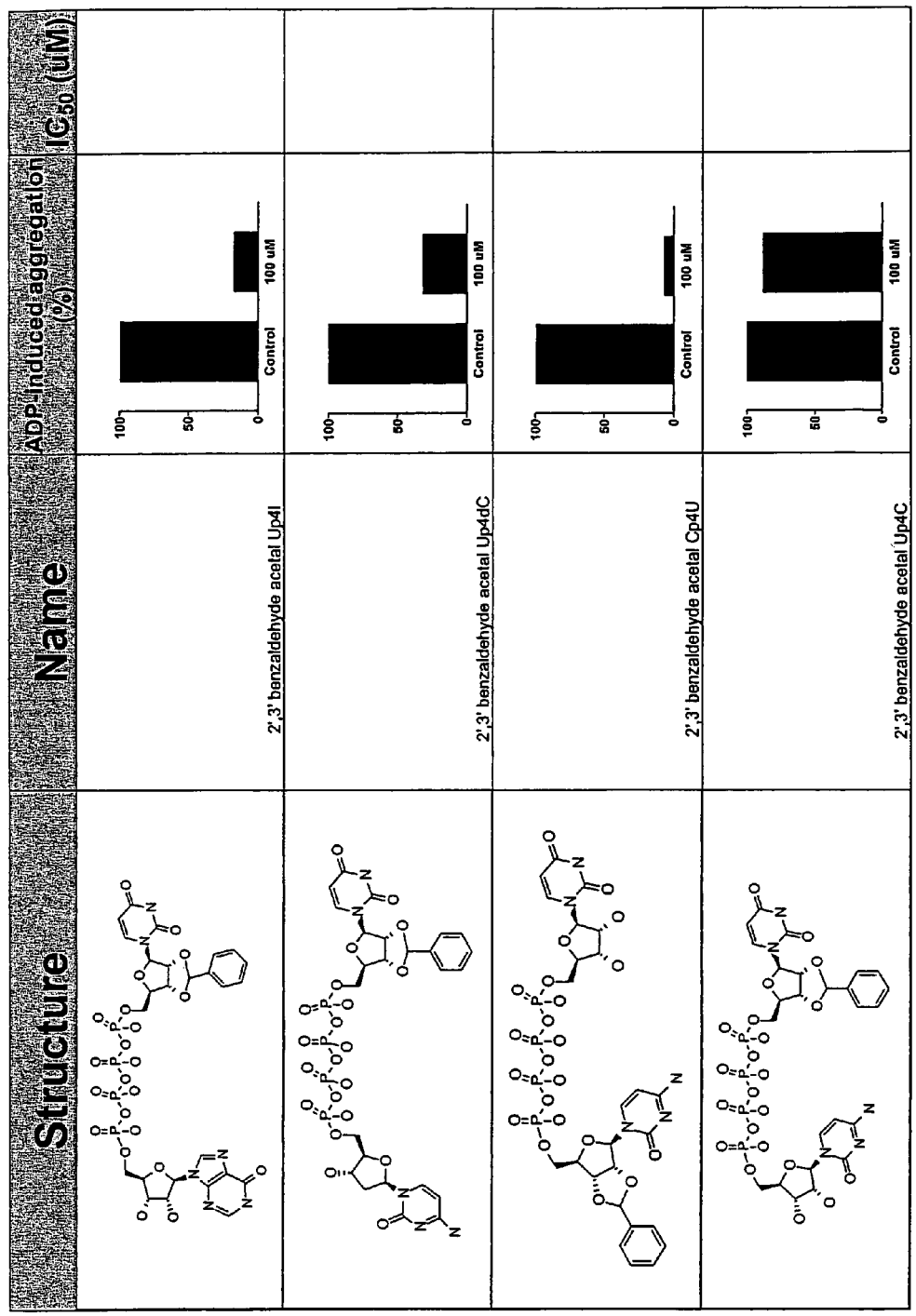
Figures 1, 2, 3, 4, 5, 6, 7, 8:
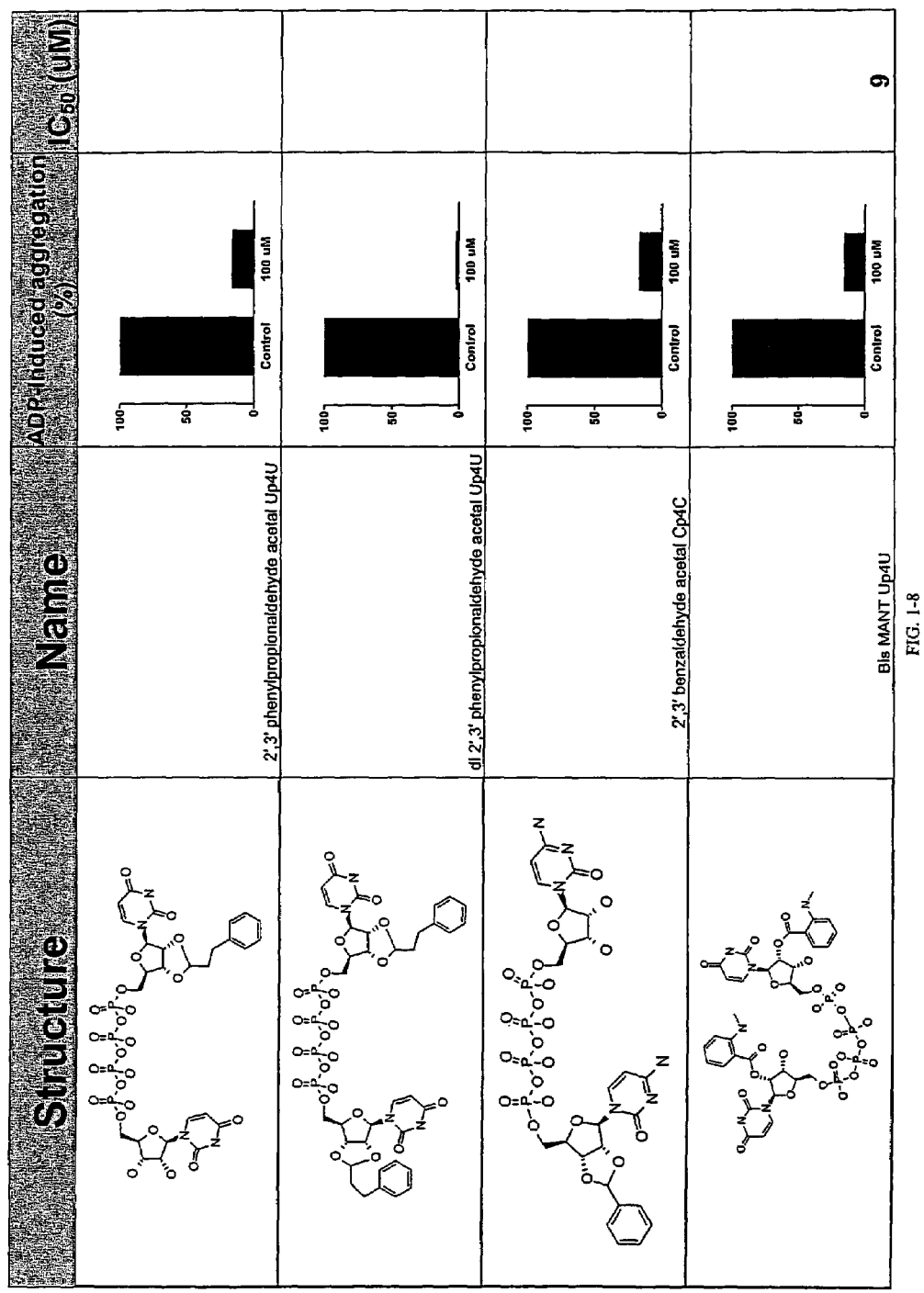
Figures 1, 2, 3, 4, 5, 6, 7, 8, 9:
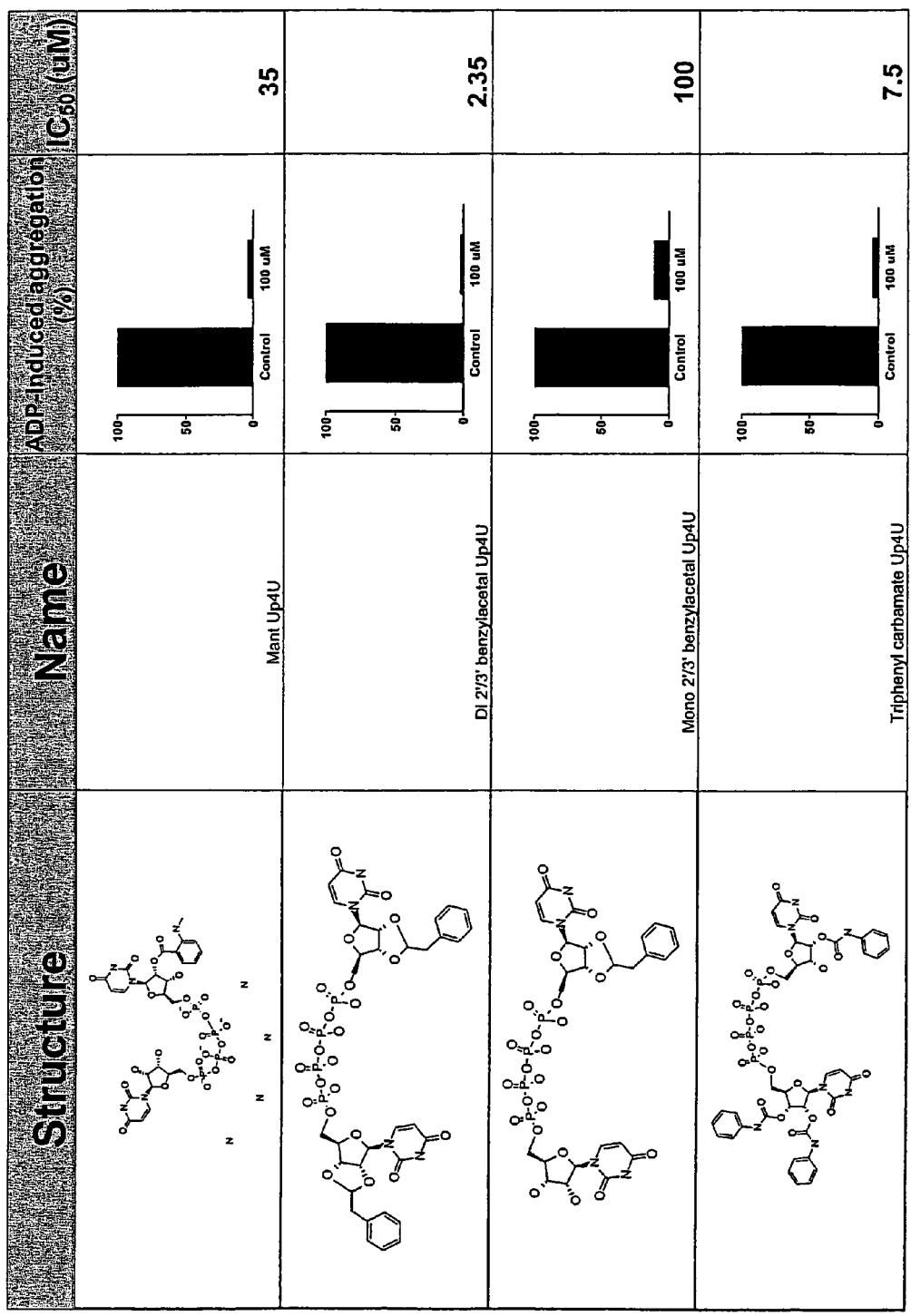
Figures 1, 2, 3, 4, 5, 6, 7, 8, 9, 10:
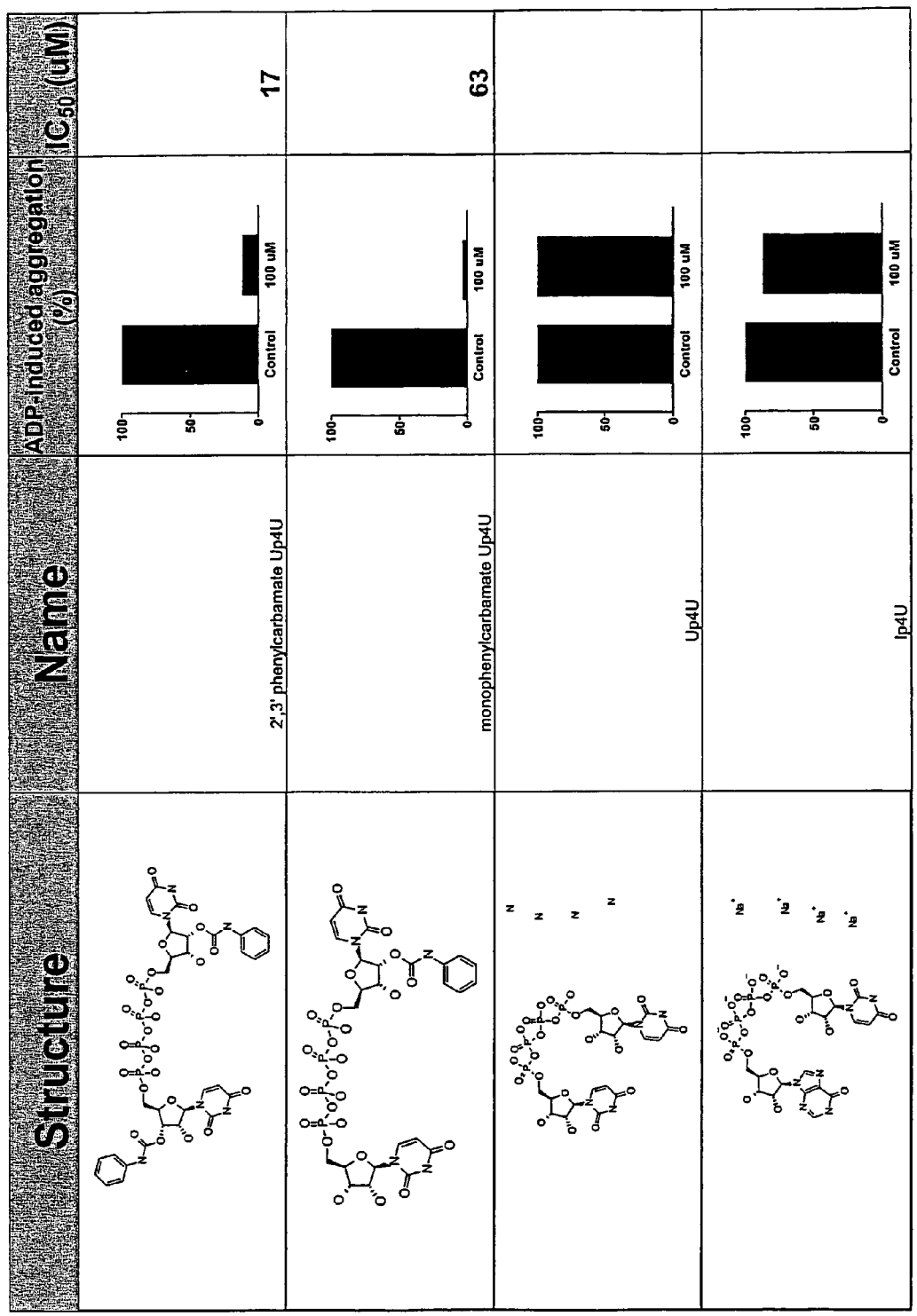
Figures 1, 2, 3, 4, 5, 6, 7, 8, 9, 10, 11:
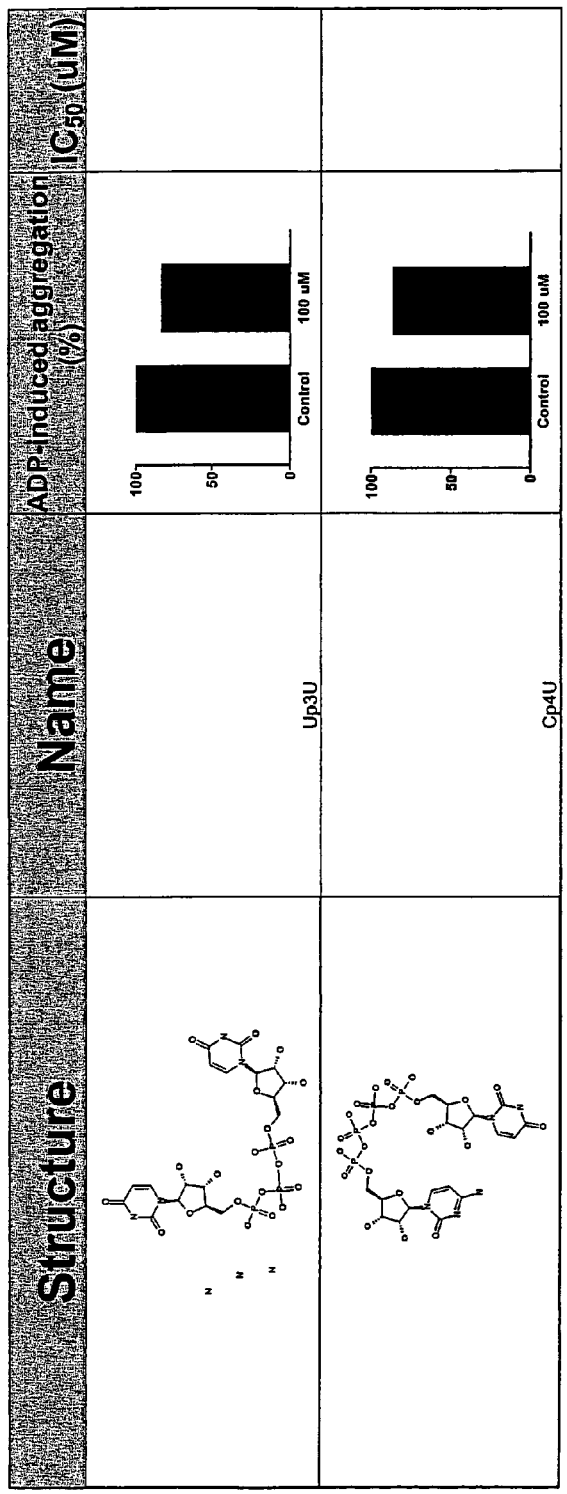
Figure 2:
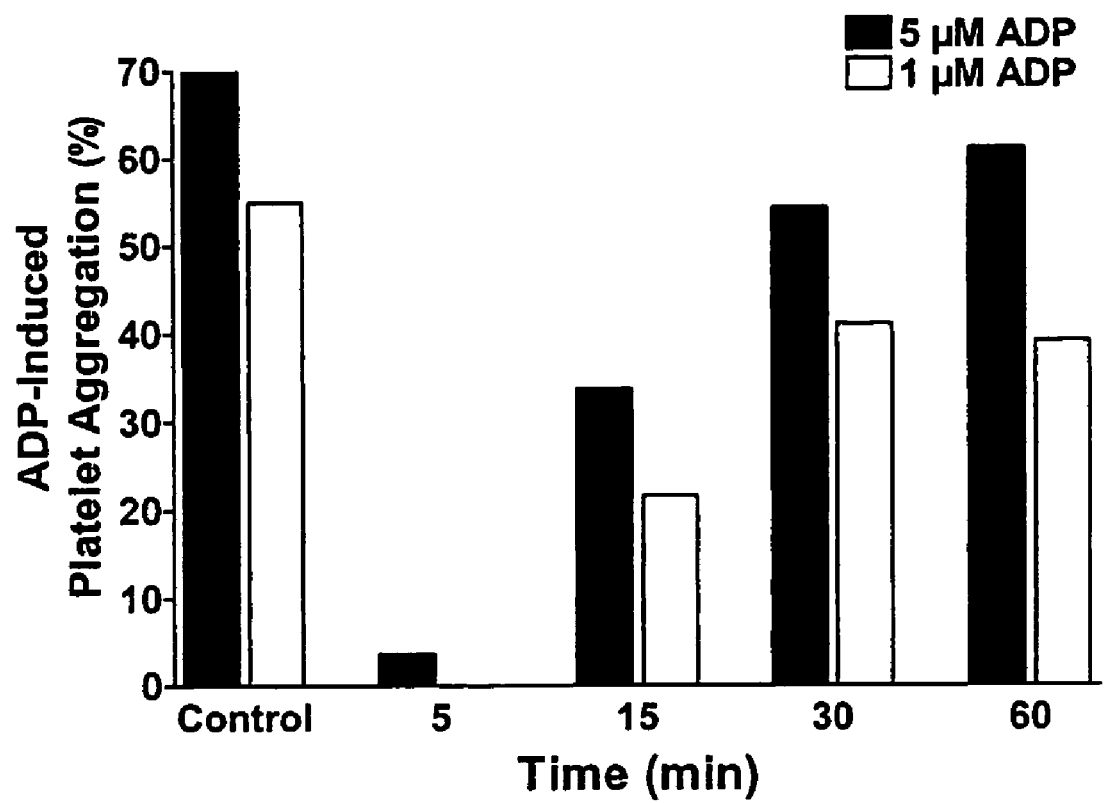
Figure 3:
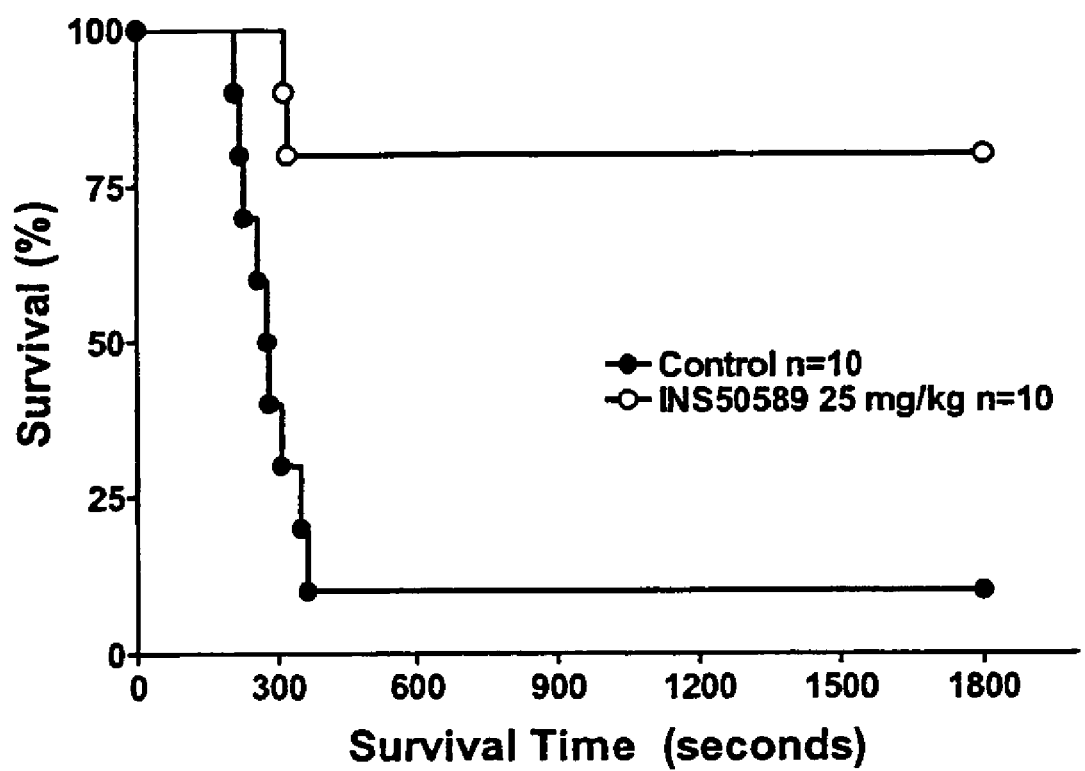
Figure 4:
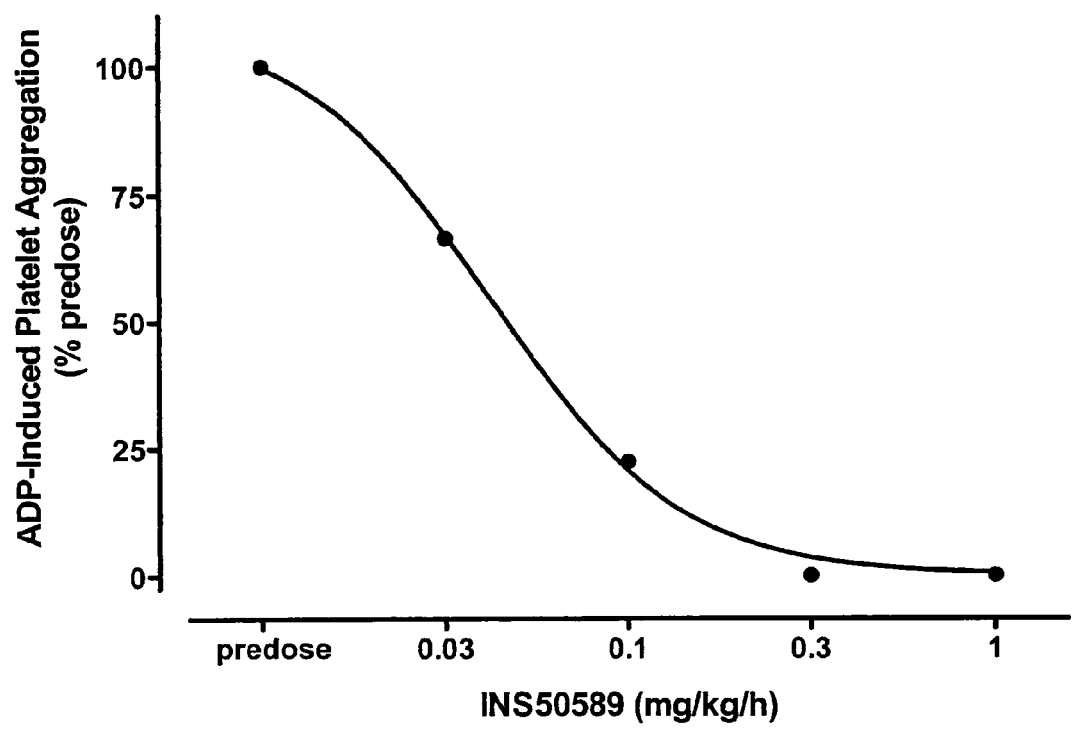

As illustrated in FIG. 4, continuous intravenous administration of 2'3'-(trans)cinnamyl acetal-6-N-ethylurea AMP (compound 41) produced a dose-dependent inhibition of platelet aggregation. The maximal inhibitory effect was observed with the administration of 0.3 mg/kg/h.

Figure 5A:
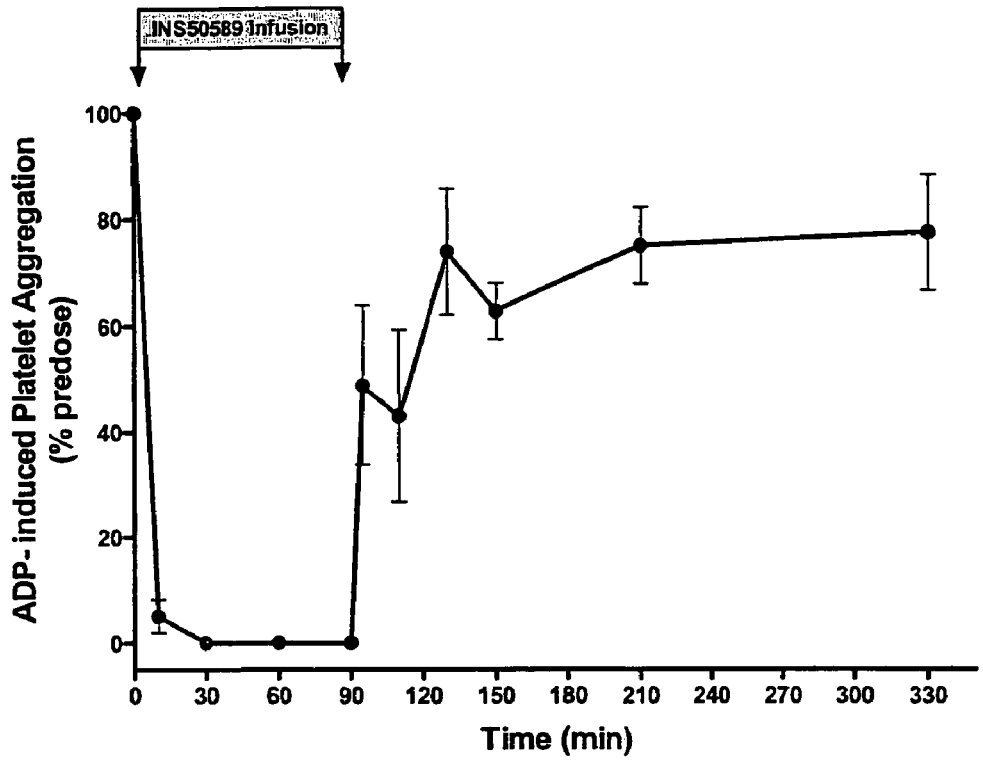
FIG. 5A shows the platelet aggregation at the indicated times during and after administration of INS50589 at 0.3 mg/kg/h in Dogs.

The kinetics and reversibility of the inhibition of platelet aggregation produced by the test compound were also studied. As illustrated in FIG. 5A, the pharmacodynamic effect of the test compound reached steady state by 30 minutes and the inhibition of platelet aggregation was rapidly reversed upon termination of the infusion. These results demonstrate the ability of the test compound to rapidly inhibit platelet aggregation within minutes of initiating continuous IV infusion, and to allow for nearly complete restoration of platelet aggregation within an hour following termination of infusion.

Figure 5B:
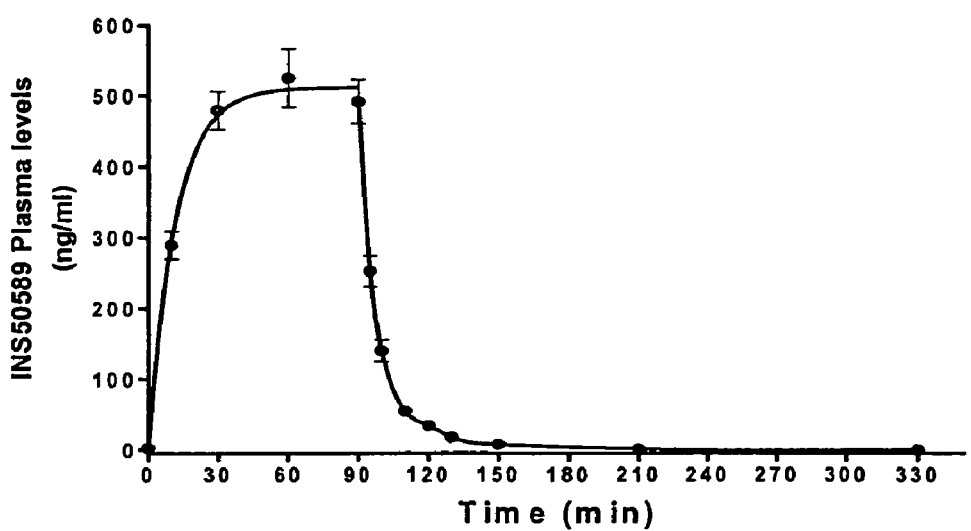
FIG. 5B shows the plasma levels of INS50589 at the indicated times during and after the infusion of INS50589.

The pharmacological effect of the administration of the test compound correlated closely with the plasma levels of the compound. Total plasma concentrations of the test compound reached steady state between 30 and 60 minutes and decreased rapidly after discontinuation of the administration of the compound. One-compartment model analysis of the plasma levels of the test compound after the end of infusion indicated that the compound was cleared from plasma with an estimated half-life of approximately 7 minutes, as illustrated in FIG. 5B.

In conclusion, the pharmacokinetic and pharmacodynamic profile of 2'3'-(trans)cinnamyl acetal-6-N-ethylurea AMP (compound 41) is consistent with a rapid onset and offset of action that results in a rapid and readily reversible control of platelet function.

Although the invention has been described with reference to the presently preferred embodiments, it should be understood that various modifications could be made without departing from the scope of the invention.

What is claimed:

1. A $P2Y_{12}$ receptor antagonist compound-eluting stent, wherein the stent is coated with one or more $P2Y_{12}$ receptor antagonist compound of general Formula I, or a pharmaceutically acceptable salt, solvate, or hydrate thereof; wherein a therapeutically effective amount of the compound is eluted to the local environment when the stent is placed in a vessel, Formula I

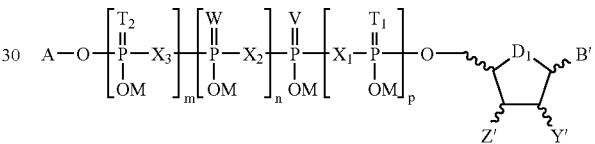

wherein:
- $X_1$, $X_2$, and $X_3$ are independently oxygen, methylene, monochloromethylene, dichloromethylene, monofluoromethylene, difluoromethylene, or imido;
- $T_1$, $T_2$, W, and V are independently oxygen or sulfur;
- m=0, 1 or 2;
- n=0 or 1;
- p=0, 1, or 2;
- where the sum of m+n+p is from 0 to 5;
- M=H, or a pharmaceutically-acceptable inorganic or organic counterion;
- $D_1$=O or $CH_2$;
- Y'=H, OH, or $OR_1$;
- Z'=H, OH, or $OR_2$; with the proviso that when A=M, at least one of Y' and Z' is $OR_1$, or $OR_2$;
- A=M, or
- A is a nucleoside residue which is defined as:

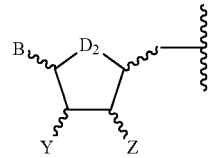

and which is linked to the phosphate chain via the 5'-position of the furanose or carbocycle;
wherein:
- $D_2$=O or $CH_2$;
- Z=H, OH, or $OR_3$;
- Y=H, OH, or $OR_4$;

with the proviso that at least one of Y', Z', Y and Z is equal to $OR_1$, $OR_2$, $OR_4$ or $OR_3$ respectively;

$R_1$, $R_2$, $R_3$, and/or $R_4$ are residues which are linked directly to the 2'- and/or 3'-hydroxyls of the respective furanose or carbocycle via a carbon atom according to Formula II, or linked directly to two (2'- and 3'-) hydroxyls of the respective furanose or carbocycle via a common carbon atom according to Formula III;

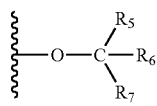

Formula II wherein:
O is the corresponding 2'- and/or 3'-oxygen of the respective furanose or carbocycle;
C is a carbon atom;
$R_5$, $R_6$, and $R_7$ are H, alkyl, cycloalkyl, aralkyl, aryl, substituted aralkyl, or substituted aryl, such that the moiety defined according to Formula II is an ether; or
$R_5$ and $R_6$ are H, an alkyl, cycloalkyl, aralkyl, aryl, substituted aralkyl, or substituted aryl, and $R_7$ is alkoxy, cycloalkoxy, aralkyloxy, aryloxy, substituted aralkyloxy, or substituted aryloxy such that the moiety defined according to Formula II is an acyclic acetal or ketal; or
$R_5$ and $R_6$ are taken together as oxygen or sulfur doubly bonded to C, and $R_7$ is alkyl, cycloalkyl, aralkyl, aryl, substituted aralkyl, or substituted aryl, such that the moiety defined according to Formula II is an ester or thioester; or
$R_5$ and $R_6$ are taken together as oxygen or sulfur doubly bonded to C, and $R_7$ is amino or mono- or disubstituted amino, where the substituents are alkyl, cycloalkyl, aralkyl, aryl, substituted aralkyl, or substituted aryl, such that the moiety according to Formula II is a carbamate or thiocarbamate; or
$R_5$ and $R_6$ are taken together as oxygen or sulfur doubly bonded to C, and $R_7$ is alkoxy, cycloalkoxy, aralkyloxy, aryloxy, substituted aralkyloxy, or substituted aryloxy, such that the moiety according to Formula II is a carbonate or thiocarbonate; or
$R_7$ is not present and $R_5$ and $R_6$ are taken together as oxygen or sulfur doubly bonded to C and both the 2'- and 3'-oxygens of the respective furanose or carbocycle are directly bound to C to form a cyclical carbonate or thiocarbonate;

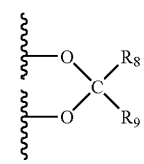

Formula III wherein:
the O atoms are the 2'- and 3'-oxygens of a furanose or carbocycle; and the 2'- and 3'-oxygens of the furanose or carbocycle are linked by a common carbon atom (C) to form a cyclical acetal, cyclical ketal, or cyclical orthoester;
for cyclical acetals and ketals, $R_8$ and $R_9$ are independently hydrogen, alkyl, cycloalkyl, aralkyl, aryl, substituted aralkyl, substituted aryl, or can be joined together to form a homocyclic or heterocyclic ring composed of 3 to 8 atoms, preferably 3 to 6 atoms; and
for cyclical orthoesters, $R_8$ is hydrogen, alkyl, cycloalkyl, aralkyl, aryl, substituted aralkyl, or substituted aryl, $R_9$ is alkyloxy, cycloalkyloxy, aralkyloxy, aryloxy, substituted aralkyloxy, or substituted aryloxy;
B and B' are independently a purine residue, as in Formula IV, linked through the 9-position, or a pyrimidine residue, as in Formula V, linked through the 1-position;

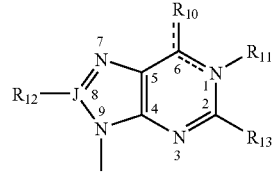

Formula IV

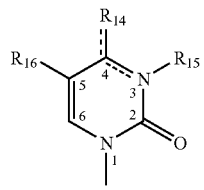

Formula V wherein:
$R_{10}$ and $R_{14}$ independently are hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or
$R_{10}$ and $R_{14}$ independently are acylamino according to Formula VI; or
when $R_{10}$ in a purine or $R_{14}$ in a pyrimidine has as its first atom nitrogen, $R_{10}$ and $R_{11}$ or $R_{14}$ and $R_{15}$ can be taken together to form a 5-membered fused imidazole ring to give an etheno compound, optionally substituted on the etheno ring with one or more alkyl, cycloalkyl, aralkyl, or aryl moieties;
J is carbon or nitrogen, with the provision that when J=nitrogen, $R_{12}$ is not present;
$R_{11}$ is hydrogen, oxygen, or is absent;
$R_{15}$ is hydrogen, or acyl;
$R_{12}$ is hydrogen, alkyl, bromo, azido, alkylamino, arylamino or aralkylamino, alkoxy, aryloxy or aralkyloxy, alkylthio, arythio or aralkylthio, or $\omega$-A($C_{1-6}$alkyl)B-, wherein A and B are independently amino, mercapto, hydroxy or carboxyl;
$R_{13}$ is hydrogen, chlorine, amino, monosubstituted amino, disubstituted amino, alkylthio, arylthio, or aralkylthio;
$R_{16}$ is hydrogen, methyl, alkyl, halogen, alkyl, alkenyl, substituted alkenyl, alkynyl, or substituted alkynyl;

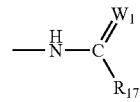

Formula VI wherein NH is the amino residue at the C-6 position in a purine or the amino residue at the C-4 position in a pyrimidine;

C is a carbon atom;
W₁ is oxygen or sulfur;
R$_{17}$ is amino or mono- or disubstituted amino, with the amino substituent being alkyl, cycloalkyl, aralkyl, or aryl, such that the moiety according to Formula VI is a urea or thiourea; or
R$_{17}$ is alkoxy, aralkyloxy, aryloxy, substituted aralkyloxy, or substituted aryloxy, such that the moiety according to Formula VI is a carbamate or thiocarbamate; or
R$_{17}$ is alkyl, cycloalkyl, aralkyl, or aryl, with or without substituents or heteroatoms, such that the moiety according to Formula VI is an amide.

2. The P2Y$_{12}$ receptor antagonist compound-eluting stent according to claim 1, wherein A=M.

3. The P2Y$_{12}$ receptor antagonist compound-eluting stent according to claim 2, wherein said compound is a compound of Formula Ib-1, or a pharmaceutically acceptable salt, solvate, or hydrate thereof;

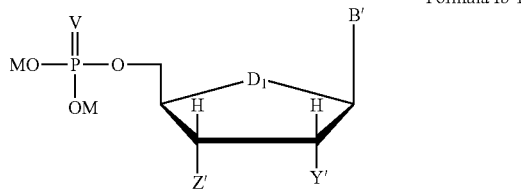

Formula Ib-1 wherein:
V=O;
M=H or a pharmaceutically-acceptable inorganic or organic counterion;
D$_1$=O;
Y'=OR$_1$;
Z'=R$_2$;
both R$_1$ and R$_2$ are linked to the 2' and 3' hydroxyls of the furanose via a common carbon atom according to Formula III,

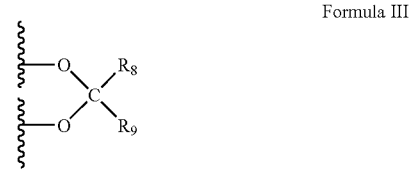

Formula III wherein:
the O atoms are the 2'- and 3'-oxygens of the furanose; and
R$_8$ is hydrogen; and
R$_9$ is selected from the group consisting of aralkyl, aryl, substituted aralkyl, and substituted aryl;
in which the aralkyl groups are straight chained from 1 to 5 carbons, with or without unsaturation and without heteroatoms in the alkyl portion, and are monocyclic moieties from 5 to 6 carbons in the aryl portion; and the aryl groups are monocyclic moieties from 4 to 6 carbons, with or without heteroatoms;
B' is a purine residue according to general Formula IV;
wherein R$_{10}$ is acylamino, according to Formula VI; and
R$_{17}$ is amino or mono- or disubstituted amino such that the moiety according to Formula VI is a urea;
J=carbon;
R$_{11}$ is absent;
R$_{12}$ is hydrogen; and
R$_{13}$ is hydrogen.

4. The P2Y$_{12}$ receptor antagonist compound-eluting stent according to claim 3, wherein said compound is a compound of Formula Ib-2, or a pharmaceutically acceptable salt, solvate, or hydrate thereof;

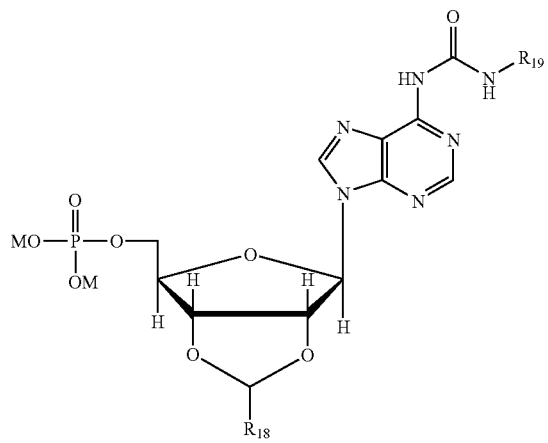

Formula Ib-2 wherein:
R$_{18}$ is phenyl, benzyl, or styryl;
R$_{19}$ is C$_2$ to C$_6$ alkyl; C$_3$ to C$_6$ cycloalkyl; alkylcycloalkyl with one to two carbon atoms in the alkyl portion, and three to six carbons in the cycloalkyl portion; phenyl; substituted or unsubstituted.

5. The P2Y$_{12}$ receptor antagonist compound-eluting stent according to claim 4, wherein R$_{19}$ is ethyl, propyl, butyl, cyclopropyl, cyclopropylmethyl, cyclobutyl, cyclopentyl, or phenyl.

6. The P2Y$_{12}$ receptor antagonist compound-eluting stent according to claim 4, wherein the compound is 2'3' phenylacetaldehyde acetal-6-N-phenylurea AMP; 2'3' phenylacetaldehyde acetal-6-N-n-hexylurea AMP; 2'3' phenylacetaldehyde acetal-6-N-ethylurea AMP; 2'3' phenylacetaldehyde acetal-6-N-cyclopentylurea AMP; 2'3' cinnamyl acetal-6-N-n-hexylurea AMP; 2'3' cinnamyl acetal-6-N-ethylurea AMP; 2'3' cinnamyl acetal-6-N-phenylurea AMP; 2'3' cinnamyl acetal-6-N-n-propylurea AMP; 2'3' cinnamyl acetal-6-N-n-butylurea AMP; 2'3' phenylpropargyl acetal-6-N-phenylurea AMP; 2'3' phenylpropargyl acetal-6-N-n-hexylurea AMP; 2'3' phenylpropargyl acetal-6-N-n-butylurea AMP; 2'3' phenylpropargyl acetal-6-N-n-propylurea AMP; 2'3' phenylpropargyl acetal-6-N-ethylurea AMP; 2'3' benzaldehyde acetal-6-N-ethylurea AMP; 2'3' benzaldehyde acetal-6-N-n-propylurea AMP; 2'3' benzaldehyde acetal-6-N-n-butylurea AMP; 2'3' benzaldehyde acetal-6-N-n-hexylurea AMP; 2'3' benzaldehyde acetal-6-N-cyclopentylurea AMP; 2'3'-(trans) cinnamyl acetal-6-N-ethylurea AMP, 2'3'-(trans)phenyl acetal-6-N-ethylurea AMP; or 2'3'-(cis)phenyl acetal-6-N-ethylurea AMP.

7. The P2Y$_{12}$ receptor antagonist compound-eluting stent according to claim 6, wherein the compound is 2'3'-(trans) cinnamyl acetal-6-N-ethylurea AMP, 2'3'-(trans)phenyl acetal-6-N-ethylurea AMP; or 2'3'-(cis)phenyl acetal-6-N-ethylurea AMP.

8. The P2Y$_{12}$ receptor antagonist compound-eluting stent according to claim 1, wherein A is a nucleoside residue.

9. The P2Y$_{12}$ receptor antagonist compound-eluting stent according to claim 8, wherein said compound is a compound of Formula Ia-1, or a pharmaceutically acceptable salt, solvate, or hydrate thereof:

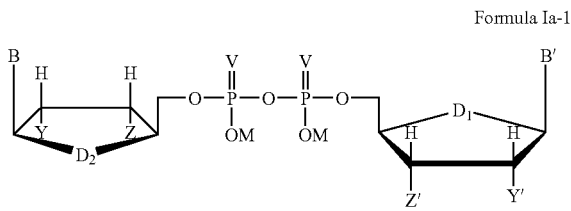

Formula Ia-1 wherein:

V=O;

M=H or a pharmaceutically-acceptable inorganic or organic counterion;

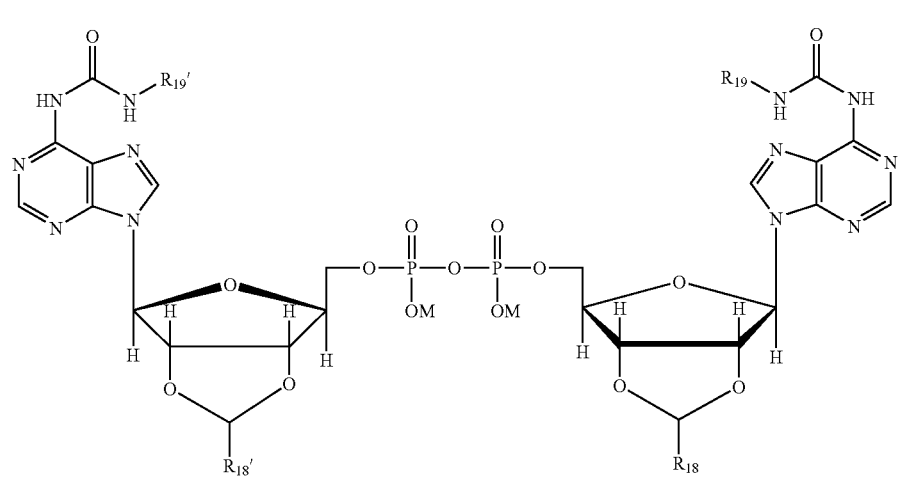

Formula Ia-2

$D_1$ and $D_2$=O;
Y'=OR$_1$;
Z'=OR$_2$;
Z=OR$_3$;
Y=OR$_4$;

$R_1$, $R_2$, $R_3$, and $R_4$ are residues which comprise a moiety linked to the 2' and 3' hydroxyls of the furanose or carbocycle via a common carbon atom according to Formula III,

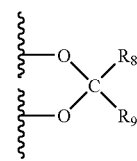

Formula III wherein:

the O atoms are the 2'- and 3'-oxygens of the furanose; and the 2'- and 3'-oxygens of the furanose are linked by a common carbon atom to form a cyclical acetal; and $R_8$ is hydrogen; and $R_9$ is selected from the group consisting of aralkyl, aryl, substituted aralkyl, and substituted aryl;

in which the aralkyl groups are straight chained from 1 to 5 carbons, with or without unsaturation and without heteroatoms in the alkyl portion, and are monocyclic moieties from 5 to 6 carbons in the aryl portion; and the aryl groups are monocyclic moieties from 4 to 6 carbons, with or without heteroatoms;

B' is a purine residue according to general Formula IV;

wherein $R_{10}$ is acylamino, according to Formula VI; and $R_{17}$ is amino or mono- or disubstituted amino such that the moiety according to Formula VI is a urea;

J=carbon;

$R_{11}$ is absent;

$R_{12}$ is hydrogen; and $R_{13}$ is hydrogen.

10. The P2Y$_{12}$ receptor antagonist compound-eluting stent according to claim 9, wherein said compound is a compound of Formula Ia-2:

wherein:

$R_{18}$ and $R_{18'}$ are independently phenyl, benzyl, or styryl; and $R_{19}$ and $R_{19'}$ are independently $C_2$ to $C_6$ alkyl; $C_3$ to $C_6$ cycloalkyl; alkylcycloalkyl with one to two carbon atoms in the alkyl portion, and three to six carbons in the cycloalkyl portion; phenyl; substituted or unsubstituted.

11. The P2Y$_{12}$ receptor antagonist compound-eluting stent according to claim 10, wherein $R_{19}$ and $R_{19'}$ are independently ethyl, propyl, butyl, cyclopropyl, cyclopropylmethyl, cyclobutyl, cyclopentyl, or phenyl.

12. The P2Y$_{12}$ receptor antagonist compound-eluting stent according to claim 10, wherein $R_{18}$=$R_{18'}$ and $R_{19}$=$R_{19'}$.

13. The P2Y$_{12}$ receptor antagonist compound-eluting stent according to claim 10, wherein said compound is P$^1$, P$^2$-di-(2',3'-cinnamyl acetal-6-N-ethylurea adenosine 5'-) diphosphate; P$^1$, P$^2$-di-(2',3'-phenylpropargyl acetal-6-N-ethylurea adenosine 5'-) diphosphate; P$^1$, P$^2$-di-(2',3'-phenylacetaldehyde acetal-6-N-ethylurea adenosine 5'-) diphosphate; or P$^1$, P$^2$-di-(2',3'-phenyl acetal-6-N-ethylurea adenosine 5'-) diphosphate.

14. The P2Y$_{12}$ receptor antagonist compound-eluting stent according to claim 1, wherein said stent is a coronary stent, a cerebral arterial stent, a carotid stent, aortic stent, renal artery stent, or a peripheral artery stent.

15. The $P2Y_{12}$ receptor antagonist compound-eluting stent according to claim 14, wherein said stent is a coronary stent.

16. The $P2Y_{12}$ receptor antagonist compound-eluting stent according to claim 1, wherein the stent is coated with a composition comprising one or more $P2Y_{12}$ receptor antagonist compound and one or more biodegradable polymer.

17. The $P2Y_{12}$ receptor antagonist compound-eluting stent according to claim 1, wherein the stent is coated with a composition comprising one or more $P2Y_{12}$ receptor antagonist compound and one or more biostable polymer.

18. A composition comprising at least one biodegradable polymer and at least one $P2Y_{12}$ receptor antagonist compound of Formula I according to claim 1, wherein said biodegradable polymer is selected from the group consisting of polycaprolactone, polylactic acid, poly(lactide-co-glycolide), poly(hydroxybutyrate), poly(hydroxybutyrate-covalerate), polydioxanone, polyorthoester, polyanhydride, poly(glycolic acid), poly(glycolic acid-cotrimethylene carbonate), polyphosphoester, polyphosphoester urethane, poly(amino acids), poly(trimethylene carbonate), poly(iminocarbonate), cyanoacrylates, polyalkylene oxalates, polyphosphazenes, aliphatic polycarbonates, cellulose, starch, dextran, hyaluronic acid, and collagen.

19. A composition comprising at least one biostable polymer and at least one $P2Y_{12}$ receptor antagonist compound of Formula I according to claim 1, wherein said biostable polymer is selected from the group consisting of polyurethanes, polyesters, polyamides, polyolefins, polycaprolactam, polyvinyl chloride, polyvinyl alcohol, poly(ethylene-vinyl alcohol), polyethers, silicones, acrylate polymers and copolymers, polyvinylmethyl ether, polyimide, and polyacrylonitrile.

20. A method for treating blocked or narrowed arteries, comprising the step of placing a $P2Y_{12}$ receptor antagonist compound-eluting stent according to claim 1 in a narrowed or blocked artery of a patient, whereby a therapeutically effective amount of the compound is eluted to the stented area, whereby the blood flow is resumed and the restenosis and thrombosis are prevented.

21. The method according to claim 20, which further comprises the step of monitoring the patient to ensure patency of the stented artery.

* * * * *